United States Patent

Hagishita et al.

Patent Number: 5,739,162
Date of Patent: Apr. 14, 1998

[54] CARBAMOYLMETHYLUREA DERIVATIVES

[75] Inventors: Sanji Hagishita, Gose; Susumu Kamata, Takarazuka; Yasushi Murakami, Joyo; Nobuhiro Haga, Osaka; Yasunobu Ishihara, Kyoto; Toshiro Konoike, Suita, all of Japan

[73] Assignee: Shionogi & Co., Ltd., Osaka, Japan

[21] Appl. No.: 687,433

[22] PCT Filed: Feb. 7, 1995

[86] PCT No.: PCT/JP95/00161

§ 371 Date: Aug. 9, 1996

§ 102(e) Date: Aug. 9, 1996

[87] PCT Pub. No.: WO95/21856

PCT Pub. Date: Aug. 17, 1995

[30] Foreign Application Priority Data

Feb. 9, 1994 [JP] Japan .................. 6-015189
Oct. 5, 1994 [JP] Japan .................. 6-241555

[51] Int. Cl.⁶ .................................... A61K 31/24
[52] U.S. Cl. .................. 514/534; 514/596; 560/34; 564/48; 564/53
[58] Field of Search .................. 560/34; 564/53, 564/48; 514/596, 535, 534

[56] References Cited

U.S. PATENT DOCUMENTS 5,338,760  8/1994  Bourzat et al. .............. 514/539
5,382,590  1/1995  Bourzat et al. .............. 514/396

Primary Examiner—James H. Reamer
Attorney, Agent, or Firm—Foley & Lardner

[57] ABSTRACT

A compound of the formula (I):

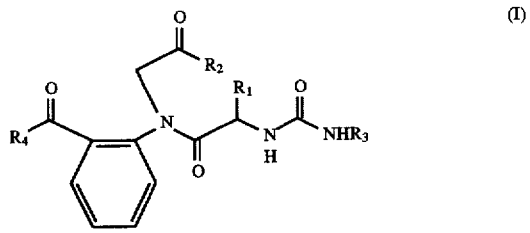

wherein $R_1$ is a hydrogen atom or lower alkyl; $R_2$ is a lower alkoxy, lower alkylamino, lower cycloalkyl, optionally substituted phenyl or optionally substituted heterocyclic group; $R_3$ is an optionally substituted phenyl; $R_4$ is an optionally substituted phenyl, optionally substituted cycloalkyl, optionally substituted alkyl or optionally substituted heterocyclic group, or a pharmaceutically acceptable salt thereof, which has a high affinity for gastrin receptors and/or CCK-B receptors but not for CCK-A receptors, and is useful for treating diseases associated with gastrin receptors and/or CCK-B receptors without inducing the side effects associated with CCK-A receptors.

15 Claims, No Drawings

CARBAMOYLMETHYLUREA DERIVATIVES

FIELD OF THE INVENTION

The present invention relates to novel carbamoylmethylurea derivatives capable of competing with gastrin and/or CCK-B and binding to their receptors, and pharmaceutical compositions which contain the same and are useful in the treatment of various diseases associated with gastrin and/or CCK-B receptors.

BACKGROUND OF THE INVENTION

Gastrin and cholecystokinin (CCK) are physiologically active substances belonging to what is called a gastrin sub-family of the gastrointestinal peptide hormone family. Although gastrin receptors are commonly found in various tissues including the whole superior digestive tract, pancreas, liver, biliary duct and the like, they mainly exist on parietal cells of fundic glands and participate in the mediation of gastric acid secretion. As for CCK receptors, it is known that there are two types of receptors, i.e., CCK-A receptor found in peripheral tissues such as digestive gut and CCK-B receptor found in brain. The former participates in the control of gut motility and pancreas secretion whereas the latter in the control of central nervous action, appestat and the like. Accordingly, it has been expected that compounds capable of competing with gastrin and/or CCK-B and binding to their receptors are useful in the treatment of animals including human suffering from gastrointestinal and central nervous diseases associated with receptors for these peptide hormones. For example, such compounds are thought to be useful as an anti-tumor agent; a drug for treating pancreatitis, gallbladder disorder or irritable bowel syndrome, for relieving biliary colic, and for improving appetite. Further, investigations into receptors in both gastrointestinal and central nervous system revealed that these gastrointestinal peptide hormones are also important as biologically active substances ["Brain and Peptides" Taisha, vol. 18, No. 10, 33–44 (1981); J. Hughus, C. Woodruff, D. Horwell, A. McKnight & D. Hill, "Gastrin", J. H. Walsh ed., Rovan Press, Ltd., New York, 1993, p. 169–186; F. Makovec, Drugs of the Future, 18, 919 (1993); Japanese Patent Publication (KOKAI) 63-238069, EP 167,919; U.S. Pat. No. 4,820,834; EP 284,256; U.S. Pat. No. 5,004,741].

For instance, gastrin antagonists specific to gastrin receptors are thought to be effective on gastrin-associated disorders such as peptic ulcers in gaster and duodenum, Zollinger-Ellison syndrome, hyperplasia of sinus G cells, and decrease in gastrin activity. The usefulness of antagonists specific to gastrin-receptor in the treatment of gastric and duodenal ulcers has been reported (Taisha, 29/7, 1992, R. Eissele, H. Patberg, H. Koop, W. Krack, W. Lorenz, A. T. McKnight & R. Arnold, Gastroenterology, 103, 1596 (1992), etc.)

There have been reported that antagonists against CCK-B receptor are useful in the reinforcement and elongation of the analgetic effect of opioid-type compounds (e.g., morphine derivatives such as morphine sulfate or hydrochloride) which are antagonistic against opioid receptors [Drugs of the future 18, 919 (1993); Proc. Natl. Acad. Sci. U.S.A., Vol. 87, p. 71, 05 Sep. 1990, Neurobiology].

As compounds useful in the above-mentioned treatment, there have been reported certain benzodiazepine derivatives of closed ring-type [e.g., L-365260 described in the Japanese Patent Appln. Publication KOKAI No. 63-238069; YM022 described in WO 92/11246; and compounds described in WO 93/14074 and WO 93/14075)] or other ring closed-type compounds [e.g., CI-988 described by Martin J. Drysdale et al., J. Med. Chem. 35:2573–2581 (1992); RP 72540 described in Drugs of the Future, 1993, 18(10); and LY-288513 described in J. Pharmacol. Exp. Ther., 264, 480 (1993)], which are antagonistic against gastrin receptor or CCK-B receptor. However, many of those disclosed prior to the present invention do not have sufficient affinity for each receptor or lack in any specific pharmacological data. Thus, there have been provided no clinically applicable anti-ulcer agents with gastrin receptor antagonistic effect. Accordingly, it is necessary to develop a compound capable of binding to an intended peptide hormone receptor in preference discriminating it from that for peptide hormones of different sub-types in order to conduct treatment more efficiently.

DISCLOSURE OF THE INVENTION

In the situations above, the present inventors have studied intensively to develop compounds which have high affinity for gastrin receptors and/or CCK-B receptors with high selectivity but low affinity for CCK-A receptors, and found that certain carbamoylmethylurea derivatives are useful for the purposes above and established the present invention.

Thus, the present invention provides a compound of the formula (I):

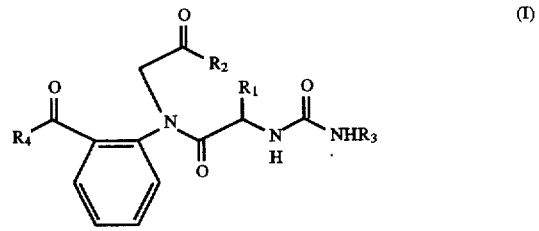

wherein $R_1$ is a hydrogen atom or lower alkyl; $R_2$ is a lower alkoxy, lower alkylamino, lower cycloalkyl, optionally substituted phenyl or optionally substituted heterocyclic group; $R_3$ is an optionally substituted phenyl; $R_4$ is an optionally substituted phenyl, optionally substituted cycloalkyl, optionally substituted alkyl or optionally substituted heterocyclic group, or a pharmaceutically acceptable salt thereof.

Although all the compounds (I) as defined above are useful to achieve the purposes of the present invention, those of the formula (I) wherein $R_1$ is a hydrogen atom, $R_2$ is a lower alkoxy or lower alkylamino, especially t-butoxy, $R_3$ is an optionally substituted phenyl, especially carboxyphenyl, and $R_4$ is an optionally substituted phenyl, especially phenyl are preferred.

THE BEST EMBODIMENT FOR PRACTICING THE EMBODIMENT

The present invention will hereinafter be explained in more detail.

Throughout the present specification, the terms "gastrin receptor antagonist" or "CCK-B receptor antagonist" is referred to a compound capable of competitively inhibiting the binding of gastrin receptor or CCK-B receptor with respective natural ligand, and is used interchangeably with the term "gastrin antagonist" or "CCK-B antagonist", respectively. Since the compound (I) of the present invention has a strong affinity for gastrin receptors and/or CCK-B receptors and can bind to them specifically competing with their natural ligands, it may be referred to as "gastrin receptor antagonist" or "CCK-B receptor antagonist".

Because of the same reason above, the terms "gastrin receptor antagonism" and "gastrin antagonism", and the terms "CCK-B receptor antagonism" and "CCK-B antagonism" are used exchangeably.

The terms used in the definition of compound (I) are defined below.

The term "alkyl" means straight or branched chain $C_1$-$C_{10}$ hydrocarbon group including octyl, nonyl and decyl in addition to lower alkyl as defined below.

The term "lower alkyl" means straight or branched chain $C_1$-$C_8$ hydrocarbon group including methyl, ethyl, n-propyl, i-propyl, n-butyl, s-butyl, t-butyl, n-pentyl, i-pentyl, neopentyl, s-pentyl, t-pentyl, n-hexyl, neohexyl, i-hexyl, s-hexyl, t-hexyl, heptyl and octyl, and $C_1$-$C_3$ hydrocarbon group is preferred.

The term "lower cycloalkyl" means $C_3$-$C_7$ cycloalkyl group including cyclopropyl, cyclobutyl, cyclopentyl, cyclohexyl and cycloheptyl.

The term "lower alkoxy" means straight or branched chain $C_1$-$C_6$ alkoxy group including methoxy, ethoxy, n-propoxy, i-propoxy, n-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy and t-hexyloxy. Preferred alkoxy is $C_1$-$C_4$ alkoxy, in particular t-butoxy.

The term "lower alkylamino" means a group derived from amino group as defined above through the replacement of hydrogen by lower alkyl, including methylamino, ethylamino, n-propylamino, i-propylamino, n-butylamino, t-butylamino, and the like.

The term "heterocyclic group" means 5- to 7-membered both aromatic- and non-aromatic heterocyclic groups containing one or more hetero atoms selected independently from the group consisting of O, S and N. Examples of aromatic heterocyclic group include furyl, thienyl, tetrazolyl, pyrrolyl, pyrazolyl, imidazolyl, oxazolyl, thiazolyl, pyridinyl, oxadinyl and triazinyl. Examples of non-aromatic heterocyclic group include pyrrolidinyl, thiazolidinyl, oxazolidinyl, imidazolidinyl, thiazolinyl, oxazolinyl, imidazolinyl, piperidinyl, piperadinyl, morpholinyl, thiomorpholinyl, oxadiazolyl and dioxanyl.

Preferred heterocyclic groups are, in the case of $R_2$, pyrrolidinyl and morpholinyl, and in the case of $R_4$, those containing N-atom, especially, piperidinyl optionally protected with amino-protecting group.

In the definition of $R_2$, the term "optionally substituted phenyl" means a phenyl which may be substituted by 1-3 substituents selected from, for example, amino, hydroxy, halogen, lower alkyl and halogenated lower alkyl, at ortho-, metha- and/or para-position.

The term "halogen" means bromine, chlorine, fluorine or iodine.

In the definition of $R_2$, the term "optionally substituted heterocyclic group" means a heterocyclic group which may be substituted by 1-3 substituents selected from, for example, amino, hydroxy, halogen, lower alkyl and halogenated lower alkyl.

In the definition of $R_3$, the term "optionally substituted phenyl" means a phenyl which may be substituted by a substituent(s) selected from, for example, halogen, cyano, lower alkoxy, lower alkyl, halogenated lower alkyl, —$R_5$—$(CH_2)_n$—$R_6$ [$R_5$ is a bond, —O—, —S— or —S(O)—, $R_6$ is an aromatic heterocyclic group or —$COOR_7$ ($R_7$ is a hydrogen, lower alkyl, lower alkenyl, or aralkyl), n is an integer of 0 to 3], $NO_2$, $NH_2$, OH, SMe, CONH, $OCF_3$, $CH_2CN$, $CH_2OH$, $CH_2OMe$, $CH_2NH_2$ and the like, preferably —$COOR_7$, at ortho-, metha- and/or para-position.

The term "aralkyl" means a group derived from alkyl through the replacement of hydrogen by aryl group, including benzyl, phenylethyl, methylbenzyl naphtylmethyl and the like. Benzyl is especially preferred.

In the definition of $R_4$, the term "optionally substituted phenyl", "optionally substituted alkyl", "optionally substituted heterocyclic group" or "optionally substituted cycloalkyl" means each group which may be substituted by 1-3 substituents selected from, for example, electron attracting- or releasing-groups such as amino, hydroxy, halogen, lower alkyl, halogenated lower alkyl and lower alkoxy at ortho-, metha- and/or para-position.

The term "halogenated alkyl" or "halogenated lower alkyl" means an alkyl or lower alkyl group as defined above which is substituted by halogen atoms, preferably by 1-3 ones including —$CF_3$, —$CHF_2$—, —$CH_2F$—, —$CH_2CCl_3$—, —$CH_2CHClCH_3$— and the like.

The compound (I) of the present invention can be prepared using any methods known in the art. Typical procedures are illustrated below, however, which are not restrictive.

Method 1

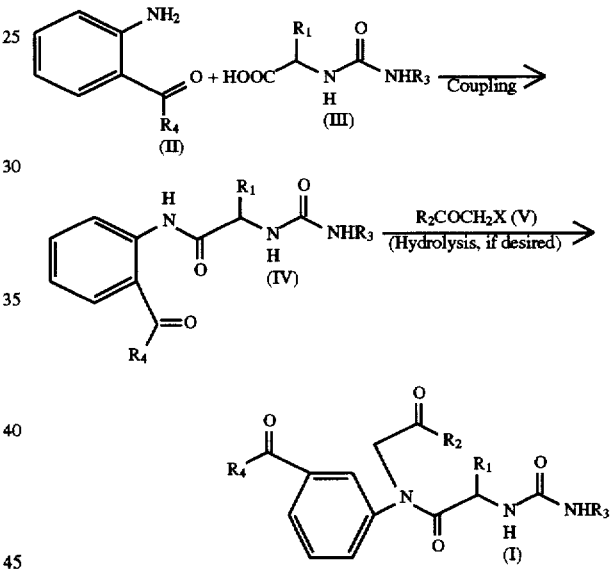

in which $R_1$, $R_2$, $R_3$ and $R_4$ are as defined above, and X represents a halogen.

The reaction of 2-substituted aniline derivative of the formula (II) and the compound of the formula (III) which if desired is N-protected, is carried out under the conventional coupling condition. The coupling reaction is carried out according to any conventional method, for example, 1) the method in which the reaction is directly carried out by using a coupling agent such as dicyclohexylcarbodiimide, 1-(3-dimetylaminopropyl)-3-ethylcarbodiimide or the like; 2) the method in which the amino acid (III) is reacted with thionyl chloride to obtain acid chloride, which is then reacted with the ketone (II); or 3) the method in which the amino acid (III) is reacted with ethylchlorocarbonate to synthesize an active ester, which is then reacted with the ketone (II). Then, the obtained product is appropriately deprotected by a conventional method, for example, by treating with a hydrogen bromide solution in acetic acid.

The resulting amide compound (IV) is reacted with the halide (V) of the formula: $R_2COCH_2X$ in the presence of an appropriate base such as an alkali metal hydroxide (NaOH, etc.) or a carbonate (K$_2$CO$_3$), in a solvent such as dimethylformamide. The reaction product (I) can be derived to the other compound (I) which also is useful for the purpose of the present invention, by appropriately modifying the substituent R$_3$. The final product may be purified by the conventional purification methods used in the art, for example, extraction with an organic solvent such as ethyl acetate, drying, concentration, chromatography, crystallization from an appropriate solvent, and the like.

Method 2

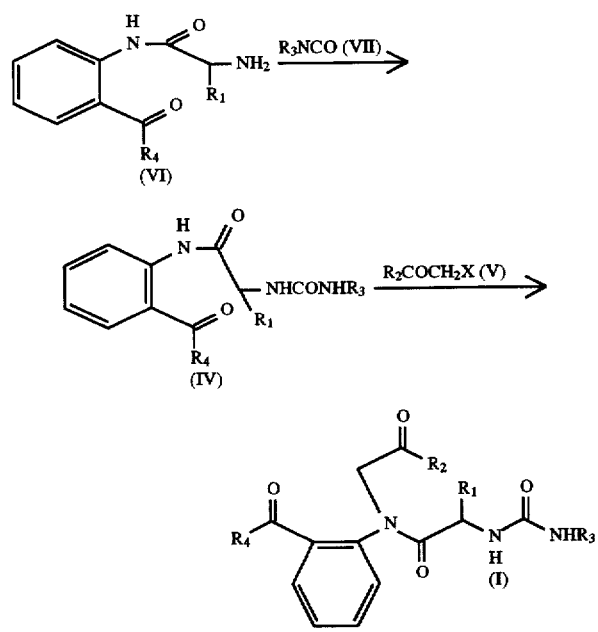

in which R$_1$, R$_2$, R$_3$, R$_4$ and X are as defined above.

The amino compound (VI), a starting material for the Method 2, is obtained, for example, by the method in which the ketone of the above formula (II) is reacted with a N-protected amino acid derivative containing an appropriate side chain R$_1$, and then deprotected.

The coupling reaction between the ketone (II) and the N-protected amino acid derivative and the deprotection are carried out under the conventional conditions for coupling and deprotection as mentioned in Method 1 above.

The reaction between the amino compound (VI) and the isocyanate derivative of the formula (VII) is carried out by mixing them in an appropriate solvent at room temperature.

Then, in the same way as the Method 1, the amide (IV) is reacted with the halide (V) to obtain the compound of the formula (I), which, if desired, appropriately modified to derive the other compound (I) of the present invention.

In addition, the producing method shown by the following reaction scheme may be employed.

Method 3

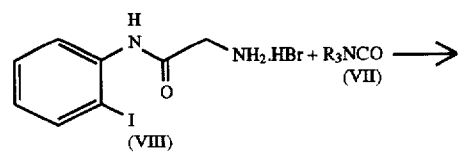

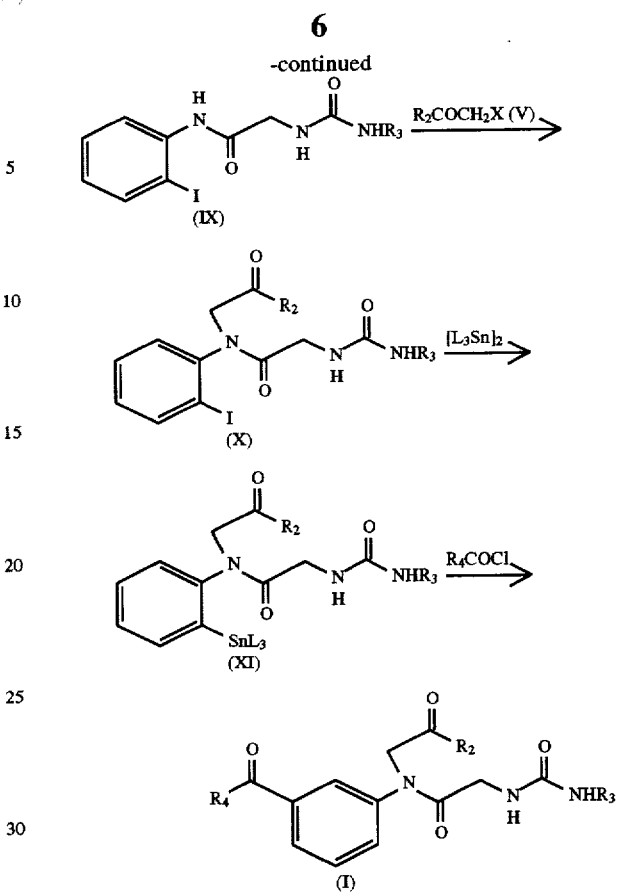

in which R$_1$, R$_2$, R$_3$, R$_4$ and X are as defined above, and L represents a lower alkyl.

The starting material (VIII) can be prepared by coupling orthoiodoaniline and Cbz glycine to obtain an amide compound, and then deprotecting the amide compound. The reaction between the compound (VIII) and the isocyanate derivative (VII) is carried out at room temperature in the presence of a base such as triethylamine, in an appropriate solvent. Then, as mentioned in the Method 1, the amide (IX) is reacted with the halide (V) to synthesize the iodide (X). The iodide (X) is reacted with hexaalkylditin in the presence of trans-benzylchlorobistriphenylphosphine palladium and tetraethylammonium chloride catalysts to obtain the alkyltin compound (XI). The tin compound (XI) is reacted with acid chloride in the presence of dichlorobisacetonitrile palladium catalyst to obtain the compound (I).

Method 4

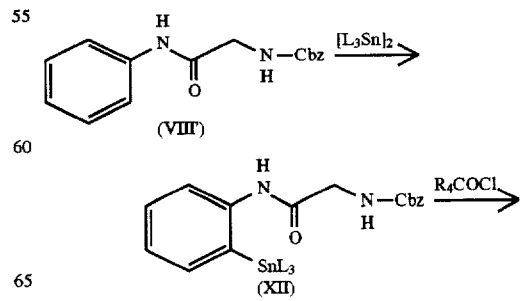

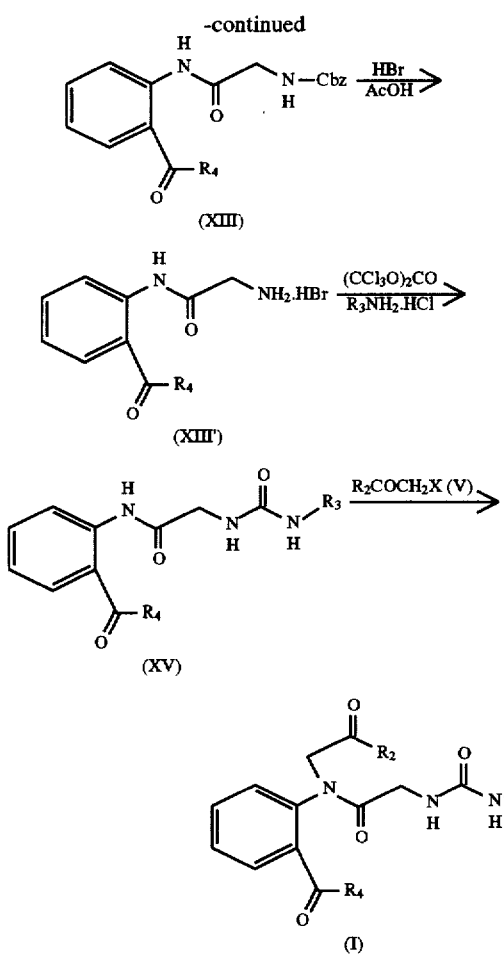

in which $R_1$, $R_2$, $R_3$, $R_4$, L and X are as defined above, Cbz represents benzyloxycarbonyl.

As described in Method 3, the iodide (VIII') is reacted with hexaalkylditin to obtain the alkyltin compound (XII). Then, the compound (XII) is reacted with acid chloride to obtain the ketone (XIII), and the ketone is deprotected to obtain the amine (XIII'). The amine (XIII') is mixed with the isocyanate synthesized in situ to obtain the urea compound (XV), which is then reacted with the halogen compound (V) as described in Method 1 to obtain the compound (I) .

Each method described above is only a part of suitable methods for preparing the compound (I) of the present invention. It is also possible to prepare the compound (I) of the present invention by combining an appropriate starting material with any method known in the art. The compound (I) thus prepared may also fall within the scope of the present invention.

The compound (I) of the present invention may form salts with a conventional inorganic acid or organic acid, or inorganic base or organic base. The salts of the compound (I) include salts with alkali metal such as sodium and potassium, or with alkali earth metal such as calcium and magnesium; salts with organic base such as ammonium, trimethylamine, triethylamine, pyridine, picoline, dicyclohexylamine, and N,N-dibenzylethylenediamine; salts with organic acid such as acetic acid, maleic acid, tartaric acid, methanesulfonic acid, benzenesulfonic acid, formic acid, toluenesulfonic acid and trifluoroacetic acid; salts with inorganic acid such as hydrochloric acid, hydrobromic acid, sulfuric acid and phosphoric acid; and salts with amino acid such as arginine, aspartic acid and glutamic acid. Preferred salts are conventional inorganic salts.

Anti-acid secreting function of carbamoylmethylurea derivative (I) of the present invention has been confirmed by the in vivo experiment (cf. Schild Method; Experiment 1 below). Then, with respect to the various compounds, in vivo experiments were carried out about the gastrin receptor antagonism function and the CCK-B receptor antagonism function, and showed that the carbamoylmethylurea derivative (I) has these two functions (cf. Experiment 2 below). From the results of these experiments, it is apparent that the carbamoylmethylurea derivative (I) has an anti-acid secreting function, and is an excellent gastrin receptor antagonist and/or CCK-B receptor antagonist which has enough functional separativeness from CCK-A receptor.

Thus, the carbamoylmethylurea derivative of the compound according to the present invention and its salt have a high affinity for gastrin receptor and/or CCK-B receptor, and also have in vivo inhibitory function against acid secretion caused by the stimulation of pentagastrin. Accordingly, the derivative and its salt are useful as a therapeutical medicine which does not induce the side effect in connection with the CCK-A receptor, and is effective on the diseases which are induced by the disorder of the physiological function related to gastrin receptor, particularly, such as gastric ulcer, duodenal ulcer, gastritis, reflux esophagitis, and Zollinger-Ellison syndrome. Moreover, they are considered to have the function to increase or to maintain the analgetic effect induced by opioid medicines (opioid-induced analgetic effect, and hence they may be expected to be useful for combined use with analgesics.

Therefore, the present invention provides the pharmaceutical composition containing the compound of the formula (I), together with pharmaceutically acceptable carrier, excipient and the like.

More particularly, the present invention provides the pharmaceutical composition comprising therapeutically effective amount of the compound (I) and pharmaceutically acceptable carrier, which is useful as the therapeutical medicine for the diseases which are induced by the disorder of the physiological function controlled by gastrin receptor, particularly, such as gastric ulcer, duodenal ulcer, gastritis, reflux esophagitis, and Zollinger-Ellison syndrome, without causing the side effect related to the CCK-A receptor.

In addition, the present invention provides the pharmaceutical composition comprising therapeutically effective amount of the compound (I) and pharmaceutically acceptable carrier, which is useful as a therapeutical medicine or an antianxiety agent for treating the central nervous system disorder induced by the disorder of the physiological function controlled by the CCK-B receptor, for example, the diseases induced by appestat disorder without causing the side effect related to the CCK-A receptor. Moreover, the compound (I) of the present invention is considered to have the function to increase or to lengthen the analgetic effect induced by opioid medicines, and hence it may be expected to be useful in combined use with the analgesics.

The compound (I) of the present invention may be used alone or in combination with other medicines. The combination treatment may be carried out by mixing the compound (I) of the present invention with one or more of pharmacologically acceptable active components to form a single pharmaceutical composition, or by consecutively administering them.

When the compound (I) of the present invention is used for treatment, a derivative can be administered orally or parenterally. When the oral administration is employed, the compound of the present invention can be formulated into ordinary formulations in the form of solid such as tablets, powders, granules, capsules, etc; solutions; oily suspensions; or liquid formulations such as syrups, elixirs, etc. When the parenteral administration is employed, the compound of the present invention can be used as oily injection or oily suspension injection. In preparing these formulations, conventional excipients, binding agents, lubricants, aqueous solutions, oily solutions, emulsifiers, suspending agents, and the like may be used, and also other additives such as preservatives, stabilizers, and the like may be used.

The dosage of the compound of the present invention varies depending upon the administration route, age of the patient, weight and state, and the type of diseases, but in the case of oral administration, it may usually be about 5–500 mg/day/adult, preferably about 10–200 mg, more preferably, about 20–100, in 1–2 divisions. In the case of the parenteral administration, the dosage may be about 1–20 mg/day/adult, more preferably, about 2–10 mg, in 1–2 divisions.

The following examples are provided to further illustrate the present invention in detail, but they are only for illustrative purpose and are not to be construed as limiting the scope of the present invention.

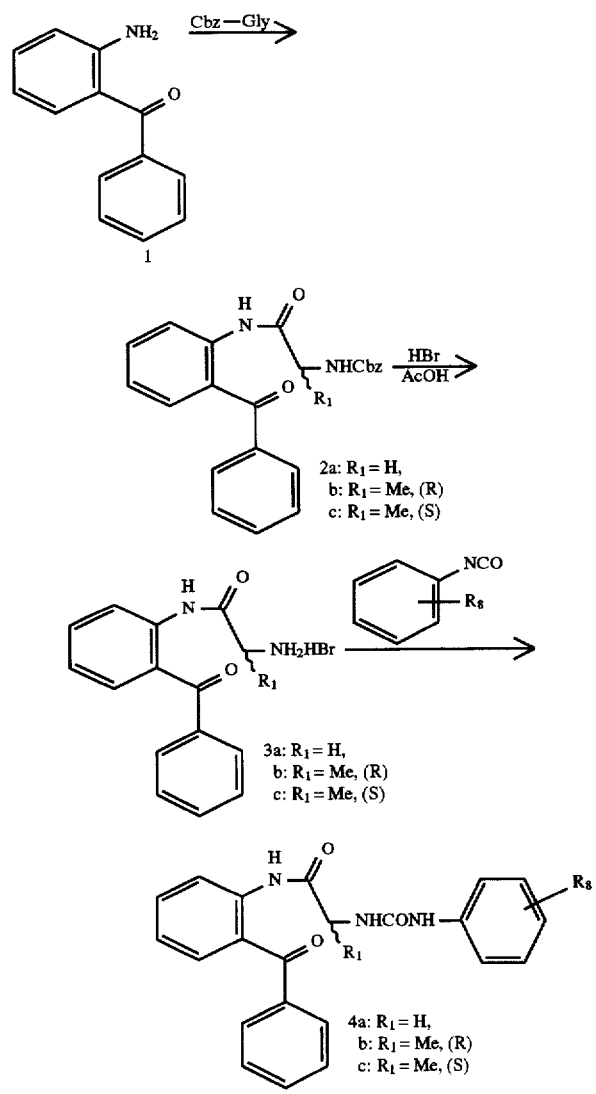

Preparation 1

2-(Benzyloxycarbonylglycylamino)benzophenone 2a

1) Triethylamine (26 ml) is poured under ice cooling into a mixture of 2-aminobenzophenone (12 g, 60.8 mmol), N-benzyloxycarbonyl(Cbz)glycine (12.73 g, 60.8 mmol), 1-(3-dimethylaminopropyl)-3-ethylcarbodiimide hydrochloride (12.25 g, 63.9 mmol) and 1-hydroxybenzotriazole (1.07 g, 7.9 mmol) in tetrahydrofuran (250 ml). The mixture is stirred overnight at room temperature. The mixture is poured into water and then the resultant mixture is extracted with ethyl acetate. The extract is distilled under reduced pressure. The residue is recrystallized from 2-propanol. Yield 65%, Mp. 115°–117° C.

IR $\nu_{max}$ (KBr): 3306, 1693, 1637, 1538, 1534, 1521 cm$^{-1}$.
NMR (CDCl$_3$) δ: 4.07 (2H,d,J=5.8 Hz), 5.17 (2H,s), 5.52 (1H,br,s,), 7.1–7.69 (9H,m), 8.63 (1H,d,J=8.6 Hz), 11.36 (1H,br,s).

Elemental analysis (C$_{23}$H$_{20}$N$_2$O$_4$) Calcd.: C, 71.12; H, 5.19; N, 7.21 Found: C, 71.35; H, 5.36; N, 7.28.

2) Thionyl chloride (4 ml, 55 mmol) is added dropwise to a solution of N-benzyloxy-carbonylglycine (12.6 g, 60 mmol) in hexamethylphosphonyltriamide (70 ml) and acetonitrile (20 ml) under stirring at –4°–5° C., and the stirring at –5° C. is continued for another 10 minutes. 2-Aminobenzophenone (9.86 g, 50 mmol) is added to the reaction mixture in five portions, and the mixture is stirred at room temperature for 3 hours. The reaction mixture is neutralized with a saturated aqueous solution of sodium hydrogencarbonate, and extracted with ethyl acetate. The organic phase is washed with water, dried (magnesium sulfate) and then concentrated under reduced pressure. The resultant raw product is recrystallized from hexane to obtain the title compound 2a (18.89 g, 97.3%).

Preparation 2

(–)- and (+)-2-(Benzyloxycarbonylalanylamino) benzophenone 2b, 2c

The same procedure as Preparation 1 is carried out by using N-benzyloxycarbonyl-L-alanine to obtain a compound 2b of (–)- type. Yield 74.0%, Mp. 95° C.

[α]D$^{24}$–16.7 (c 1.046, CHCl$_3$).

IR $\nu_{max}$ (KBr): 3290, 1728, 1697, 1585, 1512 cm$^{-1}$.
NMR (CDCl$_3$) δ: 1.52(3H,d,J=7.0 Hz), 4.45(1H,m), 5.14 (2H,s), 5.45(1H,d,J=5.0 Hz), 7.12(1H,dt,J=1.8,8.0 Hz), 7.2–7.7(13H,m), 8.65(1H,d,J=10.0 Hz).

Elemental analysis (C$_{24}$H$_{22}$N$_2$O$_4$) Calcd.: C, 71.63; H, 5.51; N, 6.96 Found: C, 71.64; H, 5.49; N, 6.99.

(+)-Type compound (2c) is also synthesized by using N-benzyloxycarbonyl-d-alanine as a staring material in the same way as the (–)-type compound (2b).

[α]D$^{23}$+13.6 (c 1.01, CHCl$_3$).

Preparation 3

2-(Glycylamino)benzophenone hydrobromide 3a

A mixture of N-benzyloxycarbonyl derivative (2a, 3.13 g, 8.06 mmol) obtained in Preparation 1 and a solution of 30% hydrobromic acid in acetic acid is stirred for 1 hour. Excess ether is added, and the resultant precipitate is filtered off. After washing with ether, it is dried to obtain 2.50 g (92%) of hydrobromate (compound 3a).

NMR (CDCl3) δ: 3.42 (2H, br.s), 4.11 (2H,br.s), 6.95 (1H,t,J=7.8 Hz), 7.3–8.22 (9H,m), 10.80 (1H, br.s).

Preparation 4

(−)- and (+)-2-(Alanylamino)benzophenone hydrobromide 3b and 3c

The compounds 2b and 2c prepared in Preparation 2 are used as starting materials and treated as described in the above Preparation 3 to obtain the objective compounds 3b and 3c, respectively.

Preparation 5

2-(N'-(m-Tolyl)ureidomethylcarbonylamino) benzophenone 4a

A solution of m-tolylisocyanate (0.846 g, 6.35 mmol) in dimethylformamide (3 ml) is added to a solution of the salt 3a prepared in Preparation 3 (1.937 g, 5.78 mmol) in dimethylformamide (8 ml). Triethylamine (32 ml) is added at 0° C. The mixture is stirred at 0° C. for 30 minutes and then at room temperature overnight. Water and then 10% hydrochloric acid are added. The mixture is extracted with ethyl acetate. The extract is washed with water and dried (sodium sulfate), and then the solvent is distilled off under reduced pressure. The residue is recrystallized from acetonitrile to obtain the objective compound 4a (1.39 g; yield 62%).

IR) $v_{max}$ (KBr): 3310, 1684, 1639, 1590, 1523 cm$^{-1}$.

NMR (CDCl$_3$) δ: 2.21 (3H, s), 4.07 (2H,d,J=5.4 Hz), 5.93 (1H,t,J=5.7 Hz), 6.83 (1H,m), 7.07–7.65 (13H,m), 8.56 (1H,d,J=8.8 Hz), 11.20(1H,s).

Elemental analysis (C$_{23}$H$_{21}$N$_3$O$_3$) Calcd.: C, 71.30; H, 5.46; N, 10.85 Found: C, 71.45; H, 5.54; N, 10.90.

Preparation 6

(+)- and (−)-2-(1-(N'-(m-Tolyl)ureido) ethylcarbamoyl)benzophenone 4b, 4c

The compounds 3b and 3c prepared in Preparation 4 are used as starting materials and treated as described in Preparation 5 to obtain the corresponding compounds 4b and 4c, respectively.

Compound (4b)

Yield 75.0%, Mp 160° C.

[α]$_D^{23}$+18.8 (c 1.075, CHCl$_3$).

IR $v_{max}$ (nujol): 3298, 1683, 1651, 1636, 1582, 1552 cm$^{-1}$.

NMR (CDCl$_3$) δ: 1.45 (3H,d,J=7.0 Hz), 2.19 (3H,s), 4.61 (1H,qui,J=7.0 Hz), 5.95 (1H, br.s), 6.79 (1H,br.s), 7.0–7.7 (12H,m), 8.55 (1H,d,J=8.6 Hz), 11.32 (1H,s).

Elemental analysis (C$_{24}$H$_{23}$N$_3$O$_3$) Calcd.: C, 71.80; H, 5.77; N, 10.49 Found: C, 71.63; H, 5.88; N, 10.55.

Compound (4c)

[α]$_D^{23}$−21.6 (c 1.012, CHCl$_3$)

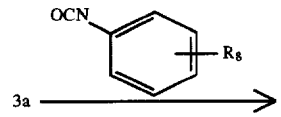

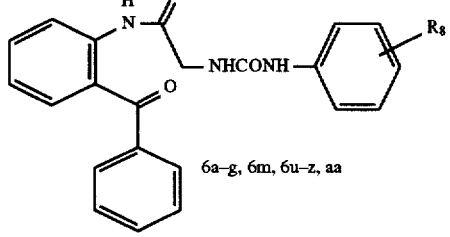

$R_8$ = a: —COOCH$_2$Ph, b: —COOCH$_2$CH=CH$_2$,
c: —CH$_2$COOCH$_2$CH=CH$_2$,
d: —OCH$_2$COOCH$_2$CH=CH$_2$,
e: —SCH$_2$COOCH$_2$CH=CH$_2$, f: triazole-NTr, g: —OCH$_2$-triazole-NTr, m: —CH$_2$COOMe, t: —CF$_3$ u: m-Cl, v: m-Br, w: m-CN, x: m-OCH$_3$, y: p-Cl, z: p-Me, aa: H Preparation 7

2-(N'-(m-(Benzyloxycarbonyl)phenyl) ureidomethylcarbamoyl)benzophenone 6a

In the same manner as described in Preparation 5, the titled compound is prepared by using the compound 3a prepared in Preparation 3 and the corresponding isocyanate. Mp. 157°–159° C.

IR $v_{max}$ (KBr): 3360, 1720, 1680, 1635, 1584, 1560, 1520 cm$^{-1}$.

NMR (DMSO-d$_6$) δ: 3.74 (2H,d,J=5.2 Hz), 5.33 (2H,s), 6.51 (1H,br.s), 7.20–7.70 (16H,m), 7.88 (1H,d,J=8.8 Hz), 8.06 (1H,br.s), 9.13 (1H, s), 10.53 (1H,s).

Elemental analysis (as C$_{30}$H$_{25}$N$_3$O$_5$) Calcd.: C, 71.00; H, 4.97; N, 8.28 Found: C, 71.15; H, 5.06; N, 8.30.

Preparation 8

2-(N'-(m-(2-Propenyloxycarbonyl)phenyl) ureidomethylcarbamoyl)benzophenone 6b

In the same manner as Preparation 7, the title compound is synthesized from the compound 3a and the corresponding isocyanate. Mp. 68°–71° C.

IR $v_{max}$ (KBr): 3350, 1718, 1692, 1659, 1595, 1580, 1557, 1520 cm$^{-1}$

NMR (CDCl$_3$) δ: 4.12 (2H,d,J=5.6 Hz), 4.77 (2H,d,J=5.6 Hz), 5.20–5.43 (2H,m), 5.88–6.10 (2H,m), 7.04–7.18 (3H, m), 7.36–7.70 (10H,m), 7.90 (1H,br.s), 8.54 (1H,d,J=8.6 Hz).

Elemental analysis (C$_{26}$H$_{23}$N$_3$O$_5$) Calcd.: C, 68.26; H, 5.07; N, 9.19 Found: C, 68.30; H, 5.19; N, 9.16.

Preparation 9

2-(N'-(m-(2-Propenyloxycarbonylmethyl)phenyl) ureidomethylcarbamoyl)benzophenone 6c In the same manner as described in Preparation 7, the title compound is synthesized from the compound 3a and the corresponding isocyanate. Mp. 125°–127° C.

IR) $v_{max}$ (KBr): 3330, 1740, 1682, 1639, 1600, 1560, 1520 cm$^{-1}$.

NMR (CDCl$_3$) δ: 3.55 (2H,s), 4.08 (2H,d,J=5.8 Hz), 4.56 (2H,d,J=5.8 Hz), 5.13–5.32(2H,m), 6.91–5.98 (2H,m), 6.91–6.99 (1H,m), 7.05–7.32 (6H,m), 7.38–7.70 (7H,m), 8.57 (1H,d,J=8.6 Hz).

Elemental analysis (as $C_{27}H_{25}N_3O_5$) Calcd.: C, 68.78; H, 5.34; N, 8.91 Found: C, 68.89; H, 5.46; N, 8.88.

Preparation 10

2-(N'-(m-(2-Propenyloxycarbonylmethyloxy)phenyl) ureidomethylcarbamoyl)benzophenone 6d In the same manner as described in Preparation 7, the titled compound is synthesized from the compound 3a and the corresponding isocyanate. Mp. 147°–149° C.

IR $v_{max}$ (KBr): 3330, 1748, 1680, 1653, 1638, 1605, 1563, 1530, 1500 cm$^{-1}$.

NMR (CDCl$_3$) δ: 4.11 (2H,d,J=5.8 Hz), 4.58 (2H,s), 5.18–5.37(2H,m), 5.70–5.99(2H,m), 6.60 (1H,dd,J=7.6, 2.6 Hz), 6.90 (1H,d,J=9.0 Hz), 7.05–7.18 (4H,m), 7.40–7.71 (7H,m), 8.59 (1H,d,J=10.0 Hz), 11.28 (1H,s).

Elemental analysis ($C_{27}H_{25}N_3O_6$) Calcd.: C, 66.52; H, 5.17; N, 8.62 Found: C, 66.54; H, 5.25; N, 8.66.

Preparation 11

2-(N'-(m-(2-Propenyloxycarbonylmethylthio) phenyl)ureidomethylcarbamoyl)benzophenone 6e In the same manner as described in Preparation 7, the titled compound is synthesized from the compound 3a and the corresponding isocyanate.

IR) $v_{max}$ (CHCl$_3$): 3350, 1733, 1682, 1640, 1584, 1521 cm$^{-1}$.

NMR (CDCl$_3$) δ: 3.60 (2H,s), 4.09 (2H,d,J=5.6 Hz), 4.47–4.62 (2H,m), 5.10–5.31 (2H,m), 5.70–5.93 (1H,m), 6.00–6.15 (1H,br.s), 6.92–7.20 (4H,m), 7.32–7.71 (9H,m), 8.56 (1H,d,J=8.6 Hz).

Elemental analysis ($C_{27}H_{25}N_3O_5S$) Calcd.: C, 63.94; H, 5.05; N, 8.28; S, 6.32 Found: C, 63.96; H, 5.18; N, 8.24; S, 6.29.

Preparation 12

2-(N'-(m-(2-(Triphenylmethyl)tetrazol-5-yl)phenyl) ureidomethylcarbamoyl)benzophenone 6f The titled compound is synthesized in the same manner as described in Preparation 5 using an isocyanate which is synthesized in situ from 3-amino-(1H-(triphenylmethyl)-tetrazol-5-yl)benzene (567 mg, 3.52 mmol) synthesized from 3-aminobenzonitrile according to the method described in EPO 508769 A1, and the compound 3a. Powder.

IR $v_{max}$ (KBr): 3375, 1695, 1660, 1640, 1595, 1580, 1560, 1513 cm$^{-1}$

NMR (CDCl$_3$) δ: 4.06 (2H,d,J=5.8 Hz), 5.91 (1H,br.s), 6.95–7.80 (28H,m), 7.91 (1H,s), 8.50 (1H,d,10.0 Hz).

Elemental analysis ($C_{42}H_{33}N_7O_3 \cdot 0.5H_2O$) Calcd.: C, 72.82; H, 4.95; N, 14.15 Found: C, 72.92; H, 5.17; N, 13.16.

Preparation 13

2-(N'-(m-(2-Triphenylmethyl)tetrazol-5-ylmethyloxy)phenyl)ureidomethylcarbonylamino) benzophenone 6g The titled compound is synthesized from the compound 3a and the isocyanate prepared in situ from 3-amino-(1H-(triphenylmethyl)tetrazolylmethoxybenzen and triphosgene.

IR δ$_{max}$(KBr): 3380, 1690, 1660, 1639, 1600, 1580, 1553, 1520 cm$^{-1}$.

NMR (CDCl$_3$) δ: 4.04 (2H,d,J=5.8 Hz), 5.24 (2H,s), 5.93 (1H,t,J=5.8 Hz), 6.61–6.69 (1H,m), 6.88–7.65 (24H,m), 8.59 (1H,d,J=8.8 Hz), 11.28 (1H, s).

Elemental Analysis ($C_{43}H_{35}N_7O_4 \cdot 0.5CH_3C_6H_5$) Calcd.: C, 73.50; H, 5.17; N, 12.90 Found: C, 73.30; H, 5.37; N, 12.90.

Preparation 14

2-(N'-(m-(Trifluoromethylphenyl) ureidomethylcarbonylamino)benzophenone 6t

The titled compound is prepared by using the compound 3a prepared in Preparation 3 and m-(trifluoromethyl) phenylisocyanate In the same manner as Preparation 5. Yield 74%, Mp. 177°–178° C.

NMR (CDCl$_3$) δ: 4.15 (2H,s), 5.97–6.32 (1H,br.s), 7.30–7.73 (13H,m), 8.53 (1H,d,J=8.6 Hz), 11.27 (1H,s)

Preparation 15

2-(N'-(m-Chlorophenyl) ureidomethylcarbonylamino)benzophenone 6u

A solution of m-chlorophenylisocyanate (756 mg, 4.92 mmol) in tetrahydrofuran (8 ml) is added to a solution of the salt 3a (1.341 g, 4 mmol) prepared in Preparation 3 in tetrahydrofuran (50 ml). Triethylamine (1.67 µl, 12 mmol) is added at 0 ° C., and the mixture is stirred at 0° C. for 30 minutes and then at room temperature overnight. Water and then 10% hydrochloric acid are added, and the mixture is extracted with ethyl acetate. The extract is washed with water, dried (sodium sulfate), and distilled under reduced pressure to remove the solvent. The residue is recrystallized from dichloromethane/diisopropylalcohol to obtain the objective compound 6u (1.43 g; yield 73%).

IR $v_{max}$ (KBr): 1691, 1639, 1593, 1556, 1523 cm$^{-1}$.

NMR(CDCl$_3$) δ:4.08 (2H,s), 6.90–7.33 (5H,m), 7.40–7.73 (8H,m), 8.54 (1H,d,J=8.2 Hz), 11.21 (1H,s).

Preparation 16

2-(N'-(m-Bromophenyl) ureidomethylcarbonylamino)benzophenone 6v

A solution of the compound 3a (1.341 g, 4 mmol) prepared in Preparation 3 in tetrahydrofuran (10 ml) is added under ice cooling to a solution of m-bromoisocyanate which is prepared according to the method described in EP-508796-A1 from a solution of m-bromoaniline (846 mg, 4.92 mmol), triphosgene (551 mg, 1.72 mmol) and triethylamine (960 µl, 6.9 mmol) in tetrahydrofuran (50 ml). In addition, triethylamine (558 µl, 4 mmol) is added and treated in a manner similar to that described in Preparation 5 to prepare the compound 6v (1.45 g, yield 68%).

IR $v_{max}$ (KBr): 1682, 1638, 1590, 1554, 1523 cm$^{-1}$

NMR (CDCl$_3$+CD$_3$OD) δ: 4.10 (2H,d,J=5.7 Hz), 6.11 (1H,br.s), 6.99–7.30 (5H,m), 7.41–7.70 (8H,m), 8.54 (1H, d,J=8.4 Hz), 11.23 (1H,s)

Preparation 17

2-(N'-(m-Cyanophenyl)ureidomethylcarbonylamino) benzophenone 6w

A solution of the compound 3a (1.341 g, 4 mmol) prepared in Preparation 3 in tetrahydrofuran (10 ml) is added under ice cooling to a solution of m-bromoisocyanate which is prepared according to the method described in EP-508796-A1 from a solution of m-cyanoaniline (581 mg, 4.92 mmol), triphosgene (551 mg, 1.72 mmol) and triethylamine (960 µl, 6.9 mmol) in tetrahydrofuran (50 ml). In addition, triethylamine (558 µl, 4 mmol) is added and treated as in a manner similar to that described in Preparation 5 to prepare the compound 6w (1.4 g, yield 88%).

IR ν$_{max}$(KBr): 2230, 1686, 1638, 1603, 1589, 1558, 1522 cm$^{-1}$.

NMR (CDCl$_3$+CD$_3$OD) δ: 4.09 (2H,d,J=5.7 Hz), 7.09–7.72 (13H,m), 8.53 (1H,d,J=8.7 Hz), 11.22 (1H,s).

Preparation 18

2-(N'-(m-Methoxyphenyl)ureidomethylcarbonylamino)benzophenone 6x

A solution of m-methoxyphenylisocyanate (734 mg, 4.92 mmol) in tetrahydrofuran (8 ml) is added to a solution of the salt 3a (1.341 g, 4 mmol) prepared in Preparation 3 in tetrahydrofuran (50 ml). Triethylamine (558 µl, 4 mmol) is added at 0° C., and the mixture is stirred at 0°0 C. for 30 minutes and then at room temperature overnight. Water and then 10% hydrochloric acid are added, and the mixture is extracted with ethyl acetate. The extract is washed with water, dried (sodium sulfate), and distilled under reduced pressure to remove the solvent. The residue is recrystallized from dichloromethane/diisopropylether to obtain the objective compound 6x (1.29 g, 80%).

IR ν$_{max}$(KBr): 1693, 1640, 1619, 1606, 1591, 1560, 1515 cm$^{-1}$.

NMR (CDCl$_3$) δ: 3.68 (3H,s), 4.08 (2H,d,J=2.9 Hz), 5.99 (1H,d,J=5.8 Hz),6.56 (1H,dd,J=8.0, 1.8 Hz), 6.79 (1H, dd,J= 7.4, 1.0 Hz), 7.00–7.16 (3H,m), 7.37–7.69 (8H,m), 8.55 (1H,d,J=7.8 Hz), 11.27 (1H,s).

Preparation 19

2-(N'-(p-Chlorophenyl)ureidomethylcarbonylamino)benzophenone 6y

A solution of p-chlorophenylisocyanate (756 mg, 4.92 mmol) in tetrahydrofuran (8 ml) is added to a solution of the salt 3a (1.341 g, 4 mmol) prepared in Preparation 3 in tetrahydrofuran (50 ml). Triethylamine (558 µl, 4 mmol) is added at 0° C., and the mixture is stirred at 0° C. for 30 minutes, and then at room temperature overnight. Water and then 10% hydrochloric acid are added, and the mixture is extracted with ethyl acetate. The extract is washed with water, dried (sodium sulfate), and distilled under reduced pressure to remove solvent. The residue is recrystallized from dichloromethane/diisopropylether to obtain the objective compound 6y (1.48 g, 76%).

IR ν$_{max}$ (KBr): 1686, 1636, 1591, 1558, 1522 cm$^{-1}$.

NMR (CDCl$_3$+CD3OD) δ: 4.06 (2H,d,J=5.7 Hz), 6.31 (1H,t,J=6.0 Hz), 7.11–7.70 (13H,m), 8.52 (1H,d,J=7.5 Hz).

Preparation 20

2-(N'-(p-Tolyl)ureidomethylcarbonylamino)benzophenone 6z

A solution of p-tolylisocyanate (655 mg, 4.92 mmol) in tetrahydrofuran (8 ml) is added to a solution of the salt 3a (1.341 g, 4 mmol) prepared in Preparation 3 in tetrahydrofuran (50 ml). Triethylamine (558 µl, 4 mmol) is added at 0° C., and the mixture is stirred at 0° C. for 30 minutes, and then at room temperature overnight. Water and then 10% hydrochloric acid are added, and the mixture is extracted with ethyl acetate. The extract is washed with water, dried (sodium sulfate), and then the solvent is distilled off under reduced pressure. The residue is recrystallized from dichloromethane/diisopropylether to obtain the objective compound 6z (1.31 1 g, 85%).

IR ν$_{max}$(KBr): 1685, 1639, 1604, 1593, 1555, 1519 cm$^{-1}$.

NMR (CDCl$_3$) δ: 2.27 (3H,s), 4.07 (2H,d,J=6.0 Hz), 5.93 (1H,br.s), 7.0–7.29 (6H,m), 7.43–7.68 (7H,m), 8.65 (1H,d, J=8.4 Hz), 11.22 (1H,s).

Preparation 21

2-(N'-Phenylureidomethylcarbonylamino)benzophenone 6aa

A solution of phenylisocyanate (440 mg, 3.69 mmol) in tetrahydrofuran (8 ml) is added to a solution of the salt 3a (1.005 g, 3 mmol) prepared in Preparation 3 in tetrahydrofuran (50 ml). Triethylamine (911 mg, 9 mmol) is added at 0° C., and the mixture is stirred at 0° C. for 30 minutes, and then at room temperature overnight. Water and then 10% hydrochloric acid are added, and the mixture is extracted with ethyl acetate. The extract is washed with water, dried (sodium sulfate), and then the solvent is distilled off under reduced pressure. The residue is recrystallized from dichloromethane/diisopropylether to obtain the objective compound 6aa (750 mg, 67%).

IR Ξ$_{max}$(KBr): 1685, 1638, 1595, 1583, 1556, 1523 cm$^{-1}$.

NMR (CDCl$_3$+CD3OD) δ: 4.07 (2H,s), 6.93–7.70 (14H, m), 8.54 (1H,d,J=8.4 Hz), 11.22 (1H,s).

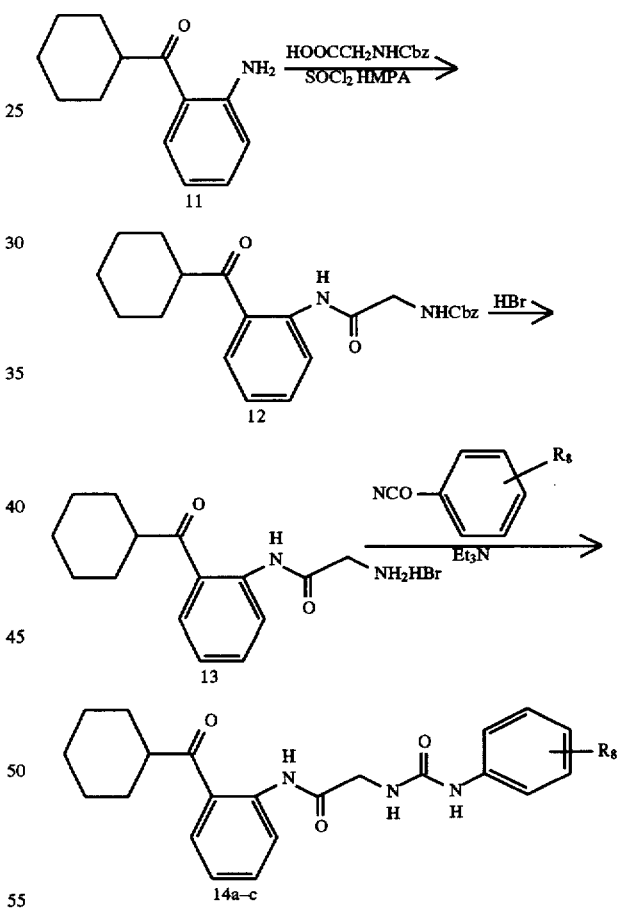

R$_8$ = a: —CH$_3$   b: —CF$_3$   c: —COOCH$_2$CH=CH$_2$

Preparation 22

Cyclohexyl-(2-(benzyloxycarbonylaminomethylcarbamoyl)phenyl) ketone 121

According to the method described in Preparation 1, the titled compound is synthesized by using cyclohexyl-(2-aminophenyl)ketone 11 which described in the literature [M. S. Chambers, S. C. Hobbs, S. R. Fletcher, V. G. Matassa, P. J. Mitchell, A. P. Watt, R. Baker, S. B. Freedman, S. Patel and A. J. Smith, Bioorg. Med. Chem. Lett., 3, 1919 (1993)].
Mp. 152°–155° C.

IR $v_{max}$(KBr): 3324, 1669, 1694, 1641, 1602, 1582, 1517 cm$^{-1}$.

NMR (CDCl$_3$) δ: 1.13–1.61 (5H,m), 1.69–1.94 (5H,m), 3.31 (1H,m), 4.09 (1H,d,J=5.6 Hz), 5.20 (2H,s), 5.49 (1H, m), 7.14 (1H,t,J=8.2 Hz), 7.20–7.48 (5H,m), 7.55 (1H,t,J=8.2Hz), 7.93 (1H,d,J=8.0Hz), 8.72 (1H,d,J=8.6 Hz).

Elemental analysis (C$_{23}$H$_{26}$N$_2$O$_4$0.2H$_2$O) Calcd.: C, 69.40; H, 6.68; N, 7.04 Found: C, 69.42; H, 6.58; N, 7.06.

Preparation 23

Cyclohexyl-(2-(aminomethylcarbamoyl)phenyl) ketone hydrobromide 13

According to the method described in Preparation 3, the titled compound is synthesized by using the compound 12 obtained in the above preparation.

Mp. 193°–196° C.

IR $v_{max}$(KBr): 3432, 1702, 1645, 1605, 1588, 1533 cm$^{-1}$.

Elemental analysis (C$_{15}$H$_{21}$BrN$_2$O$_2$0.4H$_2$O) Calcd.: C, 51.70; H, 6.31; Br, 22.93; N, 8.04 Found: C, 51.86; H, 6.05; Br, 22.86; N, 8.04.

Preparation 24

Cyclohexyl-(2-(N'-(m-tolyl)ureidomethylcarbamoyl) phenyl)ketone 14a

According to the method described in Preparation 5, the titled compound is synthesized by using cyclohexyl-(2-(aminomethylcarbamoyl)phenyl)ketone hydrobromide 13 and m-tolylisocyanate. Mp. 192°–193° C.

IR $v_{max}$(KBr): 3328, 1669, 1644, 1594, 1583, 1559, 1518 cm$^{-1}$.

NMR (CDCl$_3$+CD$_3$OD) δ: 1.05–1.52 (5H,m), 1.62–1.89 (5H,m), 2.32 (3H, s), 4.02 (2H,s), 6.85 (1H,d,J=6.0 Hz), 7.09–7.31 (4H,m), 7.55 (1H,m), 7.95 (1H,d,J=9.6 Hz), 8.65 (1H,d,J=8.6 Hz).

Elemental analysis (C$_{23}$H$_{27}$N$_2$O$_3$0.2H$_2$O) Calcd.: C, 69.57; H, 6.95; N, 10.58 Found: C, 69.37; H, 6.85; N, 10.53.

Preparation 25

Cyclohexyl-(2-(N'-(m-trifluoromethylphenyl) ureidomethylcarbamoyl)phenyl)ketone 14b According to the method described in Preparation 5, the titled compound is synthesized by using cyclohexyl-(2-(aminomethylcarbamoyl)phenyl)ketone hydrobromide 13 and m-(trifluoromethyl)phenylisocyanate. Mp. 207°–209° C.

IR $v_{max}$(KBr): 3343, 1661, 1605, 1581, 1565, 1524 cm$^{-1}$.

NMR (CDCl$_3$+CD$_3$OD) δ: 1.13 (1H,m), 1.23–1.48 (4H, m), 1.65–1.89 (5H,m), 3.28 (1H,m), 4.11 (2H,s), 7.10–7.41 (3H,m), 7.48–7.68 (2H,m),7.71 (1H,s) 7.90 (1H,d,J=8.2 Hz), 8.68 (1H,d,J=8.6 Hz).

Elemental analysis (C$_{23}$H$_{24}$F$_3$N$_3$O$_3$) Calcd.: C, 61.74; H, 5.41; N, 9.39 Found: C, 61.70; H, 5.45; N, 9.40.

Preparation 26

Cyclohexyl-(2-(N'-(m-(allyloxycarbonyl)phenyl) ureidomethylcarbamoyl)phenyl)ketone 14c According to the method described in Preparation 5, the titled compound is synthesized by using cyclohexyl-(2-(aminomethylcarbamoyl)phenyl)ketone hydrobromide (13) and m-(allyloxycarbonyl)phenylisocyanate. Mp. 188°–190° C.

IR $v_{max}$(KBr): 3335, 1720, 1660, 1582, 1557, 1524 cm$^{-1}$.

NMR (CDCl$_3$) δ: 1.03–1.52 (5H,m), 1.53–1.91 (5H,m), 3.23 (1H,m), 4.17 (2H,d,J=6.0 Hz), 4.79 (2H,d,J=5.8 Hz), 5.15–5.48 (2H,m), 5.82–6.13 (2H,m), 7.12 (1H,m), 7.31 (1H,t,J=13.5 Hz), 7.49 (1H,m), 7.70 (1H,m), 7.96 (1H,m), 8.69 (1H,d,J=9.4 Hz), 12.18 (1H,s).

Elemental analysis (C$_{26}$H$_{29}$N$_3$O$_5$) Calcd.: C, 67.37; H, 6.31; N, 9.07 Found: C, 67.53; H, 6.36; N, 9.12.

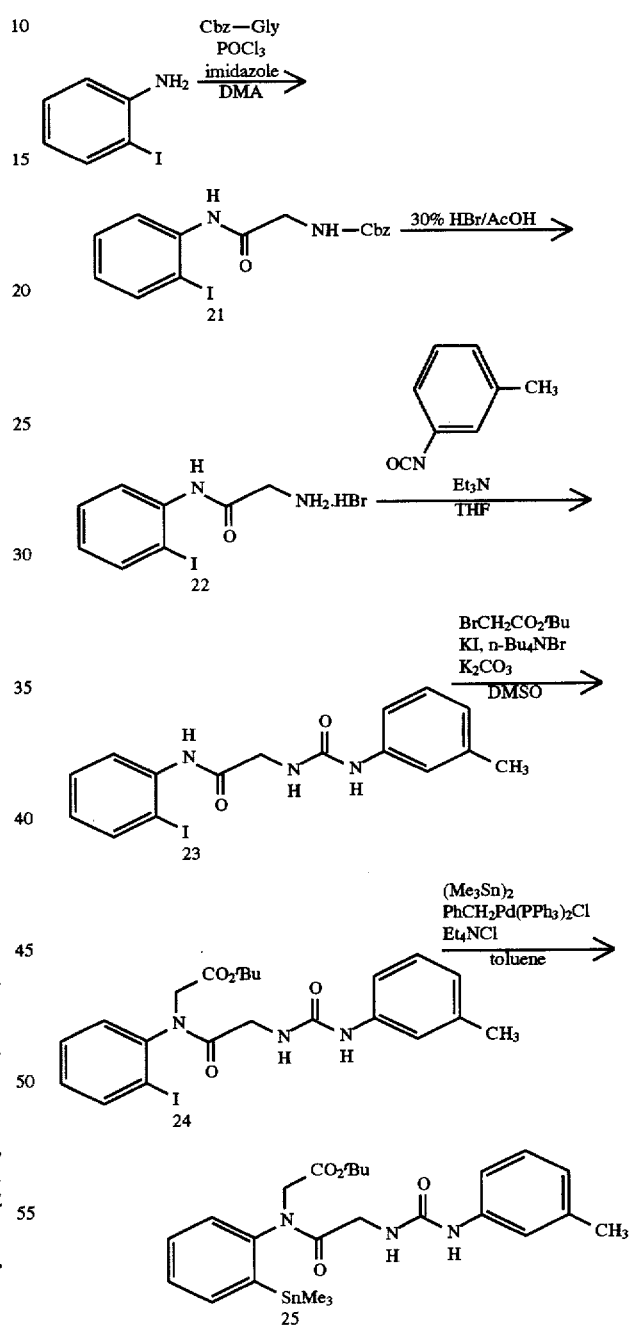

Preparation 27

N-(2-Iodophenyl)-2-(benzyloxycarbonylamino) acetamide 21

Phosphorus oxychloride (2.2 ml, 24 mmol), imidazole (2.7 g, 40 mmol), and N-benzyloxycarbonylglycine (5.0 g, 24 mmol) are added to dimethylacetamide (32 ml) under ice cooling and stirring. After stirring for 5 minutes, a solution of 2-iodoaniline (4.4 g, 20 mmol) in DMA (10 ml) is added dropwise. The reaction mixture is stirred at 50° C. for 3 hours. After allowing to cool, water and ethyl acetate are added to the reaction mixture, and a saturated aqueous solution of sodium hydrogencarbonate is added to make pH 9, and the aqueous phase is extracted twice with ethyl acetate. The organic layer is washed with a saturated saline, dried over anhydrous magnesium sulfate, and then concentrated. To the residue is added isopropylether (40 ml), and the precipitated solid is filtered off to obtain the objective compound (7.10 g). Yield 86%.

NMR (CDCl$_3$) δ: 4.06 (2H,d,J=5.8 Hz), 5.19 (2H,s), 5.44 (1H,brs), 6.80–6.91 (1H,m), 7.20–7.45 (6H,m), 7.76 (1H,d, J=8.0 Hz), 8.12 (1H,brs), 8.21 (1H,d,J=8.0 Hz).

Preparation 28

2-Amino-N-(2-iodophenyl)acetamide hydrobromide 22

According to the method described in Preparation 3, the titled compound (5.2 g) is synthesized by using the compound 21 (6.15 g). Yield 96%.

NMR (CDCl$_3$) δ: 3.94 (2H,s), 6.99–7.07 (1H,m), 7.37–7.45 (1H,m), 7.55 (1H,d,J=8.2 Hz), 7.92 (1H,d,J=8.0 Hz).

Preparation 29

N-(2-Iodophenyl)-2-(3-m-tolylureido)acetamide 23

According to the method described in Preparation 5, the titled compound (3.05 g) is synthesized by using the compound 2 (2.67 g) and m-tolylisocyanate (0.96 ml). Yield 100%.

NMR (DMSO-d$_6$) δ: 2.25 (3H,s), 3.95 (2H,d,J=5.4 Hz), 6.48–6.55 (1H,m), 6.73 (1H,d,J=6.8 Hz), 6.93–7.45 (5H,m), 7.61 (1H,dd,J=1.4 Hz,8.1 Hz), 7.88 (1H,dd,J=1.4 Hz, 8.0 Hz), 8.79 (1H,s), 9.45 (1H,s).

Preparation 30

Tert-butyl ((2-iodophenyl)-(2-(3-m-tolylureido)acetyl)amino)acetate 24

To a solution of N-(2-iodophenyl)-2-(3-m-tolylureido) acetamide (1.02 g, 2.5 mmol) in DMSO (5 ml) are added at room temperature potassium iodide (83 mg, 0.2 mmol), tetra-n-butylammonium bromide (81 mg, 0.1 mmol), t-butylbromoacetate (0.55 ml, 3.75 mmol) and potassium carbonate (1.04 g, 7.5 mmol), and stirred at room temperature for 2.25 hours. To the reaction mixture are added water and ethyl acetate, and the pH is adjusted to 2 with 2N hydrochloric acid. The aqueous layer is extracted twice with ethyl acetate. The organic layer is washed with 0.1N hydrochloric acid, water and saturated saline, dried over anhydrous magnesium sulfate, and then concentrated. To the residue is added isopropylether, and the precipitated solid is filtered off to obtain the objective compound (1.20 g). Yield 92%.

NMR (CDCl$_3$) δ: 1.45 (9H,s), 2.35 (3H,s), 3.49 (1H,d,J= 17.6 Hz), 3.65 (1H,dd,J=4.4 Hz, 17.6 Hz), 3.88 (1H,dd,J=4.4 Hz, 17.7 Hz), 4.92 (1H,d,J=17.6 Hz), 5.78–5.82 (1H,m), 6.59 (1H,brs), 6.87 (1H,d,J=7.4 Hz), 7.14–7.48 (5H,m), 7.69 (1H,d,J=7.8 Hz), 7.95 (1H,d,J=8.2 Hz).

Preparation 31 tert-Butyl((2-trimethylstannylphenyl)-(2-(3-m-tolylureido)acetyl)amino)acetate 25

To a solution of ((2-iodophenyl)-(2-(3-m-tolylureido) acetyl)amino)acetic acid tert-butyl ester (52 mg, 0.1 mmol)

in toluene (2 ml) is added at room temperature trans-benzylchlorobistriphenylphosphine palladium (3.8 mg, 5 μmol), tetraethylammonium chloride (3 mg, 20 μmol) and hexamethylditin (50 mg, 0.15 mmol), and stirred at 85° C. for 1 hour and at 100° C. for 30 minutes. To the reaction mixture is added ice-cooled water and stirred. The aqeous layer is extracted twice with ethyl acetate. The organic layer is washed with saturated saline, dried over anhydrous magnesium sulfate, and then concentrated. The residue is purified by silica gel column chromatography to obtain the objective compound (35 mg). Yield 64%.

NMR (CDCl$_3$) δ: 0.29 (9H,s), 1.43 (9H,s), 2.29 (3H,s), 3.56 (1H,d,J=16.8 Hz), 3.80 (2H,s), 4.79 (1H,d,J=16.8 Hz), 6.00 (1H,brs), 6.80–7.61 (9H,m).

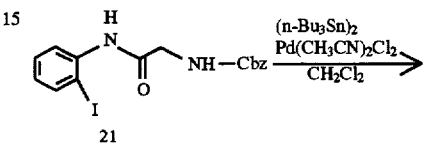

21

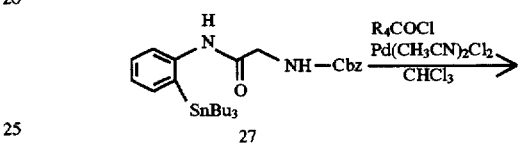

27

28a–e

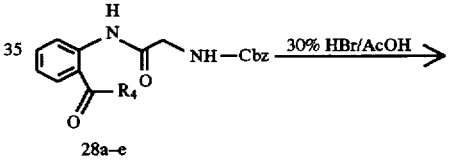

28a–e

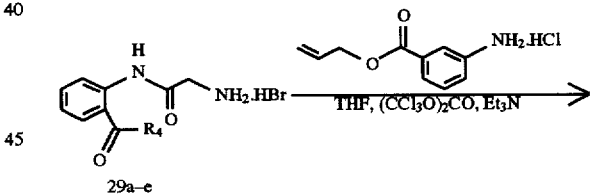

29a–e

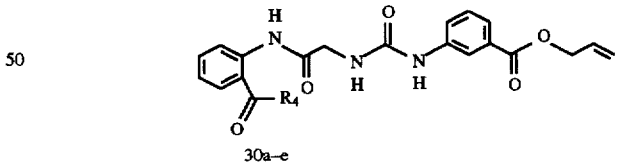

30a–e

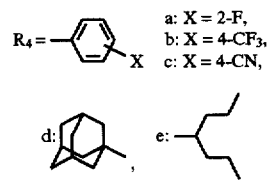

a: X = 2-F,
b: X = 4-CF$_3$,
c: X = 4-CN,

Preparation 32

N-(2-Tributylstannylphenyl)-2-(benzyloxycarbonylamino)acetamide 27

To a solution of N-(2-iodophenyl)-2-(benzyloxycarbonylamino)acetamide (compound 21) (4.1 g, 0.01 mol) in dichloromethane (80 ml) are added at room temperature dichlorobisacetonitrilepalladium (190 mg, 0.25 mmol) and hexabutyiditin (6.0 ml, 0.012 mol), and stirred at room temperature overnight. To the reaction mixture is added an aqueous solution of 50% potassium fluoride and stirred for 30 minutes, and the precipitate is removed by filteration. After this procedure is repeated once more, the organic layer is washed with saturated saline, dried over anhydrous magnesium sulfate, and then concentrated. The residue is purified by silica gel column chromatography to obtain the objective compound (4.4 g). Yield 77%.

NMR (CDCl$_3$) δ: 0.83–1.65 (27H,m), 4.03 (2H,d,J=5.6 Hz), 5.16 (2H,s), 5.40 (1H,brs), 7.10–7.48 (1H,m), 7.71 (1H,d,J=8.0 Hz).

Preparation 33

N-(2-(2-Fluorobenzoyl)phenyl)-2-(benzyloxycarbonylamino)acetamide 28a

To a solution of 2-fluorobenzoylchloride (208 μl, 1.74 mmol) in chloroform (20 ml) is added at room temperature dichlorobisacetonitrile palladium (15 mg, 0.044 mmol). Then, a solution of N-(2-tributylstannylphenyl)-2-(benzyloxycarbonylamino)acetamide (1 g, 1.74 mmol) in chloroform (3 ml) is added and stirred at 50° C. for 35 minutes. Dichlorobisacetonitrile palladium (15 mg, 0.044 mmol) is added and the stirring continued for another 10 minutes. After allowing to cool, an aqueous solution of 50% potassium fluoride is added to the reaction mixture and stirred for 30 minutes. The precipitate is removed by filteration. After this procedure is repeated once more, the organic layer is washed with saturated saline, dried over anhydrous magnesium sulfate, and then concentrated. The residue is purified by silica gel column chromatography to obtain the objective compound (570 mg). Yield 80%.

NMR (CDCl$_3$) δ: 4.12 (2H,d,J=6.0 Hz), 5.19 (2H,s), 5.50 (1H,brs), 7.05–7.66 (7H,m), 8.74 (1H,d,J=8.2 Hz).

Preparation 34

N-(2-(4-Trifluoromethylbenzoyl)phenyl)-2-(benzyloxycarbonylamino)acetamide 28b According to the method used for synthesis of the compound 28a, the titled compound (592 mg) is synthesized by using tert-butyl((2-trimethylstannylphenyl)-(2-(3-m-tolylureido)acethyl)amino)acetate (1.0 g) and 4-trifluoromethylbenzoylchloride (364 mg). Yield 74%.

NMR (CDCl$_3$) δ: 4.10 (2H,d,J=6.0 Hz), 5.18 (2H,s), 5.50 (1H,brs), 7.08–7.67 (8H,m), 7.76 (4H,s), 8.68 (1H,d,J=8.2 Hz).

Preparation 35

N-(2-(4-Cyanobenzoyl)phenyl)-2-(benzyloxycarbonylamino)acetamide 28c

According to the method used for the synthesis of the compound 28a, the titled compound (551 mg) is synthesized by using tert-butyl((2-trimethylstannylphenyl)-(2-(3-m-tolylureido)acethyl)amino)acetate (1.0 g) and 4-cyanobenzoylchloride (289 mg). Yield 76%.

NMR (CDCl$_3$) δ: 4.09 (2H,d,J=6.0 Hz), 5.18 (2H,s), 5.50 (1H,brs), 7.08–7.69 (8H,m), 7.74 (2H,d,J=8.6 Hz), 7.80 (2H,d,J=8.6 Hz), 8.68 (1H,d,J=8.2 Hz).

Preparation 36

N-(2-(Adamantane-1-carbonyl)phenyl)-2-(benzyloxycarbonylamino)acetamide 28d

According to the method used for the synthesis of the compound 28a, the titled compound (110 mg) is synthesized by using tert-butyl((2-trimethylstannylphenyl)-(2-(3-motolylureido)acethyl)amino)acetate (2.5 g) and adamantane-1-carbonylchloride (866 mg). Yield 6%.

NMR (CDCl$_3$) δ: 1.72 (6H,s), 2.00 (6H,s), 2.06 (3H,s), 4.00 (2H,d,J=5.8 Hz), 5.20 (2H,s), 5.44 (1H,brs), 7.09–7.68 (8H,m), 8.28 (2H,d,J=8.7 Hz), 9.57 (1H,brs).

Preparation 37

N-(2-(1-Oxo-2-propylpentyl)phenyl)-2-(benzyloxycarbonylamino)acetamide 28e

According to the method used for the synthesis of the compound 28a, the titled compound (990 mg) is synthesized by using tert-butyl((2-trimethylstannylphenyl)-(2-(3-m-tolylureido)acethyl)amino)acetate (2.5 g) and 2-n-propyl-n-valeroylchloride (710 mg). Yield 55%.

NMR (CDCl$_3$) δ: 0.88 (6H,t,J=7.0 Hz), 1.16–1.84 (8H, m), 3.43–3.58 (1H,m), 4.10 (2H,d,J=5.4 Hz), 5.19 (2H,s), 5.44 (1H,brs), 7.10–7.62 (7H,m), 7.94 (1H,d,J=8.2 Hz), 8.73 (1H,d,J=8.2 Hz).

Preparation 38

2-Amino-N-(2-(2-fluorobenzoyl)phenyl)acetamide hydrobromide 29a

According to the method described in Preparation 3, the titled compound (432 mg) is synthesized by using the compound 28a (530 mg). Yield 94%.

NMR (CD$_3$OD) δ: 3.88 (2H,s), 6.99–7.07 (1H,m), 7.18–7.70 (7H,m), 8.20 (1H,d,J=8.0 Hz).

Preparation 39

2-Amino-N-(2-(4-trifluoromethylbenzoyl)phenyl) acetamide hydrobromide 29b

According to the method described in Preparation 3, the titled compound (450 mg) is synthesized by using the compound 28b (550 mg). Yield 93%.

NMR (CD$_3$OD) δ: 3.90 (2H,s), 7.19–7.67 (3H,m), 7.76 (2H,d,J=8.0 Hz), 7.86 (2H,d,J=8.0 Hz), 8.19 (1H,d,J=8.2 Hz).

Preparation 40

2-Amino-N-(2-(4-cyanobenzoyl)phenyl)acetamide hydrobromide 29c

According to the method described in Preparation 3, the titled compound (484 mg) is synthesized by using the compound 28c (542 mg). Yield 100%.

NMR (CD$_3$OD) δ: 3.76 (2H,s), 7.29–7.88 (3H,m), 7.89 (4H,s).

Preparation 41

2-Amino-N-(2-(adamantane-1-carbonyl)phenyl) acetamide hydrobromide 29d

According to the method described in Preparation 3, the titled compound (61 mg) is synthesized by using the compound 28d (100 mg). Yield 69%.

NMR (CD$_3$OD) δ: 1.75 (6H,s), 1.97 (6H,s), 2.02 (3H,s), 3.83 (2H,s), 7.22 –7.5 (4H,m).

Preparation 42

2-Amino-N-(2-(1-oxo-2-propylpentyl)phenyl) acetamide hydrobromide 29e

According to the method described in Preparation 3, the titled compound (522 mg) is synthesized by using compound 28e (770 mg). Yield 78%.

NMR (CD₃OD) δ: 0.88 (6H,t,J=7.2 Hz), 1.19–1.83(8H, m), 3.58–3.73 (1H,m), 4.00 (2H,s), 7.26–7.69 (2H,m), 8.14 (1H,dd,J=1.6 Hz, 8.2 Hz), 8.56 (1H,d,J=8.2 Hz).

Preparation 43

Allyl 3-(3-(2-(2-fluorobenzoyl)phenylcarbamoylmethyl)ureido)benzoate 30a

According to the method described in Preparation 5, the titled compound (391 mg) is synthesized by using as starting materials the compound 29a (432 mg) and the isocyanate which is prepared from allyl 3-aminobenzoate hydrochloride (261 mg) and triphosgene (145 mg). Yield 67%.

NMR (CDCl₃) δ: 4.19 (2H,d,J=5.4 Hz), 4.78 (2H,d,J=5.4 Hz), 5.21–5.44 (2H,m), 5.79–6.10 (2H,m), 7.03–7.94 (12H, m), 8.69 (1H,d,J=8.2 Hz).

Preparation 44

Allyl 3-(3-(2-(4-trifluoromethylbenzoyl)phenylcarbamoylmethyl)ureido)benzoate 30b According to the method described in Preparation 5, the titled compound (343 mg) is synthesized by using the compound 29b (450 mg) as a starting material. Yield 65%.

NMR (CDCl₃) δ: 4.14 (2H,d,J=5.7 Hz), 4.76 (2H,d,J=5.4 Hz), 5.22–5.41 (2H,m), 5.92–6.05 (2H,m), 7.06–7.76 (11H, m), 7.90 (1H,s), 8.57 (1H,d,J=84 Hz), 11.31 (1H,s).

Preparation 45

Allyl 3-(3-(2-(4-cyanobenzoyl)phenylcarbamoylmethyl)ureido)benzoate 30c

According to the method described in Preparation 5, the titled compound (438 mg) is synthesized by using the compound 29c (472 mg) as a starting material. Yield 69%.

NMR (CDCl₃) δ: 4.13 (2H,d,J=5.7 Hz), 4.79 (2H,d,J=5.4 Hz), 5.22–5.44 (2H,m), 5.79–6.12 (2H,m), 7.06–7.80 (11H, m), 7.89 (1H,s), 8.58 (1H,d,J=8.4 Hz).

Preparation 46

Allyl 3-(3-(2-(adamantane-1-carbonyl)phenylcarbamoylmethyl)ureido)benzoate 30d

According to the method described in Preparation 5, the titled compound (44 mg) is synthesized by using the compound 29d (61 mg) as a starting material. Yield 55%.

NMR (CDCl₃) δ: 1.63 (9H,s), 1.90 (6H,s), 4.05 (2H,d,J=5.8 Hz), 4.81 (2H,d,J=6.0 Hz), 5.23–5.45 (2H,m), 5.81–6.12 (2H,m), 7.07–7.98 (12H,m), 8.21 (1H,d,J=8.0 Hz).

Preparation 47

Allyl 3-(3-(2-(1-oxo-2-propylpentyl)phenylcarbamoylmethyl)ureido)benzoate 30e.

According to the method described in Preparation 5, the titled compound (321 mg) is synthesized by using the compound 29e (522 mg) as a starting material. Yield 43%.

NMR (CDCl₃) δ: 0.83 (6H,t,J=7.0 Hz), 1.12–1.78 (8H, m), 3.41–3.56 (1H,m), 5.22–5.45 (2H,m), 5.84–6.12 (2H, m), 7.10–7.98 (12H,m), 8.71 (1H,d,J=8.4 Hz).

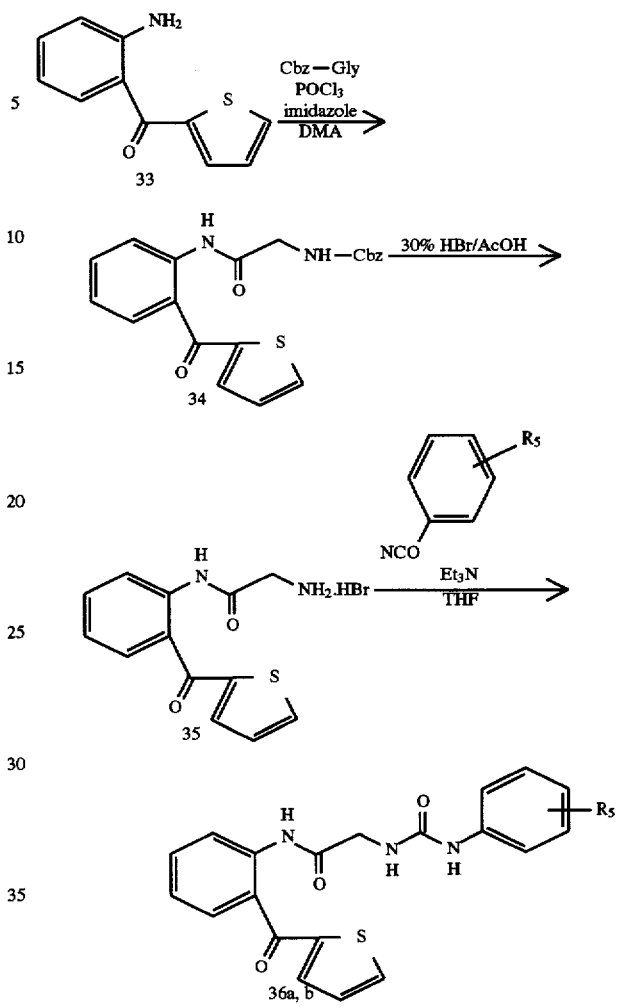

Preparation 48

N-(2-(Thiophene-2-carbonyl)phenyl)-2-(benzyloxycarbonylamino)acetamide 341

According to the method for the synthesis of the compound 21, the titled compound was prepared using the compound 33.

Mp. 115°–116.5° C.

IR $\nu_{max}$ (KBr):3274,1716,1671,1619,1601,1579,1514 cm⁻¹.

NMR (CDCl₃) δ: 4.04 (2H,d,J=6.0 Hz), 5.18 (2H,s), 5.44–5.60 (1H,m), 7.15–7.50 (7H,m), 7.56–7.62 (2H,m), 7.75 (1H,dd,J=4.8 Hz, 0.9 Hz), 7.84 (1H,dd,J=7.8 Hz, 1.2 Hz), 8.55 (1H,d,J=8.1 Hz), 10.80 (1H,s).

Elemental Analysis (C₂₁H₁₈N₂O₄S) Calcd.: C, 63.95; H, 4.60; N, 7.10; S, 8.13 Found: C, 63.97; H, 4.70; N, 7.17; S, 8.03.

Preparation 49

2-Amino-N-(2-(thiophene-2-carbonyl)phenyl)acetamide hydrobromide 35

According to the method described in Preparation 3, the titled compound was prepared using the compound 34.

NMR (CDCl₃+CD₃OD) δ:5.31 (2H,s), 7.08–7.24 (2H,m), 7.44–7.54 (2H,m), 7.66 (1H,d,J=7.8 Hz), 7.74 (1H,dd,J=5.0 Hz, 1.2 Hz), 8.09 (1H,dd,J=8.2 Hz, 1.8 Hz), 10.35 (1H,s).

Preparation 50

N-(2-(Thiophene-2-carbonyl)phenyl)-2-(-m-tolylureido)acetamide 36a

According to the method described in Preparation 15, the titled compound was prepared using the compound 35. Mp. 208°–210° C.

IR $v_{max}$ (KBr): 3337,1687,1638,1609,1580,1563,1518 cm$^{-1}$.

NMR (DMSO-d$_6$) δ:2.22 (3H,s), 3.79 (2H,d,J=5.2 Hz), 6.50 (2H,t,J=10.8 Hz), 6.72 (1H,dd,J=2.6 Hz, 0.8 Hz), 7.04–7.32 (5H,m), 7.52–7.70 (3H,m), 7.94 (1H,d,J=8.2 Hz), 8.04–8.10 (1H,m), 8.76 (1H,s), 10.33 (1H,s).

Elemental Analysis (C$_{21}$H$_{19}$N$_3$O$_3$S) Calcd.: C, 64.11; H, 4.87; N, 10.68; S, 8.15 Found: C, 64.09; H, 4.92; N, 10.74; S, 8.05.

Preparation 51

Allyl 3-(3-(2-(thiophene-2-carbonyl)phenylcarbamoylmethyl)ureido)benzoate 36b According to the method described in Preparation 15, the titled compound was prepared using the compound 35. Mp. 140°–141° C.

IR $v_{max}$ (KBr): 3284,1714,1689,1648,1618,1584,1560, 1520 cm$^{-1}$.

NMR (CDCl$_3$) δ:4.09 (2H,d,J=5.6 Hz), 4.77 (2H,dt,J=5.4 Hz, 1.4Hz), 5.25 (1H,dd,J=10.2 Hz, 1.2 Hz), 5.37 (1H,dd, J=17.2 Hz, 1.4 Hz), 5.85–6.10 (2H,m), 7.05–7.30 (3H,m), 7.50–7.80 (7H,m), 7.91 (1H,m), 8.45(1H,dd J=8.2 Hz, 0.8 Hz), 10.71 (1H,s).

Elemental Analysis (C$_{24}$H$_{21}$N$_2$O$_5$S) Calcd.: C, 62.19; H, 4.57; N, 9.07; S, 6.92 Found: C, 62.13; H, 4.74; N, 9.00; S, 6.81.

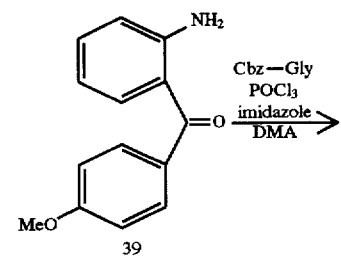

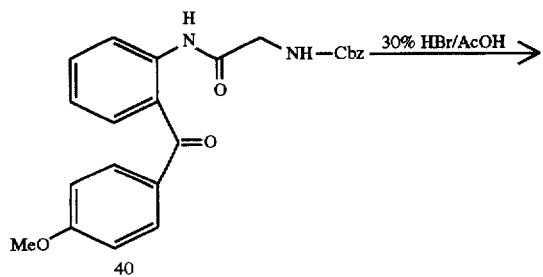

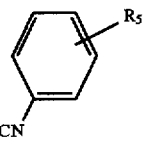

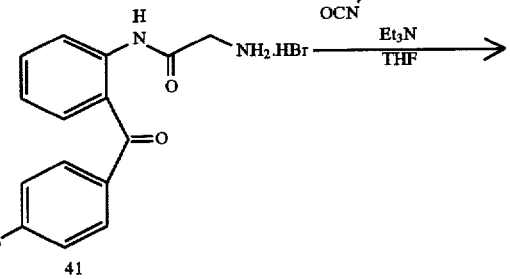

Preparation 52

N-(2-(4-Methoxybenzoyl)phenyl)-2-(benzyloxycarbonylamino)acetamide 40

According to the method for the synthesis of compound 21, the titled compound was prepared was prepared using the compound 39.

Mp. 97°–98° C.

IR $v_{max}$ (KBr): 3342, 1687, 1624, 1583, 1513 cm$^{-1}$.

NMR (CDCl$_3$) δ:3.89 (3H,s), 4.05 (2H,d,J=6.0 Hz), 5.16 (2H,s), 5.55–5.58 (1H,m), 6.93–6.98 (2H,m), 7.09–7.14 (1H,m), 7.30–7.42 (5H,m),7.52–7.57 (2H,m), 7.69–7.72 (2H,m), 8.55 (1H,d,J=7.5Hz), 11.06 (1H,s).

Elemental Analysis (C$_{24}$H$_{22}$N$_2$O$_5$) Calcd.: C, 68.88; H, 5.30; N, 6.69 Found: C, 68.91; H, 5.34; N, 6.72.

Preparation 53

2-Amino-N-(2-(4-methoxybenzoyl)phenyl)acetamide hydrobromide 41

According to the method described in Preparation 3, the titled compound was prepared using the compound 42.

NMR (D$_2$O) δ:3.67 (2H,s), 3.92 (3H,s), 7.05–7.10 (2H, m), 7.40–7.78(6H,m)

Preparation 54

N-(2-(4-Methoxybenzoyl)phenyl)-2-(3-m-tolylureido)acetamide 42a

According to the method described in Preparation 15, the titled compound was prepared using the compound 41.

Mp. amorphous powder.

IR $v_{max}$(KBr): 3313, 2925, 2855, 1654, 1597, 1581, 1559 cm$^{-1}$.

NMR(CDCl$_3$) δ:2.18 (3H,s), 3.84 (3H,s), 4.02 (2H,d,J= 6.0 Hz), 6.10(1H,t,J=6.0 Hz), 6.75–6.90 (3H,m), 7.03–7.10 (4H,m), 7.45–7.68 (5H,m), 8.44 (1H,d,J=7.2 Hz), 10.94 (1H,s).

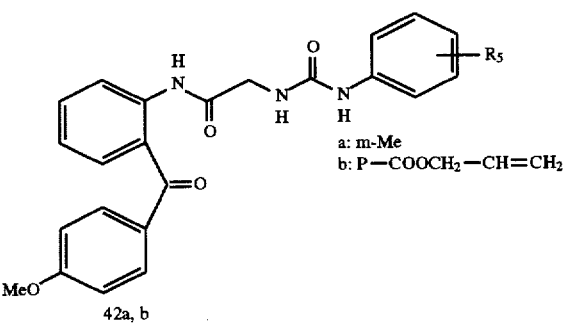

Preparation 55

Allyl 3-(3-(2-(4-methoxybenzoyl)phenylcarbamoylmethyl)ureido)benzoate 42b

According to the method described in Preparation 15, the titled compound was prepared using the compound 41.

Mp. 167°–169° C.

IR $v_{max}$ (KBr): 3371,3275,1715,1690,1641,1591,1566, 1525 cm$^{-1}$.

NMR (CDCl$_3$) δ:3.86 (3H,s), 4.07 (2H,d,J=6.0 Hz), 4.78 (2H,dt,J=5.7 Hz, 1.2 Hz), 5.24–5.28 (1H,m), 5.35–5.41 (1H,m), 5.94–6.07 (1H,m), 6.43 (1H,t,J=5.4 Hz), 6.87–6.95 (2H,m), 7.07–7.12 (1H,m), 7.23–7.29 (1H,m), 7.49–7.55 (2H,m), 7.62–7.67 (3H,m), 7.75–7.78 (1H,m),7.90–7.91 (1H,m), 8.35 (1H,s), 8.51 (1H,d,J=7.5 Hz), 10.95 (1H,s).

Elemental Analysis (C$_{27}$H$_{25}$N$_3$O$_6$) Calcd.: C, 66.52; H, 5.17; N, 8.62

Found :C, 66.37; H, 5.29; N, 8.58.

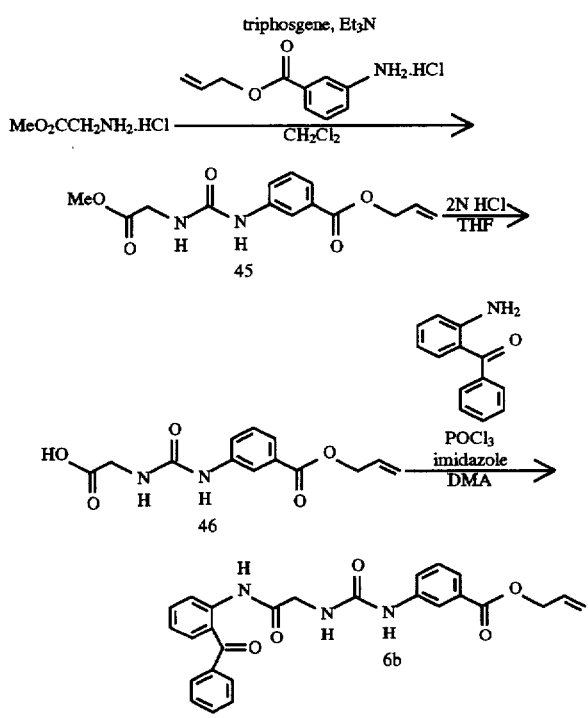

Preparation 56

Synthesis of 2-(benzyloxycarbonylglycylamino)benzophenone (compound 6b) by another method I (1) Allyl 3-(methoxycarbonylmethylureido)benzoate 45

A suspension of triphosgene (2.5 g, 8.42 mmol) and allyl 3-aminobenzoate hydrochloride (4.0 g, 18.7 mmol) in dichloromethane (80 ml) is cooled to –20° C. and triethylamine (9.64 ml, 69.2 mmol) is added dropwise thereto. The mixture is strirred for 30 minutes. To the mixture is added glycine methyl ester hydrochloride (2.82 g, 22.44 mmol). Then, triethylamine (3.75 ml, 18.7 mmol) is added dropwise, followed by stirring at –20° C. for 2.5 hours. Ice-cooled water is added to the reaction solution and, after stirring, the aqueous layer is extracted twice with ethyl acetate. The organic layer is washed with saturated brine, dried over anhydrous magnesium sulfate and concentrated to obtain the objective compound (5.27 g). Yield 96%.

NMR (CDCl$_3$) δ:3.76 (3H,s), 4.08 (2H,s), 4.80 (2H,d,J= 5.5 Hz), 5.23–5.45 (2H,m), 5.92–6.12 (2H,m), 7.28–7.38 (1H,m), 7.67–7.90 (3H,m).

(2) (3-Allyloxycarbonylphenyl)ureidoacetic acid 46

To a solution of allyl 3-(methoxycarbonylmethylureido) benzoate (5.27 g, 18.7 mmol) in THF (27 ml) is added 2N hydrochloric acid (37.4 ml), and the mixture is refluxed with stirring for 2.5 hours. After allowing to cool, water and an aqueous saturated sodium bicarbonate solution are added to the reaction solution to adjust the pH of the aqueous layer to 8, which is then extracted with ethyl acetate. Concentrated hydrochloric acid is added to the aqueous layer to adjust the pH to 1, followed by extraction with ethyl acetate. The organic layer is washed with saturated brine, dried over anhydrous magnesium sulfate and concentrated. The residue is crystallized from toluene to obtain the objective compound (3.66 g). Yield 70%.

NMR (DMSO-d$_6$) δ:3.80 (2H,d,J=5.9 Hz), 4.79 (2H,d,J= 5.4 Hz), 5.24–5.47 (2H,m), 5.95–6.16 (2H,m), 6.41 (1H,t, J=5.9 Hz), 7.39 (1H,t,J=7.8 Hz), 7.50–7.65 (2H,m), 8.14 (1H,s), 9.08 (1H,s).

(3) 2-(Allyloxycarbonylphenylglycylamino)benzophenone 6b

To DMA (40 ml) are added phosphorous oxychloride (2.07 ml, 22.64 mmol) and imidazole (1.54 g, 22.64 mmol) with stirring and under cooling. A solution of (3-allyloxycarbonylphenyl)ureidoacetic acid (3.0 g, 10.78 mmol) in dimethylacetamide (10 ml) is added dropwise and the mixture is stirred for 10 minutes under ice-cooling. Then, a solution of 2-aminobenzophenone (2.34 g, 11.86 mmol) in DMA (5 ml) is added dropwise. The reaction solution is stirred at 50° C. for 5.5 hours. After allowing to cool, water and ethyl acetate are added to the reaction solution to adjust the pH to 9 with an aqueous saturated sodium bicarbonate solution, and the aqueous layer is extracted with ethyl acetate. The organic layer is washed with saturated brine, dried over anhydrous magnesium sulfate and concentrated. The residue is crystallized from toluene to obtain the objective compound (3.63 g). Yield 74%.

Preparation 57

Synthesis of 2-(allyloxycarbonylphenylglycylamino) benzophenone (compound 6b) by another method II (1) Under a nitrogen flow, to a suspension of N,N'-carbonyldiimidazole (5.69 g, 1.5 eq.) in DMF (25 ml) is added dropwise a solution of a starting material (5.00 g) in DMF (20 ml) at 5° C. or below under ice-cooling over 30 minutes. After stirring at the same temperature for 1 hour and 30 minutes, glycine methyl ester hydrochloride (3.53 g, 1.2 eq.) is added, and the mixture is stirred at room temperature for 2 hours.

This reaction solution is poured into a mixture of 1N hydrochloric acid (50 ml) and ethyl acetate (50 ml) and then partitioned. The organic layer is washed twice with water (25 ml) and the aqueous layer is extracted with ethyl acetate (25 ml). The organic layers are combined, dried over anhydrous sodium sulfate and concentrated under reduced pressure to obtain 6.55 g (95.8%) of a crystalline residue of the compound 45.

(2) Under a nitrogen flow, to a suspension of glycine (9.13 g, 1.3 eq.) in DMF (40 ml) is added dropwise trimethylsilyl chloride (16.0 ml, 1.35 eq.) under ice-cooling over 6 minutes. The mixture is stirred at room temperature for 1.5 hours, and at 40° C. for 0.5 hours. Then, the mixture is stirred under ice-cooling to obtain an O-silylglycine reaction solution.

Under a nitrogen flow, to a suspension of N,N'-carbonyldiimidazole (22.77 g, 1.5 eq.) in DMF (80 ml) is added dropwise a solution of a starting material (20.00 g) in DMF (60 ml) at 5° C. or below under ice-cooling over 10 minutes, and the mixture is washed with DMF (10 ml). After stirring at the same temperature for 1.5 hours, the above O-silylglycine reaction solution is added, which is followed by stirring at room temperature for 2 hours.

The reaction solution is poured into ethyl acetate (300 ml), ice-cooled water (200 ml), N—HCl (200 ml) and sodium chloride (60 g) and then partitioned. The organic layer is washed with water (200 ml), aqueous saturated sodium bicarbonate (200 ml), and aqueous saturated sodium bicarbonate (100 ml)+water (100 ml). The aqueous layer is reverse-extracted with ethyl acetate (200 ml) and then ethyl acetate (100 ml).

The sodium bicarbonate alkali layers are combined and ethyl acetate (260 ml) is added thereto. After the addition of concentrated hydrochloric acid (10 ml) dropwise with stirring, the mixture is partitioned. The organic layer is washed twice with aqueous 10% brine. The aqueous layer is reverse-extracted with ethyl acetate (130 ml). The organic layers are combined, dried over anhydrous sodium sulfate and concentrated under reduced pressure. After the addition of toluene (200 ml), the mixture is further concentrated under reduced pressure to give a slurry solution of the compound 46. After standing overnight, the solution is filtered and washed twice with toluene (20 ml) to obtain 21.7 g (83.3%) of a crystal of the compound 46. The compound 46 is trated in a manner similar to that described in Preparation 57 to obtain the compound 6b.

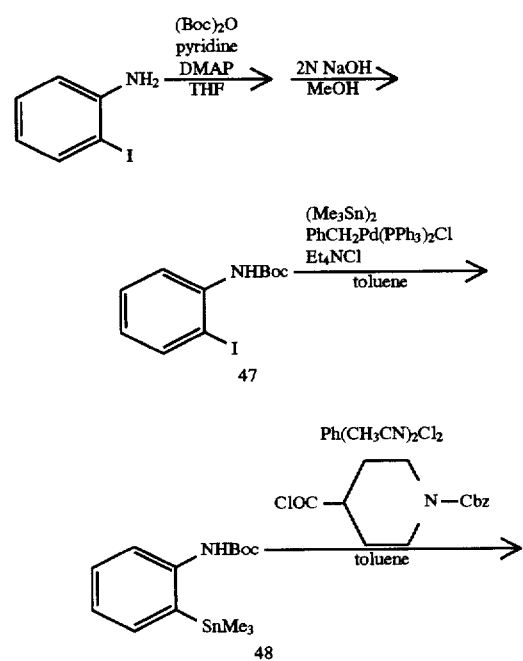

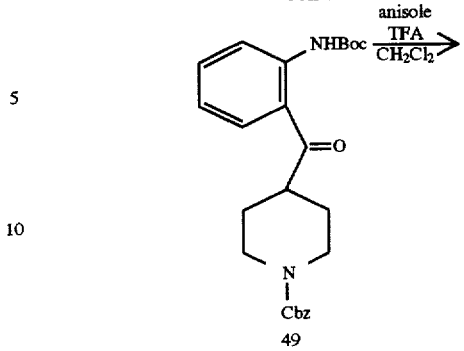

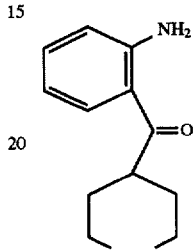

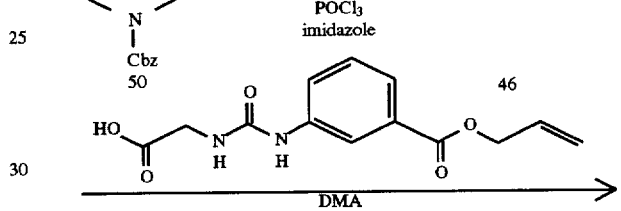

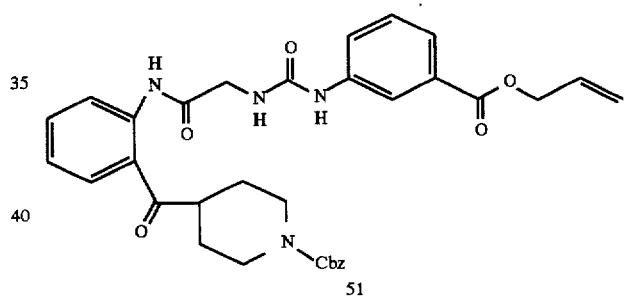

Preparation 58

N-tert-Butoxycarbonyl-2-iodoaniline 47

To a solution of iodoaniline (11.0 g, 0.05 mol) are added pyridine (10.1 mg, 0.10 mol) and dimethylaminopyridine (610 mg, 5 mmol) at room temperature. Di-tert-butyl carbonate (26.6 ml, 0.125 mol) is added dropwise and the mixture is refluxed with stirring for 6 hours. After allowing to cool, the reaction solution is diluted with ethyl acetate and, ice-cooled water is added. To the mixture is added 2N hydrochloric acid to adjust the pH to 1 and the aqueous layer is extracted twice with ethyl acetate. The organic layer is washed with saturated brine, dried over anhydrous magnesium sulfate and concentrated. The residue is dissolved in methanol (200 ml) and an aqueous 2N sodium hydroxide solution (50 ml) is added with stirring under ice-cooling.

After stirring at room temperature for 2 hours, methanol is distilled off under reduced pressure. The reaction solution is diluted with dichloromethane and, after adding ice-cooled water, 2N hydrochloric acid is added to adjust the pH to 1. The aqueous layer is extracted twice with ethyl acetate. The organic layer is washed with saturated brine, dried over anhydrous magnesium sulfate and concentrated. The residue is purified by subjecting to silica gel column chromatography to obtain the objective compound (8.54 g).

Yield 54%.

NMR (CDCl$_3$) δ:1.42 (9H,s), 6.71–6.81 (1H,m), 6.82 (1H,brs), 7.26–7.36 (1H,m), 7.75 (1H,dd,J=1.2 Hz,8.0 Hz), 8.05 (1H,dd,J=1.6 Hz,8.2 Hz).

Preparation 59

N-tert-Butoxycarbonyl-2-trimethylstannylaniline 48

To a solution of N-tert-butoxycarbonyl-2-iodoaniline (3.20 g, 0.01 mol) in toluene (65 ml) are added trans-benzylchlorobistriphenylphosphine palladium (380 mg, 5 μmol), tetraethylammonium chloride (330 mg, 20 μmol) and hexamethylditin (5.1 g, 0.015 mmol) at room temperature and the mixture is stirred at 95° C. for 2.5 hours. After allowing to cool, ice-cooled water is added to the reaction solution and the precipitate is removed by filtration. The aqueous layer is extracted with ethyl acetate. The organic layer is washed with saturated brine, dried over anhydrous magnesium sulfate and concentrated. The residue is purified by subjecting to silica gel column chromatography to obtain the objective compound (2.46 g). Yield 69%.

NMR (CDCl$_3$) δ:0.34 (9H,s), 1.51 (9H,s), 6.28 (1H,brs), 7.07–7.17(1H,m), 7.22–7.43 (2H,m), 7.52 (1H,d,J=8.6 Hz).

Preparation 60

2-(N-(Benzyloxycarbonyl)piperidine-4-carbonyl)-N'-tert-butoxycarbonylaniline 49

N-(benzyloxycarbonyl)piperidine-4-carboxylic acid (1.10 g, 4.18 mmol) is dissolved in thionyl chloride (1.23 ml) and the solution is refluxed with stirring for 20 minutes. Excess thionyl chloride is distilled off under reduced pressure and the residue is dissolved in toluene. To the solution is added dichlorobisacetonitrile palladium (73 mg, 0.209 mmol). Then, N-tert-butoxycarbonyl-2-trimethylstannylaniline (1.50 g, 4.18 mmol) is added, and the mixture is stirred at 55° C. for 45 minutes. After allowing to cool, ice-cooled water is added to the reaction solution and, after stirring, the aqueous layer is extracted twice with ethyl acetate. The organic layer is washed with saturated brine, dried over anhydrous magnesium sulfate and concentrated. The residue is purified by subjecting to silica gel column chromatography to obtain the objective compound (1.49 g). Yield 81%.

NMR (CDCl$_3$) δ:1.53 (9H,s), 1.63–1.95 (4H,m), 2.85–3.06 (2H,m), 3.37–3.58 (1H,m), 4.16–4.38 (2H,m), 5.15 (2H,s), 6.99–7.08 (1H,m),7.36 (5H,s), 7.48–7.57 (1H, m), 7.86 (1H,dd,J=1.2 Hz,8.2 Hz), 8.51 (1H,dd,J=1.0 Hz,8.2 Hz).

Preparation 61

2-(N-(Benzyloxycarbonyl)piperidine-4-carbonyl) aniline 50

To a solution of 2-(N-(benzyloxycarbonyl)piperidine-4-carbonyl)-N'-tert-butoxycarbonylaniline (1.30 g, 3.0 mmol) in methylene chloride (6.5 ml) is added anisole (2.0 ml) at room temperature. Then, trifluoroacetic acid (13.0 ml) is added dropwise with stirring under ice-cooling and the mixture is stirred at the same temperature for one hour. The reaction solution is diluted with ethyl acetate and, after adding ice-cooled water, the solution is neutralized with an aqueous saturated sodium bicarbonate solution. The aqueous layer is extracted twice with ethyl acetate. The organic layer is washed with saturated brine, dried over anhydrous magnesium sulfate and concentrated. The residue is purified by subjecting to silica gel column chromatography to obtain the objective compound (987 mg). Yield 99%.

NMR (CDCl$_3$) δ:1.69–1.96 (4H,m), 2.83–3.08 (2H,m), 3.35–3.53 (1H,m), 4.17–4.39 (2H,m), 5.15 (2H,s), 6.30 (2H,brs), 6.61–6.70 (2H,m),7.23–7.39 (1H,m), 7.36 (5H,s), 7.73 (1H,d,J=8.2 Hz).

Preparation 62

Allyl 3-(3-(2-(N-(benzyloxycarbonyl)piperidine-4-carbonyl)phenylcarbamoylmethyl)ureido)benzoate 51

According to the method for the synthesis of the compound 6b, the titled compound (780 mg) is prepared using 2-(N-(benzyloxycarbonyl)piperidine-4-carbonyl)aniline (677 mg) and 2-(benzyloxycarbonylglycilamino) benzophenone (compound 46) (556 mg) as starting materials. Yield 65%.

NMR (DMSO-d$_6$) δ:1.13–1.39 (2H,m), 1.54–1.79 (2H, m), 2.80–3.06 (2H,m), 3.52–3.69 (1H,m), 3.74–3.98 (2H, m), 3.88 (2H,d,J=6.0 Hz), 3.76 (2H,d,J=5.2 Hz), 5.06 (2H,s), 5.20–5.43 (2H,m), 5.90–6.13 (1H,m), 6.83 (1H,t,J=6.0 Hz), 7.18–7.68 (10H,m), 8.05 (1H,d,J=7.8 Hz), 8.15 (1H,s), 8.45 (1H,d,J=7.8 Hz), 9.28 (1H,s), 11.60 (1H,s).

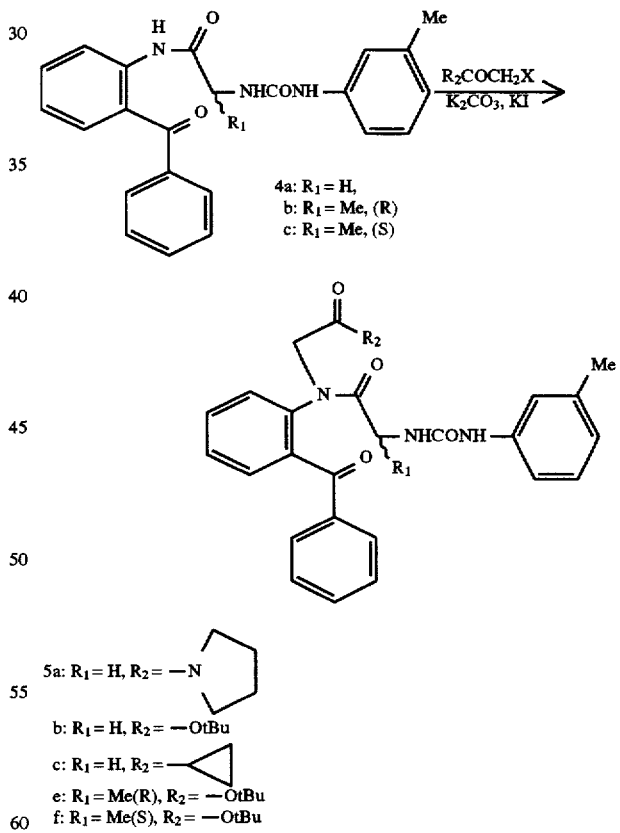

4a: R$_1$ = H,
b: R$_1$ = Me, (R)
c: R$_1$ = Me, (S)

5a: R$_1$ = H, R$_2$ = —N⟨ ⟩
b: R$_1$ = H, R$_2$ = —OtBu
c: R$_1$ = H, R$_2$ = —◁
e: R$_1$ = Me(R), R$_2$ = —OtBu
f: R$_1$ = Me(S), R$_2$ = —OtBu

EXAMPLE 1

2-(N-(Pyrrolidinocarbonylmethyl)-N-(N'-(m-tolyl) ureidomethylcarbonyl)amino)benzophenone 5a A solution of the amide (4a (300 mg) prepared in Preparation 5, bromoacetylpyrrolidine (17.35 mg), potassium carbonate (120 mg) and potassium iodide (10 mg) in dimethylformamide (5 ml) is stirred overnight. After pouring into water, the mixture is extracted with ethyl acetate. After the extract is washed with water and dried (over sodium sulfate), the solvent is distilled off under reduced pressure. The residue is recrystallized from acetonitrile. Yield 53%, Mp. 204°–205° C.

IR $v_{max}$ (KBr):3310, 1655, 1637, 1560 cm$^{-1}$.

NMR (CDCl$_3$) δ:1.81 (4H,m), 2.28 (3H,s), 3.34 (4H,m), 3.78 (1H,d,J=18.0 Hz), 3.81 (1H,d,J=16.4 Hz), 3.99 (1H,d, J=17.2 Hz), 4.82 (1H,d,J=16.4 Hz), 5.78 (1H,br.s), 6.80–7.79 (13H,m).

Elemental Analysis (C$_{29}$H$_{30}$N$_4$O$_4$) Calcd.: C, 69.86; H, 6.06; N, 11.24 Found: C, 69.72; H, 6.17; N, 11.04.

EXAMPLE 2

2-(N-(t-Butoxycarbonylmethyl)-N-(N'-(m-tolyl)ureidomethylcarbonyl)amino)benzophenone 5b According to the same manner as that described in Example 1, the objective compound 5b is prepared using the compound 4b as a starting material. Yield 50%, Mp. 183°–184° C.

IR $v_{max}$ (KBr):3344, 1746, 1658, 1618, 1561 cm$^{-1}$.

NMR (CDCl$_3$) δ:1.39 (9H,s), 2.28 (3H,s), 3.65 (1H,d,J=17.8 Hz), 3.77 (1H,d,J=17.8 Hz), 4.01 (1H,d,J=17.4 Hz), 4.64 (1H,d,J=17.4 Hz), 5.90 (1H,br.s), 6.81–6.84 (1H,d,J=6.0 Hz), 6.95–7.81 (13H,m).

Elemental Analysis (C$_{29}$H$_{31}$N$_3$O$_5$) Calcd.: C, 69.44; H, 6.23; N, 8.38 Found: C, 69.14; H, 6.28; N, 8.33.

EXAMPLE 3

2-(N-(Cyclopropylcarbonylmethyl)-N-(N'-(m-tolyl)ureidomethylcarbonyl)amino)benzophenone 5c According to the same manner as that described in Example 2, the objective compound 5c is prepared using the compound 4c as a starting material. Yield 3.3%, Mp. 114°–118° C.

IR $v_{max}$ (KBr):3391, 1650, 1611, 1596, 1556 cm$^{-1}$.

NMR (CDCl$_3$) δ:1.16 (4H,m), 1.94 (1H,br.s), 3.23 (3H,s), 3.43–4.67(4H,m), 6.07 (1H,br.s), 6.79 (2H,d,J=6.4 Hz), 7.04–7.40 (13H,m), 8.27 (1H,s).

EXAMPLE 4

2-(N-(m-Aminobenzyl)-N-(N'-(m-tolyl)ureidomethylcarbonyl)amino)-benzophenone 5d

According to the same manner as that described in Example 1 ,N-alkylation is carried out using m-(BOC-A amino)benzyl bromide in place of bromoacetylpyrrolidine. To the resultant BOC-compound, an ethyl acetate solution of 4N hydrogen chloride is added, and the mixture is stirred overnight. The mixed solution is alkalified with an aqueous sodium carbonate solution and extracted with ethyl acetate. The extract is washed with water, dried (sodium sulfate), and then the solvent is distilled off under reduced pressure. Yield 12%, Mp. 96°–100° C.

IR $v_{max}$ (KBr):3359, 1662, 1594, 1555 cm$^{-1}$.

NMR (CDCl$_3$):2.22 (3H,s), 3.48 (2H,br.s), 3.98 (2H,m), 4.27 (2H,d,J=14.4 Hz), 5.07 (1H,d,J=14.4 Hz), 6.32–7.69 (17H,m).

Elemental Analysis (C$_{30}$H$_{28}$N$_4$O$_3$.0.2H$_2$O) Calcd.: C, 72.62; H, 5.77; N, 11.29 Found: C, 72.49; H, 5.88; N, 11.49.

EXAMPLE 5

2-(N-(t-Butoxycarbonylmethyl)-N-(2-(N'-(m-tolyl)ureido)etylcarbonyl)amino)benzophenone 5e, 5f According to the same manner as that described in Example 2, the titled compounds are prepared using the compounds 4b, 4c as the starting material.

Compound 5e
Yield 31.2%.
$[\alpha]_D^{24}$+14.4 (c 1.151, CHCl$_3$)
IR $v_{max}$ (nujol):3368, 1741, 1665, 1642, 1553 cm$^{-1}$.
NMR (CDCl$_3$+CD$_3$OD) δ:1.0–1.5 (9H,m), 2.31 and 2.28 (total 3H,s),3.65–3.80 (1H,m), 4.35–4.75 (2H,m), 6.75–7.90 (13H,m).

Elemental Analysis (C$_{30}$H$_{33}$N$_3$O$_5$.0.5H$_2$O) Calcd.: C, 68.68; H, 6.53; N, 8.01 Found: C, 68.67; H, 6.52; N, 8.22.

Compound 5f
$[\alpha]_D^{23}$–18.3 (c 0.717, CHCl$_3$).

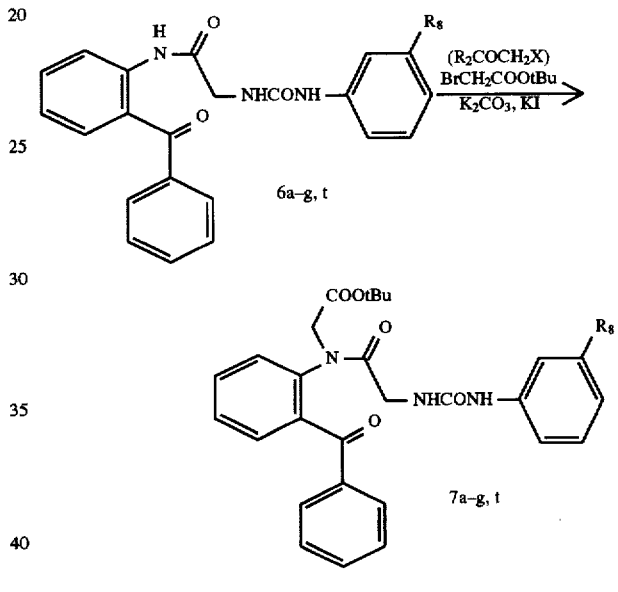

R$_s$ = a: —COOCH$_2$Ph,
b: —COOCH$_2$CH=CH$_2$,
c: —CH$_2$COOCH$_2$CH=CH$_2$,
d: —OCH$_2$COOCH$_2$CH=CH$_2$,
e: —SCH$_2$COOCH$_2$CH=CH$_2$, f:

g: —OCH$_2$— f: —CF$_3$

EXAMPLE 6

2-(N-(tert-Butoxycarbonylmethyl)-N'-(m-(benzyloxycarbonyl)phenyl)ureidomethylcarbonylamino)benzophenone 7a According to the production method of the compound 5b of Example 2, the compound 6a prepared in Preparation 7 is used to synthesize the titled compound. Mp. 85°–88° C.

IR $v_{max}$ (KBr):3380, 1720, 1661, 1597, 1555 cm$^{-1}$.

NMR (DMSO-d$_6$) δ:1.36 (9H,s), 3.53–3.85 (2H,m), 3.73 (1H,d,J=16.8 Hz), 4.14 (1H,d,J=16.8 Hz), 5.33 (2H,s), 6.38 (1H,br.s), 7.30–7.85 (17H,m), 8.05 (1H,br.s), 9.09 (1H,s).

Elemental Analysis ($C_{36}H_{35}N_3O_7$) Calcd.: C, 69.55; H, 5.67; N, 6.76 Found: C, 69.41; H, 5.74; N, 6.79.

EXAMPLE 7

2-(N-(tert-Butoxycarbonylmethyl)-N'-(m-(allyloxycarbonyl)phenyl)ureidomethylcarbonylamino)benzophenone 7b According to the same manner as that described in Example 2, the compound 6b is used as the starting substance to synthesize the titled compound. Mp. 105°–107° C.

IR $v_{max}$ (KBr):3385,1743,1722,1662,1597,1558 cm$^{-1}$.

NMR (CDCl$_3$) δ:1.39 (9H,s), 3.65 (1H,d,J=17.2 Hz), 3.80 (1H,dd,J=17.2, 4.6 Hz), 4.63 (1H,d,J=17.2 Hz), 4.79 (2H, d,J=5.8 Hz), 5.20–5.46(2H,m), 5.82–6.14 (2H,m), 7.01 (1H, s), 7.22–7.86 (12H,m), 7.96 (1H,br.s).

Elemental Analysis ($C_{32}H_{33}N_3O_7$) Calcd.: C, 67.24; H, 5.82; N, 7.35 Found: C, 66.98; H, 5.80; N, 7.31.

EXAMPLE 8

2-(N-(tert-Butoxycarbonylmethyl)-N'-(m-(2-propenyloxycarbonylmethyl)phenyl)ureidomethylcarbonylamino)benzophenone 7c According to the same manner as that described in Example 2, the compound 6c is used as the starting substance to synthesize the titled compound. Mp. 122°–124° C.

IR $v_{max}$ (KBr):3360, 1740, 1662, 1645, 1610, 1595, 1560 cm$^{-1}$.

NMR (CDCl$_3$) δ:1.40 (9H,s), 3.59 (2H,s), 3.64 (1H,d,J=17.2 Hz), 3.77(1H,dd,J=17.0, 5.0 Hz), 4.00 (1H,dd,J=17.0, 5.0 Hz), 4.53–4.61 (2H,m), 4.64 (1H,d,J=17.2 Hz), 5.13–5.32 (2H,m), 5.72–5.99 (2H,m), 6.75 (1H,s), 6.89–6.97 (1H,m), 7.11–7.30 (4H,m), 7.4–7.67 (6H,m), 7.72–7.84 (3H,m).

Elemental Analysis ($C_{33}H_{35}N_3O_7$) Calcd.: C, 67.68; H, 6.02; N, 7.18 Found: C, 67.68; H, 6.09; N, 7.19.

EXAMPLE 9

2-(N-(tert-Butoxycarbonylmethyl)-N'-(m-(2-propenyloxycarbonylmethyloxy)phenyl)ureidomethylcarbonylamino)benzophenone 7d According to the same manner as that described in Example 2, the compound 6d is used as the starting substance to synthesize the titled compound. Mp. 134°–136° C.

IR $v_{max}$ (KBr):3390, 1760, 1739, 1660, 1650, 1610, 1560, 1500 cm$^{-1}$.

NMR (CDCl$_3$) δ:1.40 (9H,s), 3.63 (1H,d,J=17.4 Hz), 3.76 (1H,dd,J=17.4, 3.6Hz), 4.00 (1H,dd,J=17.4, 3.6 Hz), 4.62 (2H,s), 4.64 (1H,d,J=17.4 Hz), 4.69 (1H,d,J=5.6 Hz), 5.19–5.38 (2H,m), 5.77–6.01 (2H,m),6.57 (1H,dd,J=7.6,2.6 Hz), 6.73–6.87 (2H,m), 7.00–7.18 (2H,m),7.37–7.68 (6H, m), 7.72–7.84 (3H,m).

Elemental Analysis ($C_{33}H_{35}N_3O_8$) Calcd.: C, 65.88; H, 5.86; N, 6.98 Found: C, 65.76; H, 5.89; N, 6.92.

EXAMPLE 10

2-(N-(tert-Butoxycarbonylmethyl)-N'-(m-(2-propenyloxycarbonylmethylthio)phenyl)ureidomethylcarbonylamino)benzophenone 7e According to the same manner as that described in Example 2, the compound 6e is used as the starting substance to synthesize the titled compound. Mp. 155°–157° C.

IR $v_{max}$ (KBr):3380, 1740, 1650, 1595, 1550 cm$^{-1}$.

NMR (CDCl$_3$) δ:1.40 (9H,s), 3.63 (1H,d,J=17.4 Hz), 3.67 (2H,s), 3.78 (1H,dd,J=17.2, 5.6 Hz), 4.01 (1H,dd, 17.2, 5.6 Hz), 4.55–4.62 (2H,m), 4.73 (1H,d,J=17.4 Hz), 5.16–5.32 (2H,m), 5.73–6.00 (2H,m),6.86(1H,s), 6.96–7.07 (1H,m), 7.08–7.16 (2H,m), 7.33 (10H,m).

Elemental Analysis ($C_{33}H_{35}N_3O_7S$) Calcd.: C, 64.17; H, 5.71; N, 6.80; S, 5.19 Found: C, 64.22; H, 5.80; N, 6.79; S, 5.08.

EXAMPLE 11

2-(N-(tert-Butoxycarbonylmethyl)-N'-(m-(2-(triphenylmethyl)tetrazol-5-yl)phenyl)ureidomethylcarbonylamino)benzophenone 7f According to the same manner as that described in Example 2, the compound 6f is used as the starting substance to synthesize the titled compound. Powder.

IR $v_{max}$ (KBr):3380, 1740, 1662, 1595, 1560, 1515 cm$^{-1}$.

NMR(CDCl$_3$) δ:1.40 (9H,s), 3.63 (1H,d,J=17.2 Hz), 3.80 (1H,d,J=17.2 Hz), 3.99 (1H,dd,J=17.2, 4.6 Hz), 4.63 (1H,d, 17.2 Hz), 5.71 (1H,br.s), 6.70 (1H,s), 7.00–7.90 (28H,m).

Elemental Analysis ($C_{48}H_{43}N_7O_5 \cdot 0.5CH_3C_6H_5$) Calcd.: C, 73.29; H, 5.61; N, 11.62 Found: C, 72.95; H, 5.76; N, 11.31.

EXAMPLE 12

2-(N-(tert-Butoxycarbonylmethyl)-N'-(m-(2-(triphenylmethyl)-tetrazol-5-ylmethyloxy)phenyl)ureidomethylcarbonylamino)benzophenone 7g According to the same manner as that described in Example 2, the compound 6g is used as the starting substance to synthesize the titled compound.

IR $v_{max}$ (KBr):3380, 1740, 1662, 1600, 1548 cm$^{-1}$.

NMR (CDCl$_3$) δ:1.39 (9H,s), 3.64 (1H,d,J=17.4 Hz), 3.76 (1H,dd,J=17.8, 4.6 Hz), 3.98(1H,dd,J=17.8, 4.6 Hz), 4.64 (1H,d, 17.4 Hz), 5.28(2H,s), 5.81 (1H,br.s), 6.58–6.73 (2H, m), 6.83–6.91 (1H,m), 6.99–7.66 (23H,m), 7.71–7.83 (3H, m).

Elemental Analysis ($C_{49}H_{45}N_7O_6 \cdot 0.3CH_3C_6H_5$) Calcd.: C, 71.74; H, 5.58; N, 11.46 Found: C, 71.58; H, 5.65; N, 11.38.

EXAMPLE 13

2-(N-(tert-Butoxycarbonylmethyl)-N'-(m-trifluoromethylphenyl)ureidomethylcarbonylamino)benzophenone 7t According to the same manner as that described in Example 2, the compound 6t is used as the starting substance to synthesize the titled compound. Powder.

NMR(CDCl$_3$) δ:1.36 (9H,s), 3.68 (1H,d,J=17.2 Hz), 3.79 (1H,d,J=17.4 Hz), 4.10(1H,d,J=17.4 Hz), 4.61 (1H,d,J=17.2 Hz), 7.07–7.88 (13H,m).

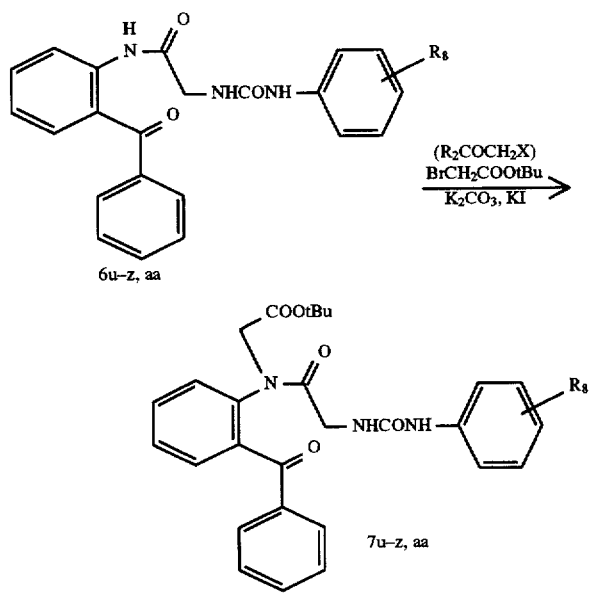

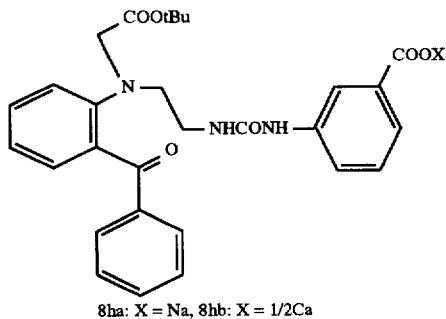

$R_8$ = u: m-Cl,
v: m-Br,
w: m-CN, x: m-OCH$_3$,
y: p-Cl, z: p-Me, aa: H

8ha: X = Na, 8hb: X = 1/2Ca

EXAMPLE 14

2-(N-(tert-Butoxycarbonylmethyl)-N'-(m-chlorophenyl)ureidomethylcarbonylamino) benzophenone 7u A solution of the amide 6u (977 mg, 2 mmol) prepared in Preparation 15, t-butyl bromoacetate (420 μg, 2.6 mmol), potassium carbonate (359 mg, 2.6 mmol) and potassium iodide (33 mg, 0.2 mmol) in imethylformamide (6 ml) is stirred overnight. After pouring into water, the mixture is extracted with ethyl acetate. The extract is washed with water and dried (sodium sulfate), and then the solvent is distilled off under reduced pressure. The residue is recrystallized from toluene. Yield 58%; Mp. 160°–161° C.

IR $v_{max}$ (KBr):1742, 1662, 1644, 1595, 1546 cm$^{-1}$.

NMR (CDCl$_3$) δ:1.37 (9H,s), 3.67 (1H,d,J=17.2 Hz), 3.77 (1H,dd,J=17.4, 5.6 Hz), 4.05 (1H,dd,J=17.4, 5.6 Hz), 4.05 (1H,dd,J=17.2, 5.6 Hz), 4.60 (1H,d,J=17.2 Hz), 6.12 (1H, br.s), 6.89 (1H, br.s.), 7.06 (1H,m), 7.25 (2H,s), 7.41–7.69 (7H,m), 7.80 (2H,m).

Elemental Analysis (C$_{28}$H$_{28}$N$_3$O$_5$Cl) Calcd.: C,64.43; H,5.41;Cl,6.79; N,8.05 Found: C,64.19; H,5.54; Cl,6.65; N,7.93.

EXAMPLE 15

2-(N-(tert-Butoxycarbonylmethyl)-N'-(m-bromophenyl)ureidomethylcarbonylamino) benzophenone 7v According to the same manner as that described in Example 14, the compound 6v prepared in Preparation 16 is used as the starting substance to synthesize the titled compound.

IR $v_{max}$ (KBr):1741, 1663, 1593, 1539 cm$^{-1}$.

NMR (CDCl$_3$) δ:1.38 (9H,s), 3.67 (1H,d,J=17.2 Hz), 3.78 (1H,dd,J=17.2, 4.4 Hz), 4.04 (1H,dd,J=17.4, 4.4 Hz), 4.61 (1H,d,J=17.2 Hz), 6.09 (1H,br.s), 6.95–7.27 (5H,m), 7.42–7.70 (6H,m), 7.76–7.85 (3H,m).

Elemental Analysis (C$_{28}$H$_{28}$N$_3$O$_5$Br) Calcd.: C,59.37; H,4.98; Br,14.11; N,7.42 Found: C,59.25; H,4.98; Br,13.85; N,7.33.

EXAMPLE 16

2-(N-(tert-Butoxycarbonylmethyl)-N'-(m-cyanophenyl)ureidomethylcarbonylamino) benzophenone 7w According to the same manner as that described in Example 14, the compound 6w prepared in Preparation 17 is used as the starting substance to synthesize the titled compound.

IR $v_{max}$ (KBr):2228, 1741, 1664, 1594, 1553 cm$^{-1}$.

NMR (CDCl$_3$) δ:1.36 (9H,s), 3.69 (1H,d,J=17.2 Hz), 3.73 (1H,dd,J=17.2, 6.0 Hz), 4.12 (1H,dd,J=17.2, 6.0 Hz), 4.60 (1H,d,J=17.2 Hz), 6.41 (1H,br.s), 7.08–7.33 (4H,m), 7.43–7.91 (10H,m).

Elemental Analysis (C$_{29}$H$_{28}$N$_4$O$_5$·0.4H$_2$O) Calcd.: C,67.01; H,5.58; N,10.78 Found: C,66.98; H,5.56; N,10.71.

EXAMPLE 17

2-(N-(tert-Butoxycarbonylmethyl)-N'-(m-methoxyphenyl)ureidomethylcarbonylamino) benzophenone 7x According to the same manner as that described in Example 14, the compound 6x prepared in Preparation 18 is used as the starting substance to synthesize the titled compound. Mp. 153°–155° C.

IR $v_{max}$ (KBr):1743, 1663, 1646, 1608, 1556, 1575 cm$^{-1}$.

NMR(CDCl$_3$) δ:1.39 (9H,s), 3.64 (1H,d,J=17.2 Hz), 3.75 (3H,s), 3.78(1H,dd,J=17.2,4.0 Hz), 4.03 (1H,dd,J=17.2,4.0 Hz), 4.63 (1H,d,J=17.2 Hz), 6.00 (1H,br.s), 6.51–6.58 (1H. m), 6.68–6.77 (1H.m), 6.98–7.16(3H,m), 7.40–7.67 (6H,m), 7.40–7.67 (6H,m).

Elemental Analysis (C$_{29}$H$_{31}$N$_3$O$_6$) Calcd.: C,67.30; H,6.04; N,8.12 Found: C,67.30; H,6.10; N,8.16

EXAMPLE 18

2-(N-(tert-Butoxycarbonylmethyl)-N'-(p-chlorophenyl)ureidomethylcarbonylamino) benzophenone 7y According to the same manner as that described in Example 14, the compound 6y prepared in Preparation 19 is used as the starting substance to synthesize the titled compound. Mp. 196°–197° C.

IR $v_{max}$ (KBr):1742, 1660, 1578, 1548 cm$^{-1}$.

NMR (CDCl$_3$) δ:1.37 (9H,s), 3.66 (1H,d,J=17.2 Hz), 3.77 (1H,dd,J=17.4,4.4 Hz), 4.07 (1H,dd,J=17.4,4.4 Hz), 4.61

(1H,d,J=17.2 Hz), 6.10(1H,br,s), 7.06–7.28 (6H,m), 7.43–7.83 (8H,m).

Elemental Analysis ($C_{28}H_{28}N_3O_5Cl$) Calcd.: C,64.43; H,5.41; Cl,6.79; N,8.05 Found: C,64.41; H,5.49; Cl,6.90; N,8.04.

EXAMPLE 19

2-(N-(tert-Butoxycarbonylmethyl)-N'-(p-tolyl) ureidomethylcarbonylamino)benzophenone 7z According to the same manner as that described in Example 14, the compound 6z prepared in Preparation 20 is used as the starting substance to synthesize the titled compound. Mp. 182°–183° C.

IR $v_{max}$ (KBr):1742, 1661, 1598, 1577, 1548 cm$^{-1}$.

NMR(CDCl$_3$) δ:1.43 (9H,s), 2.28 (3H,s), 3.64 (1H,d,J=17.2 Hz), 3.74(1H,dd,J=17.4,4.0 Hz), 4.01 (1H,dd,J=17.4, 4.0 Hz), 4.63 (1H,d,J=17.2 Hz), 5.77 (1H,br,s),7.00–7.22 (4H,m), 7.42–7.83 (10H,m).

Elemental Analysis ($C_{29}H_{31}N_3O_5$) Calcd.: C,69.44; H,6.23; N,8.38 Found: C,69.68; H,6.33; N,8.34.

EXAMPLE 20

2-(N-(tert-Butoxycarbonylmethyl)-N'-phenylureidomethylcarbonylamino)benzophenone 7aa According to the same manner as that described in Example 14, the compound 6aa prepared in Preparation 21 is used as the starting substance to synthesize the titled compound. Mp. 166°–167° C.

IR $v_{max}$ (KBr): 1743, 1662, 1598, 1553, 1498 cm$^{-1}$.

NMR (CDCl$_3$) δ:1.39 (9H,s), 3.65 (1H,d,J=17.4 Hz), 3.79 (1H,dd,J=17.6, 4.2 Hz), 4.04 (1H,dd,J=17.6, 4.2 Hz), 4.64 (1H,d,J=17.4 Hz), 5.97(1H,br,s), 7.01 (2H,br,s), 7.16–7.30 (5H,m), 7.40–7.85 (7H,m).

Elemental Analysis ($C_{28}H_{29}N_3O_5$) Calcd.:C, 68.98; H,6.00; N,8.62 Found:C, 68.94; H,6.03; N,8.62.

EXAMPLE 21

2-[(tert-Butoxycarbonylmethyl)-[3-(m-(carboxylphenyl)ureidomethylcarbonyl]] aminobenzophenone sodium salt 8ha (1) 2-(N'-(m-(2-propenyloxycarbonyl)phenyl) ureidomethylcarbamoyl)benzophenone 6b To a solution of m-(3-propenyloxycarbonyl)phenyl isocyanate which is prepared from a solution of m-(3-propenyloxy)aniline (1.3 g, 6.80 mmol), triophosgene (665 mg, 2.38 mmol) and triethylamine (996 μl, 7.1.4 mmol) in tetrahydrofuran (50 ml) according to the method described in EP-508796-A1, a solution of the compound 3a (1.852 g, 5.53 mmol) prepared in Preparation 3 in tetrahydrofuran (10 ml) is added under ice-cooling. Furthermore, triethylamine (810 μg, 5.80 mmol) is added and the mixture is treated according to the same manner as that described in Preparation 15 to prepare the objective compound (1.678 g, yield 68%). Mp. 68°–71° C.

IR $v_{max}$(KBr):3350, 1718, 1692, 1659, 1595, 1580, 1557, 1520 cm$^{-1}$.

NMR (CDCl3) δ:4.12 (2H,d,J=5.6 Hz), 4.77 (2H,d,J=5.6 Hz), 5.20–5.43 (2H,m), 5.88–6.10 (2H,m), 7.04–7.18 (3H, m), 7.36–7.70 (10H,m),7.90 (1H,br,s), 8.54 (1H,d,J=8.6 Hz).

Elemental Analysis ($C_{26}H_{23}N_3O_5$) Calcd.: C,68.26; H,5.07; N,9.19 Found :C,68.30; H,5.19; N,9.16.

(2) 2-(N-(tert-Butoxycarbonylmethyl)-N'-(m-(2-propenyloxycarbonyl)phenyl) ureidomethylcarbonylamino)benzophenone 7b According to the same manner as that described in Example 14, the compound 6b is used as the starting substance to synthesize the titled compound. Mp. 105°–107° C.

IR $v_{max}$(KBr):3385, 1743, 1722, 1662, 1597, 1558 cm$^{-1}$.

NMR (CDCl$_3$) δ:1.39 (9H,s), 3.65 (1H,d,J=17.2 Hz), 3.80 (1H,dd,J=17.2,4.6 Hz), 4.63 (1H,d,J=17.2 Hz), 4.79 (2H,d, J=5.8 Hz), 5.20–5.46 (2H,m), 5.82–6.14 (2H,m), 7.01 (1H, s), 7.22–7.86 (12H,m), 7.96 (1H,br,s).

Elemental Analysis ($C_{32}H_{33}N_3O_7$) Calcd.: C,67.24; H,5.82; N,7.35 Found :C,66.98; H,5.80; N,7.31.

(3) 2-[(tert-Butoxycarbonylmethyl)-[3-(m-(carboxyphenyl) ureidomethylcarbonyl]]aminobenzophenone 8h To a solution of the above allyl ester 7b (820 mg, 1.43 mmol), palladium tetrakistriphenylphosphine (41.4 mg, 0.036 mmol) and triphenylphosphine (19 mg, 0.072 mmol) in dichloromethane (0.5 ml) is added a solution of pyrrolidine (127 μl, 1.51 mmol) in dichloromethane (0.5 ml) with stirring at 0° C. Fifteen minutes later, the reaction solution is diluted with ethyl acetate and extracted with an aqueous 15% sodium bicarbonate solution. The basic layer is adjusted to pH 2 with 5% hydrochloric acid and extracted with ethyl acetate. The ethyl acetate layer is washed with water, dried (sodium sulfate) and then concentrated under reduced pressure to obtain the titled powdery compound 8h (256 mg, 34%).

IR $v_{max}$ (KBr):3380, 1665, 1595, 1555 cm$^{-1}$.

NMR(CDCl$_3$) δ:3.69 (1H,d,J=17.2 Hz), 3.83 (1H,dd,J= 17.2, 4.6 Hz), 4.05 (1H,dd,J=17.2,4.6 Hz), 4.70 (1H,d,J= 17.2 Hz), 7.17–7.27 (1H,br,s), 7.30–7.85 (12H,m), 8.17 (1H,s), 8.30–8.41 (1H,m).

(4) 2-[(tert-Butoxycarbonylmethyl)-[3-(m-(carboxyphenyl) ureidomethylcarbonyl]]aminobenzophenone sodium salt 8ha A solution of the compound 8h (11.266 g, 21.2 mmol) in methanol (700 ml) and water (50 ml) is neutralized with aqueous 1N sodium hydroxide (21.2 ml) and then concentrated under reduced pressure. To the resultant residue is added water (200 ml), followed by freeze-drying to obtain the titled compound 8ha (12.49 g, 100%) as colorless powder.

NMR(CD$_3$OD) δ:1.42 (9H,s), 3.77 (1H,d,J=17.0 Hz), 3.78 (1H,d,J=17.4 Hz), 3.94 (1H,d,J=17.4 Hz), 4.37 (1H,d, J=17.0 Hz), 7.16–7.28 (1H,m),7.44–7.87 (13H,m).

Elemental Analysis ($C_{29}H_{28}N_3O_7Na.2H_2O$) Calcd.: C,59.08; H,5.47; N,7.13; Na,3.90 Found: C,59.19; H,5.48; N,7.42; Na,3.95.

EXAMPLE 22

2-[(tert-Butoxycarbonylmethyl)-[3-(m-(carboxyphenyl)ureidomethylcarbonyl]] aminobenzophenone calcium salt 8hb To a solution of the compound 8ha (7.496 g, 12.7 mmol) in water (200 ml) is added dropwise an aqueous solution (50 ml) of calcium chloride (1.411 g, 12.7 mmol) with stirring. After 6-hour-stirring, colorless powder is filtered off to obtain 5.156 g (70.2%) of the titled compound.

NMR(CD$_3$OD) δ:1.41 (9H,s), 3.71 (1H,d,J=17.2 Hz), 3.79 (1H,d,J=17.4 Hz), 3.94 (1H,d,J=17.4 Hz), 4.36 (1H,d, J=17.2 Hz), 7.17–7.29 (1H,m),7.23–7.90 (13H,m).

Elemental Analysis (C$_{58}$H$_{56}$N$_6$O$_{14}$Ca.3H$_2$O) Calcd.: C,60.30; H,5.41; N,7.27; Ca,3.47 Found: C,60.74; H,5.40; N,7.46; Ca,3.44.

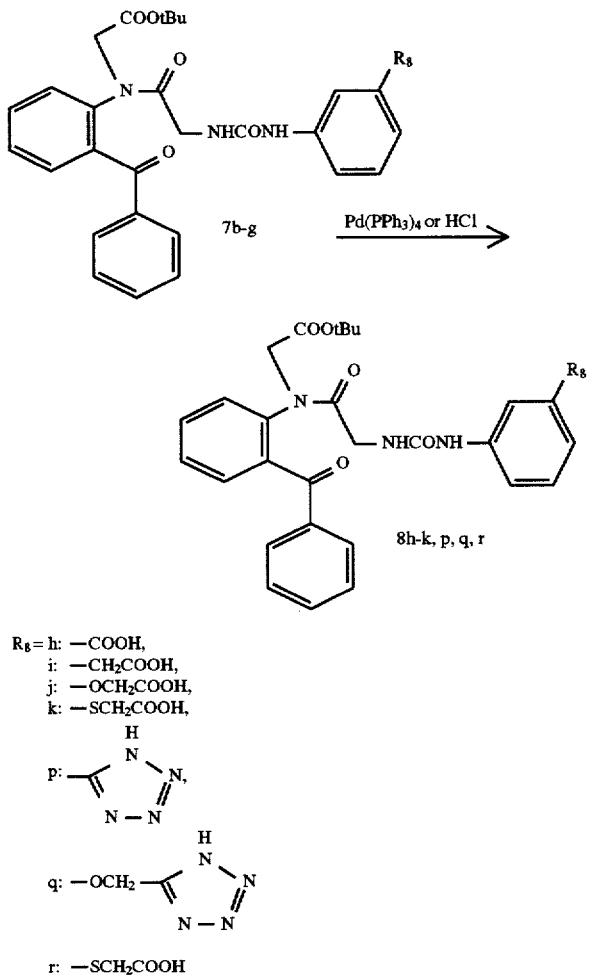

7b-g

Pd(PPh$_3$)$_4$ or HCl →

8h-k, p, q, r

R$_8$ = h: —COOH,
i: —CH$_2$COOH,
j: —OCH$_2$COOH,
k: —SCH$_2$COOH, p: (tetrazolyl-CH group)

q: —OCH$_2$-(tetrazolyl)

r: —SCH$_2$COOH

EXAMPLE 23

2-[(tert-Butoxycarbonylmethyl)-[3-(m-(carboxyphenyl)ureidomethylcarbonyl]] aminobenzophenone 8h To a solution of the allyl ester 7b (820 mg, 1.43 mmol) prepared in Example 7, palladium tetrakistriphenylphosphine (41.4 mg, 0.036 mmol) and triphenylphosphine (19 mg, 0.072 mmol) in dichloromethane (0.5 ml), a solution of pyrrolidine (127 μl, 1.51 mmol) in dichloromethane (0.5 ml) is added with stirring at 0° C. Fifteen minutes later, the reaction solution is diluted with ethyl acetate and extracted with an aqueous 15% sodium bicarbonate solution. The alkali layer is adjusted to pH 2 using 5% hydrochloric acid and extracted with ethyl acetate. The ethyl acetate layer is washed with water, dried (sodium sulfate) and then concentrated under reduced pressure to obtain the titled powdery compound (256 mg, 34%).

IR v$_{max}$ (KBr):3380, 1665, 1595, 1555 cm$^{-1}$.

NMR (CDCl$_3$) δ:3.69 (1H,d,J=17.2 Hz), 3.83 (1H,dd,J=17.2, 4.6 Hz), 4.05 (1H,dd,J=17.2, 4.6 Hz), 4.70 (1H,d,J=17.2 Hz), 7.17–7.27 (1H,br.s), 7.30–7.85 (12H,m), 8.17 (1H,s), 8.30–8.41 (1H,m).

EXAMPLE 24

2-(N-(tert-Butoxycarbonylmethyl)-N'-(m-(carboxymethyl)phenyl) ureidomethylcarbonylamino)benzophenone 8i According to the same manner as that described in Example 23, the allyl ester 7c prepared in Example 8 is used to synthesize the titled compound. Mp. 96°–98° C.

IR v$_{max}$ (KBr):3380, 1739, 1661, 1594, 1555 cm$^{-1}$.

NMR (CDCl$_3$) δ:1.41 (9H,s), 3.57 (2H,s), 3.63 (1H,d,J=17.2 Hz), 3.75 (1H,dd,J=17.0, 5.0 Hz), 4.02 (1H,dd,J=17.0, 5.0 Hz), 4.61 (1H,d,J=17.2 Hz), 6.42 (1H,br.s), 6.81–6.97 (2H,m), 7.12–7.24 (1H,m), 7.40–7.70 (7H,m), 7.71–7.82 (3H,m).

Elemental Analysis (C$_{30}$H$_{31}$N$_3$O$_7$.0.4H$_2$O) Calcd.: C, 65.18; H, 5.80; N, 7.6 Found: C, 65.15; H, 5.77; N, 7.46.

EXAMPLE 25

2-(N-(tert-Butoxycarbonylmethyl)-N'-(m-(carboxymethyloxy)phenyl) ureidomethylcarbonylamino)benzophenone 8j According to the same manner as that described in Example 23, the allyl ester 7d prepared in Example 9 is used to synthesize the titled compound. Powder IR v$_{max}$ (KBr):3380, 1740, 1662, 1599, 1551 cm$^{-1}$.

NMR (CDCl$_3$) δ:1.41 (9H,s), 3.67 (1H,d,J=17.0 Hz), 3.76 (1H,dd,J=17.4, 3.6 Hz), 4.06 (1H,dd,J=17.4, 3.6 Hz), 4.59 (2H,s), 4.62 (1H,d,J=17.0 Hz), 6.38–6.53 (2H,m), 6.71 (1H,br.s), 7.04–7.26 (2H,m), 7.40–7.70 (6H,m), 7.73–7.82 (3H,m).

Elemental Analysis (C$_{30}$H$_{31}$N$_3$O$_8$.0.4H$_2$O) Calcd.: C, 63.35; H, 5.64; N, 7.39 Found: C, 63.34; H, 5.70; N, 7.29.

EXAMPLE 26

2-(N-(tert-Butoxycarbonylmethyl)-N'-(m-(carboxymethylthio)phenyl) ureidomethylcarbonylamino)benzophenone 8k According to the same manner as that described in Example 23, the allyl ester 7e prepared in Example 10 is used to synthesize the titled compound.

IR v$_{max}$ (KBr):3380, 1738, 1661, 1595, 1547 cm$^{-1}$.

NMR (CDCl$_3$) δ:1.38 (9H,s), 3.60 (2H,s), 3.68 (1H,d,J=17.4 Hz), 3.80 (1H,dd,J=17.2, 5.6 Hz), 4.03 (1H,dd,J=17.2, 5.6 Hz), 4.60 (1H,d,J=17.4 Hz), 6.28 (1H,br.s), 6.97–7.24 (4H,m), 7.38–7.70 (7H,m), 7.76–7.88 (3H,m).

Elemental Analysis (C$_{30}$H$_{31}$N$_3$O$_7$S.0.5H$_2$O) Calcd.: C, 61.42; H, 5.50; N, 7.16; S, 5.47 Found: C, 61.51; H, 5.51; N, 7.04.

EXAMPLE 27

2-(N-(tert-Butoxycarbonylmethyl)-N'-(m-(tetrazol-5-yl)phenyl)ureidomethylcarbonylamino) benzophenone 8p To a solution of of the trityl compound f (570 mg, 0.71 mmol) prepared in Example 11 in tetrahydrofuran (3 ml) and ethanol (10 ml) is added 1N hydrochloric acid (2.9 ml) and stirred at room temperature. Three hours later, water is poured into the reaction solution, and extracted with ethyl acetate. After the organic layer is washed with water and dried (sodium sulfate), the solvent is distilled off to obtain the titled compound (187 mg; 33.7%). Mp.163°–175° C.

IR $v_{max}$ (KBr):3380, 1740, 1661, 1595, 1570 cm$^{-1}$.

NMR (CDCl$_3$+CD$_3$OD) δ:1.34 (9H,s), 3.67 (1H,d,J=17.4 Hz), 3.85 (1H,d,J=17.4 Hz), 4.01 (1H,d,J=17.4 Hz), 7.07–7.92 (13H,m).

Elemental Analysis (C$_{29}$H$_{29}$N$_7$O$_5$.H$_2$O) Calcd.: C, 60.72; H, 5.45; N, 17.09 Found: C, 60.86; H, 5.40; N, 16.72.

EXAMPLE 28

2-(N-(tert-Butoxycarbonylmethyl)-N'-(m-(tetrazol-5-ylmethyloxy)phenyl)ureidomethylcarbonylamino)benzophenone 8q According to the same manner as that described in Example 27, the trityl compound 7g prepared in Example 12 is used to synthesize the titled compound.

IR $v_{max}$ (KBr):3400, 1741, 1662, 1600, 1555 cm$^{-1}$.

NMR (CDCl$_3$+CD$_3$OD) δ:1.39 (9H,s), 3.64 (1H,d,J=17.4 Hz), 3.81 (1H,d,J=17.4 Hz), 4.58(1H,d,J=17.4 Hz), 5.28 (2H,dd, 20.1, 14.0 Hz), 6.36–6.47 (1H,m), 6.77–7.03 (3H, m), 7.44–8.00 (11H,m).

Elemental Analysis (C$_{30}$H$_{31}$N$_7$O$_6$.0.4H$_2$O) Calcd.: C, 60.78; H, 5.41; N, 16.54 Found: C, 60.87; H, 5.43; N, 16.46.

EXAMPLE 29

2-(N-(tert-Butoxycarbonylmethyl)-N'-(m-(carboxymethylsulfinyl)phenyl)ureidomethylcarbonylamino)benzophenone 8r The compound 8k is treated with m-chloroperbenzoic acid in a conventional manner to obtain the titled compound. Powder NMR (CDCl$_3$) δ:1.43 (9H,s), 3.74 (1H,d,J=17.2 Hz), 3.75–3.98 (4H,m), 4.37(1H,d,J=17.2 Hz), 7.27–7.86 (13H, m).

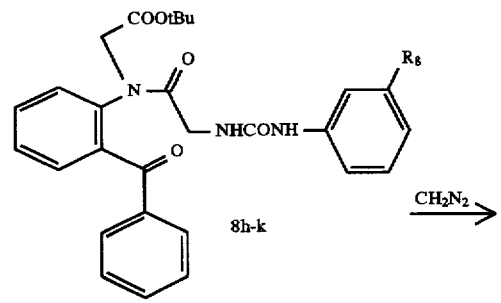

R$_8$ = h: —COOH,
i: —CH$_2$COOH,
j: —OCH$_2$COOH,
k: —SCH$_2$COOH,
l: —COOMe,
m: —CH$_2$COOMe,
n: —OCH$_2$COOMe,
o: —SCH$_2$COOMe,

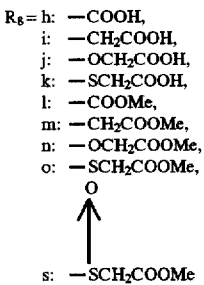

s: —SCH$_2$COOMe

EXAMPLE 30

2-(N-(tert-Butoxycarbonylmethyl)-N'-(m-(carbomethoxy)phenyl)ureidomethylcarbonylamino)benzophenone 9l The carboxylic acid 8h prepared in Example 23 is treated with a solution of excess diazomethane in ether to obtain the compound 9l.

IR $v_{max}$ (KBr):3390, 1740, 1725, 1660, 1595, 1556 cm$^{-1}$.

NMR (CDCl$_3$) δ:1.38 (9H,s), 3.66 (1H,d,J=17.0 Hz), 3.80 (1H,dd,J=17.6, 5.6 Hz), 4.04 (1H,dd,J=17.6, 5.6 Hz), 4.63 (1H,d,J=17.0 Hz), 5.96 (1H,br.s), 7.11 (1H,s), 7.22–7.32 (1H,m), 7.42–7.69 (8H,m), 7.75–7.86 (3H,m), 7.96 (1H, br.s).

Elemental Analysis (C$_{30}$H$_{31}$N$_3$O$_7$.1.3H$_2$O) Calcd.: C, 63.33; H, 5.95; N, 7.38 Found: C, 62.12; H, 5.51; N, 7.30.

EXAMPLE 31

2-(N-(tert-Butoxycarbonylmethyl)-N'-(m-(carbomethoxymethyl)phenyl)ureidomethylcarbonyl)amino)benzophenone 9m According to the same manner as that described in Example 30, the carboxylic acid 8i prepared in Example 24 is used to synthesize the titled compound. Yield 42%. Mp. 127°–129° C.

IR $v_{max}$ (KBr):3359, 1740, 1658, 1562, 1494 cm$^{-1}$.

NMR(CDCl$_3$) δ:1.39 (3H,s), 3.55 (2H,s), 3.65 (1H,d,J=17.6 Hz), 3.67(3H,s), 3.77 (1H,d,J=18.2 Hz), 4.01 (1H,d,J=17.6 Hz), 4.64 (1H,d,J=17.6 Hz), 5.88 (1H,br.s), 6.91 (1H, m), 7.15–7.81 (13H,m).

Elemental Analysis (C$_{31}$H$_{33}$N$_3$O$_7$) Calcd.: C, 66.53; H, 5.94; N, 7.56 Found: C, 66.41; H, 6.02; N, 7.61.

EXAMPLE 32

2-(N-(tert-Butoxycarbonylmethyl)-N'-(m-(carbomethoxymethyloxy)-phenyl)ureidomethylcarbonylamino)benzophenone 9n According to the same manner as that described in the synthesis of the compound 9l of Example 30, the carboxylic acid 8j prepared in Example 25 is used to synthesize the titled compound. Mp. 74°–77° C.

IR $v_{max}$ (KBr):3380, 1741, 1662, 1599, 1550 cm$^{-1}$.

NMR (CDCl$_3$) δ:1.40 (9H,s), 3.63 (1H,d,J=17.4 Hz), 3.75 (1H,dd,J=17.4, 8.6 Hz), 3.63 (1H,d,J=17.4 Hz), 4.01 (1H, dd,J=17.4, 8.6 Hz), 4.60 (2H,s), 4.63 (1H,d,J=17.4 Hz), 5.82 (1H,br.s), 6.57 (1H,dd,J=7.6, 2.6 Hz), 6.72–6.88 (2H,m), 7.00–7.18 (2H,m), 7.37–7.68 (6H,m),7.72–7.85 (3H,m).

Elemental Analysis (C$_{31}$H$_{33}$N$_3$O$_8$) Calcd.: C, 64.69; H, 5.78; N, 7.30 Found: C, 64.54; H, 5.85; N, 7.21.

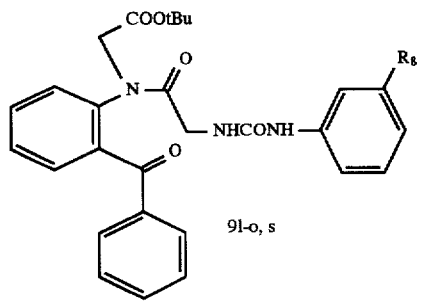

EXAMPLE 33

2-(N-(tert-Butoxycarbonylmethyl)-N'-(m-(carbomethoxymethylthio)phenyl)ureidomethylcarbonylamino)benzophenone 9o According to the same manner as that described in the synthesis of the compound 91 of Example 30, the carboxylic acid 8k prepared in Example 26 is used to synthesize the titled compound. Mp. 131°–133° C.

IR $v_{max}$(KBr):3375, 1741, 1665, 1653, 1598, 1550 cm$^{-1}$.

NMR(CDCl$_3$) δ:1.40 (9H,s), 3.66 (1H,d,J=17.4 Hz), 3.67 (2H,s), 3.72(3H,s), 3.82 (1H,dd,J=17.2, 5.6 Hz), 4.05 (1H, dd,J=17.2, 5.6 Hz), 4.64 (1H,d,J=17.4 Hz), 5.99 (1H,br.s), 6.91–7.20 (4H,m), 7.32–7.73 (7H,m), 7.75–7.87 (3H,m).

Elemental Analysis (C$_{31}$H$_{33}$N$_3$O$_7$S) Calcd.: C, 62.93; H, 5.62; N, 7.10; S, 5.42 Found: C, 62.84; H, 5.68; N, 7.07; S, 5.26.

EXAMPLE 34

2-(N-(tert-Butoxycarbonylmethyl)-N'-(m-(carbomethoxymethylsulfinyl)phenyl)ureidomethylcarbonylamino)benzophenone 9s According to the same manner as that described in the synthesis of the compound 91 of Example 30, the carboxylic acid 8r is used to synthesize the titled compound. Powder.

NMR(CDCl$_3$) δ:1.41 (9H,s), 3.70 (3H,s),3.73 (1H,d,J= 17.2 Hz), 3.74–4.00 (4H,m), 4.37 (1H,d,J=17.2 Hz), 7.09–7.87 (13H,m).

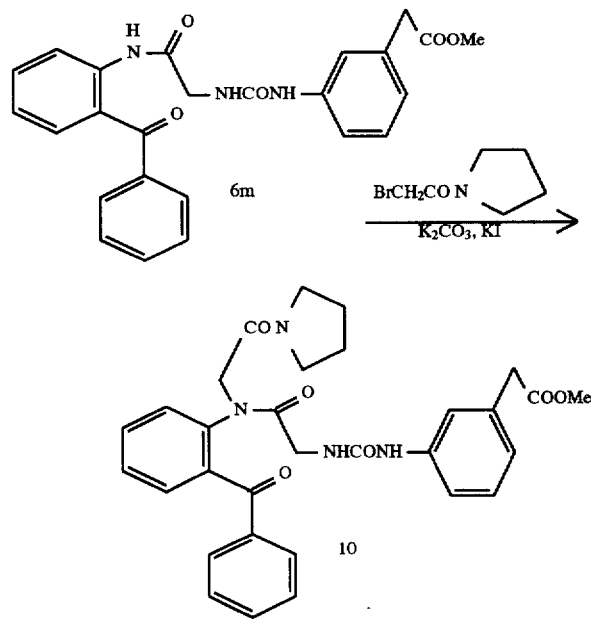

EXAMPLE 35

2-(N-(Pyrrolidinocarbonylmethyl)-N'-(m-(carbomethoxy)phenyl)ureidomethylcarbonylamino)benzophenone 10

The titled compound is prepared according to the same manner as that described in Example 1 using 6m synthesized according to the same manner usid for the preparation of 6c in Preparation 9. Yield 30.4%, Mp. 189°–194° C.

IR $v_{max}$ (KBr):3378,3332,1740,1653, 1595,1561 cm$^{-1}$.

NMR (CDCl$_3$) δ:1.84 (4H,m), 3.34 (4H,m), 3.56 (2H,s), 3.66 (3H,s),3.82 (1H,d,J=16.8 Hz), 3.86 (2H,q,J=17.2 Hz), 4.82 (1H,d,J=16.8Hz), 5.84 (1H,br.s), 6.90–6.98 (1H,m), 7.17–7.95 (13H,m).

Elemental Analysis (C$_{31}$H$_{32}$N$_4$O$_6$) Calcd.: C, 66.89; H, 5.79; N, 10.07 Found: C, 66.66; H, 5.83; N, 10.05.

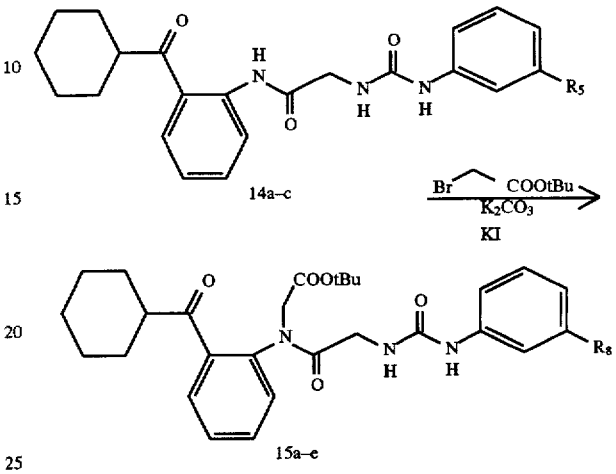

R$_8$= a: —CH$_3$  b: —CF$_3$  c: —COOCH$_2$CH=CH$_2$
d: —COOH  e: —COOCH$_3$

EXAMPLE 36

Cyclohexyl-(2-(N-(t-butoxycarbonylmethyl)-N-(N'-(m-tolyl)ureidomethylcarbonyl)amino)phenyl)ketone 15a According to the same manner as that described in Example 14, the compound 14a prepared in Preparation 24 is used to prepare the titled compound 15a. Mp. 128°–130° C.

IR $v_{max}$(KBr):3383, 1741, 1673, 1647, 1612, 1595, 1557, 1522 cm$^{-1}$.

NMR (CDCl$_3$) δ:1.10–1.53 (5H,m), 1.47 (9H,s), 1.62–1.97 (5H,m), 2.27 (3H,s), 3.60 (1H,d,J=17.2 Hz), 3.64 (1H,d,J=17.2 Hz), 3.81 (1H,d,J=17.2 Hz),·4.61 (1H,d,17.2 Hz), 6.78 (1H,m), 7.06–7.20 (4H,m), 7.54–7.73 (4H,m), 7.91(1H,m).

Elemental Analysis (C$_{29}$H$_{37}$N$_3$O$_5$) Calcd.: C,68.62;H, 7.35;N,8.28 Found: C,68.42;H,7.34;N,8.32.

EXAMPLE 37

Cyclohexyl-(2-(N-(t-butoxycarbonylmethyl)-N-(N'-(m-trifluoromethylphenyl)ureidomethylcarbonyl)amino)phenyl)ketone 15b According to the same manner as that described in Example 14, the compound 14b prepared in Preparation 25 is used to prepare the titled compound 15b. Amorphous solid.

IR $v_{max}$(KBr):3374, 1741, 1741, 1685, 1651,1597, 1560, 1511 cm$^{-1}$.

NMR (CDCl$_3$) δ:1.11–1.60 (5H,m), 1.47 (9H,s), 1.63–1.96 (5H,m), 3.20 (1H,m), 3.60 (1H,d,J=17.0 Hz), 3.66 (1H,d,J=18.4 Hz), 3.82 (1H,d,J=18.4 Hz), 4.61 (1H,d,J=17.0 Hz), 7.06–7.28 (2H,m), 7.33–7.52 (2H,m), 7.56–7.76 (2H, m), 7.81 (1H,br.s), 7.88 (1H,m).

Elemental Analysis (C$_{29}$H$_{34}$F$_3$N$_3$O$_5$) Calcd.: C,62.02;H, 6.10;F,10.15;N,7.48

Found :C,61.79;H,6.08;F,9.89;N,7.39.

EXAMPLE 38

Cyclohexyl-(2-(N-(t-butoxycarbonylmethyl)-N-(N'-(m-(aryloxycarbonyl)phenyl)ureidomethylcarbonyl)amino)phenyl)ketone 15c According to the same manner as that described in Example 14, the compound 14c prepared in Preparation 26 is used to synthesize the titled compound 15c. Amorphous solid.

IR $v_{max}$(KBr):3374, 1722, 1685, 1650, 1594, 1555 cm$^{-1}$.

NMR (CDCl$_3$) δ:1.12–1.95 (10H,m), 1.40 (9H,s), 3.07 (1H,m), 3.53 (1H,d,J=17.2 Hz), 3.73 (1H,d,J=17.4 Hz), 3.93 (1H,d,J=17.4 Hz), 4.77–4.82 (2H,m), 4.80 (1H,d,J=17.2 Hz), 5.19–5.47 (2H,m), 5.89–6.22 (2H,m), 7.13–7.35 (3H,m), 7.48–7.78 (4H,m), 7.80 (1H,br.s).

Elemental Analysis (C$_{32}$H$_{39}$N$_3$O$_7$·0.2H$_2$O) Calcd.: C,66.12;H,6.68;N,7.23 Found: C,66.18;H,6.79;N,7.17.

EXAMPLE 39

Cyclohexyl-(2-(N-(t-butoxycarbonylmethyl)-N-(N'-(m-carboxyphenyl)ureidomethylcarbonyl)amino)phenyl)ketone 15d According to the same manner as that described in Example 23, the compound 15c is used to prepare the titled compound 15d. Mp. 175°–181° C.

IR $v_{max}$(KBr):3379, 1735, 1685, 1610, 1595, 1554 cm$^{-1}$.

NMR (CDCl$_3$) δ:1.08–1.55 (5H,m), 1.46 (9H,s), 1.61–1.98 (5H,m), 3.19 (1H,m), 3.60 (1H,d,J=17.2 Hz), 3.66 (1H,d,J=17.0 Hz), 3.83 (1H,d,J=17.0 Hz), 4.62 (1H,d,J=17.2 Hz), 7.27 (1H,t,J=6.0 Hz), 7.51–7.75 (5H,m), 7.86–7.93 (2H,m).

Elemental Analysis (C$_{29}$H$_{35}$N$_3$O$_7$·1.2H$_2$O) Calcd.: C,62.29;H,6.74;N,7.51 Found: C,62.11 ;H,6.35;N,7.37.

EXAMPLE 40

Cyclohexyl-(2-(N-(t-butoxycarbonylmethyl)-N-(N'-(m-carbomethoxyphenyl)ureidomethylcarbonyl)amino)phenyl)ketone 15e According to the same manner as that described in Example 30, the compound 15d is used to prepare the titled compound 15e. Amorphous solid.

IR $v_{max}$ (KBr):3380, 1724, 1664, 1594, 1555 cm$^{-1}$.

NMR (CDCl$_3$) δ:1.13–1.93 (10H,m), 1.43 (9H,s), 3.07 (1H,m), 3.49 (1H,d,J=17.1 Hz), 3.75 (1H,dd,J=17.1, 5.1 Hz), 3.88 (3H,s), 3.90 (1H,dd,J=17.1, 5.1 Hz), 4.80 (1H,d,J=17.1 Hz), 5.87 (1H,br.s), 6.93 (1H,s), 7.43–7.84 (8H,s), 7.94 (1H,s).

Elemental Analysis (C$_{30}$H$_{37}$N$_3$O$_7$·0.2H$_2$O) Calcd.: C,64.90;H,6.79;N,7.57 Found: C,64.95;H,6.52;N,7.48.

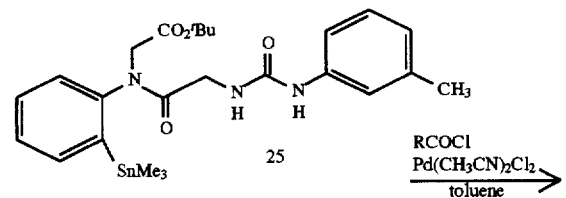

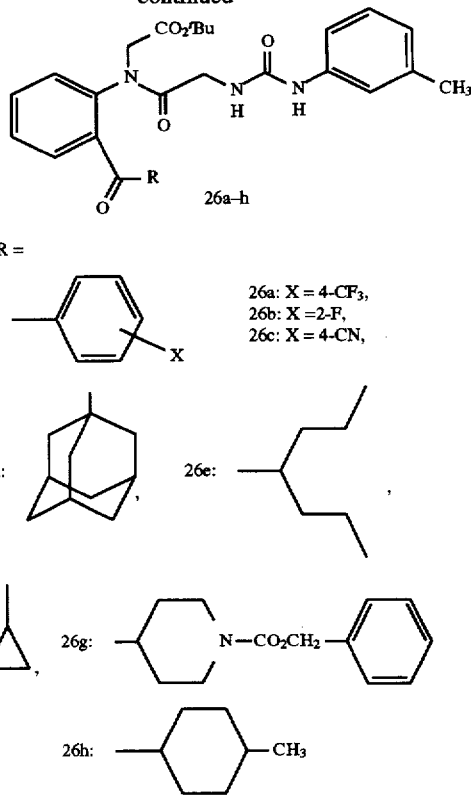

EXAMPLE 41 tert-Butyl((2-(4-trifluoromethylbenzoyl)phenyl)-(2-(3-m-tolylureido)-acetyl)amino)acetate 26a To a solution of 4-trifluoromethylbenzoyl chloride (53 μl, 0.36 mmol) in toluene (4 ml) is added dichlorobisacetonitrile palladium (12.5 mg, 0.036 mmol) at room temperature. Then, tert-butyl((2-trimethylstannylphenyl)-(2-(3-m-tolylureido)acetyl)amino)acetate (compound 25) (200 mg, 0.36 mmol) is added, and the mixture is stirred at 50° C. for 20 minutes. After addition of dichlorobisacetonitrile palladium (6.2 mg, 0.018 mmol), stirring is confinated for additional 10 minutes. To the reaction solution is added ice-cooled water. After stirring, the aqueous layer is extracted twice with ethyl acetate. The organic layer is washed with saturated brine, dried over anhydrous magnesium sulfate and then concentrated. The residue is purified by subjecting to silica gel column chromatography to obtain the objective compound 26a (93 mg). Yield 46%.

NMR(CDCl$_3$) δ:1.40 (9H,s), 2.28 (3H,s), 3.70 (1H,d,J= 17.2 Hz), 3.80(1H,dd,J=4.4 Hz, 17.7 Hz), 3.97 (1H,dd,J=4.6 Hz, 17.7 Hz), 4.63 (1H,d,J=17.2 Hz), 5.77–5.87 (1H,m), 6.67 (1H,brs), 6.80–7.18 (4H,m), 7.41–7.94 (8H,m).

EXAMPLE 42 tert-Butyl((2-(2-fluorobenzoyl)phenyl)-(2-(3-m-tolylureido)acetyl)amino)acetate 26b According to the synthesis method for the compound 26a, tert-butyl((2-trimethyl-stannylphenyl)-(2-(3-m-tolylureido)acetyl)amino)acetate (compound 25) (200 mg) and 2-fluorobenzoyl chloride (43 μl) are used to synthesize the titled compound 26b (56 mg). Yield 30%.

NMR(CDCl₃) δ:1.41 (9H,s), 2.28 (3H,s), 3.68 (1H,d,J=17.6 Hz), 3.81(1H,dd,J=4.2 Hz, 17.5 Hz), 4.01 (1H,dd,J=4.6 Hz, 17.5 Hz), 4.67 (1H,d,J=17.6 Hz), 5.82–5.95 (1H,m), 5.98–7.75 (13H,m).

EXAMPLE 43 tert-Butyl((2-(4-cyanobenzoyl)phenyl)-(2-(3-m-tolylureido)acetyl)amino)acetate 26c According to the synthesis method for the compound 26a, tert-butyl((2-trimethyl-stannylphenyl)-(2-(3-m-tolylureido)acetyl)amino)acetate (compound 25) (200 mg) and 4-cyanobenzoyl chloride (59 mg) are used to synthesize the titled compound 26c (88 mg). Yield 47%.

¹H NMR(CDCl₃) δ ppm:1.39 (9H,s), 2.29 (3H,s), 3.74 (1H,d,J=17.2 Hz), 3.80 (1H,dd,J=4.6 Hz, 17.6 Hz), 3.93 (1H,dd,J=4.2 Hz, 17.6 Hz), 4.60 (1H,d,J=17.2 Hz), 5.82–5.89 (1H,m), 6.73–7.20 (5H,m), 7.42–7.94 (8H,m).

EXAMPLE 44 tert-Butyl((2-(adamantane-1-carbonyl)phenyl)-(2-(3-m-tolylureido)acetyl)-amino)acetate 26d According to the synthesis method for the compound 26a, tert-butyl((2-trimethylstannylphenyl)-(2-(3-m-tolylureido)acetyl)amino)acetate (compound 25) (250 mg) and adamantane-1-carbonyl chloride (89 mg) are used to synthesize the titled compound 26d (40 mg). Yield 16%.

¹H NMR (CDCl₃) δ ppm:1.43 (9H,s), 1.71 (6H,s), 1.90 (6H,s), 2.05 (3H,s), 2.30 (3H,s), 3.69 (1H,d,J=17.2 Hz), 3.90 (1H,d,J=17.4 Hz), 4.01 (1H,d,17.4 Hz), 4.63 (1H,d,J=17.2 Hz), 5.83 (1H,brs), 6.74–7.46(9H,m).

EXAMPLE 45 tert-Butyl((2-(1-oxo-2-propylpentyl)-(2-(3-m-tolylureido)acetyl)amino)acetate 26e According to the synthesis method of the compound 26a, tert-butyl((2-trimethylstannylphenyl)-(2-(3-m-tolylureido)acetyl)amino)acetate (compound 25) (42 mg) and 2-n-propyl-n-valeroyl chloride (12 mg) are used to synthesize the titled compound 26e (7 mg). Yield 18%.

NMR (CDCl₃) δ:0.85–0.91 (6H,m), 1.42 (9H,s), 2.30 (3H,s), 3.49 (1H,d,J=17.4 Hz), 3.65 (1H,d,17.4 Hz), 3.92 (1H,d,17.4 Hz), 4.84 (1H,d,J=17.4 Hz), 5.97 (1H,brs), 6.80–7.18 (5H,m), 7.38–7.78 (4H,m).

EXAMPLE 46 tert-Butyl((2-(cyclopropanecarbonyl)phenyl)-(2-(3-m-tolylureido)acetyl)-amino)acetate 26f According to the synthesis method for the compound 26a, tert-butyl((2-trimethylstannylphenyl)-(2-(3-m-tolylureido)acetyl)amino)acetate (compound 25) (112 mg) and cyclopropanecarbonyl chloride (18.1 μl) are used to synthesize the titled compound 26f (45 mg). Yield 48%.

NMR (CDCl₃) δ:1.02–1.14 (2H,m), 1.19–1.31 (2H,m), 1.41 (9H,s), 2.28 (3H,s), 2.38–2.47 (1H,m), 3.56 (1H,d,J=17.4 Hz), 3.76 (1H,dd,J=5.0 Hz,17.5 Hz), 3.90 (1H,dd,J=4.6 Hz,17.5 Hz), 4.82 (1H,d,J=17.4 Hz),5.98–6.07 (1H,m), 6.82 (1H,d,J=7.0 Hz), 6.99–7.21 (4H,m), 7.39–7.70(3H,m), 7.81–7.88 (1H,m).

EXAMPLE 47 tert-Butyl((2-(trans-4-methylcyclohexane-1-carbonyl)phenyl)-(2-(3-m-tolylureido)acetyl)amino)acetate 26g According to the synthesis method for the compound 26a, tert-butyl((2-trimethylstannylphenyl)-(2-(3-m-tolylureido) acetyl)amino)acetate (compound 25) (112 mg) and acid chloride synthesized from thionyl chloride (120 μl) and trans-4-methylcyclohexane-1-carboxylic acid (29 mg) are used to synthesize the titled compound 26g (35 mg). Yield 34%.

NMR (CDCl₃) δ:0.84–1.93 (9H,m), 0.90 (3H,d,J=6.4 Hz), 1.43 (9H,s),2.30 (3H,s),2.90–3.07 (1H,m), 3.48 (1H,d, J=17.2 Hz), 3.68 (1H,dd,J=4.6 Hz, 17.7 Hz), 3.89 (1H,dd, J=4.6 Hz, 17.7 Hz), 4.80 (1H,d,J=17.2 Hz),5.85–5.99 (1H, m), 6.74 (1H,s), 6.85 (1H,d,J=6.8 Hz), 7.02–7.32 (3H,m), 7.47–7.76 (4H,m).

EXAMPLE 48 tert-Butyl((2-(N-(benzyloxycarbonyl)piperidine-4-carbonyl)phenyl)-(2-(3-m-tolylureido)acetyl)amino) acetate 26h According to the synthesis method of the compound 26a, ((2-trimethylstannylphenyl)-(2-(3-m-tolylureido)acetyl) amino)tert-butyl acetate (compound 25) (420 mg) and acid chloride synthesized from thionyl chloride (220 μl) and N-(benzyloxycarbonyl)piperidine-4-carboxylic acid (198 mg) (compound described in J. Med. Chem. 1988, 31, 613–617) are used to synthesize the titled compound 26h (232 mg). Yield 48%.

NMR (CDCl₃) δ:1.41 (9H,s), 1.50–1.92 (4H,m), 2.28 (3H,s), 2.77–3.02 (2H,m), 3.16–3.36 (1H,m), 3.50 (1H,d,J= 17.2 Hz), 3.72 (1H,dd,J=4.6 Hz, 17.6 Hz), 3.85 (1H,dd,J=4.2 Hz, 17.6 Hz), 4.04–4.34 (2H,m), 4.75 (1H,d,J=17.2 Hz), 5.86–5.97 (1H,m), 6.77–7.20 (5H,m), 7.48–7.73 (4H,m).

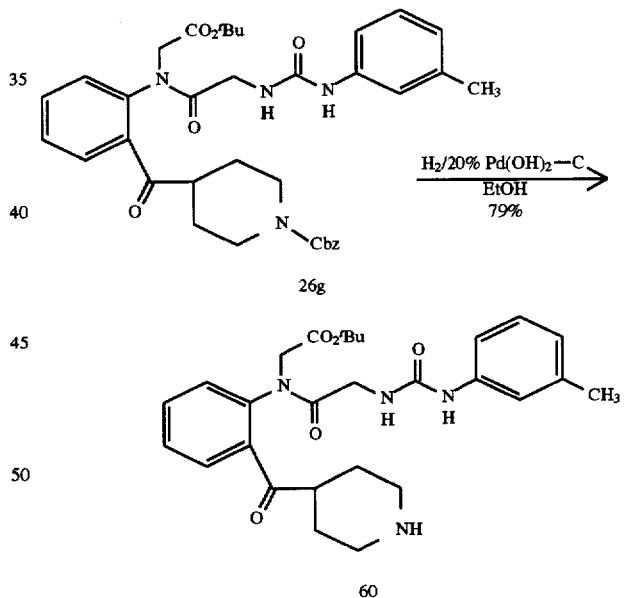

EXAMPLE 49 tert-Butyl((2-(piperidine-4-carbonyl)phenyl)-(2-(3-m-tolylureido)acetyl)-amino)acetate 60 tert-Butyl((2-(N-(benzyloxycarbonyl)piperidine-4-carbonyl)phenyl)-(2-(3-tolylureido)acetyl)amino)acetate and the compound 26 g (9.7 mg, 0.015 mmol) are dissolved in ethano. To the solution is added palladium hydrooxide-carbon powder (2 mg) and stirred under a hydrogen atmosphere (1 atm) at room temperature for 24 hours. The reaction solution is filtered and the filtrate is concentrated under reduced pressure. The residue is purified by silica gel column chromatography to obtain the objective compound 60 (6.0 mg). Yield 79%.

NMR (CDCl$_3$) δ:1.42 (9H,s), 1.53–1.76 (2H,m), 1.76–1.92 (2H,m), 2.29 (3H,s), 2.60–2.82 (2H,m), 3.08–3.28 (3H,m), 3.52 (1H,d,J=17.2 Hz), 3.63–3.76 (1H, m), 3.79–3.94 (1H,m), 4.77 (1H,d,J=17.2 Hz), 5.99 (1H, brs), 6.83 (1H,d,J=6.6 Hz), 7.02–7.19 (4H,m), 7.46–7.77 (4H,m)

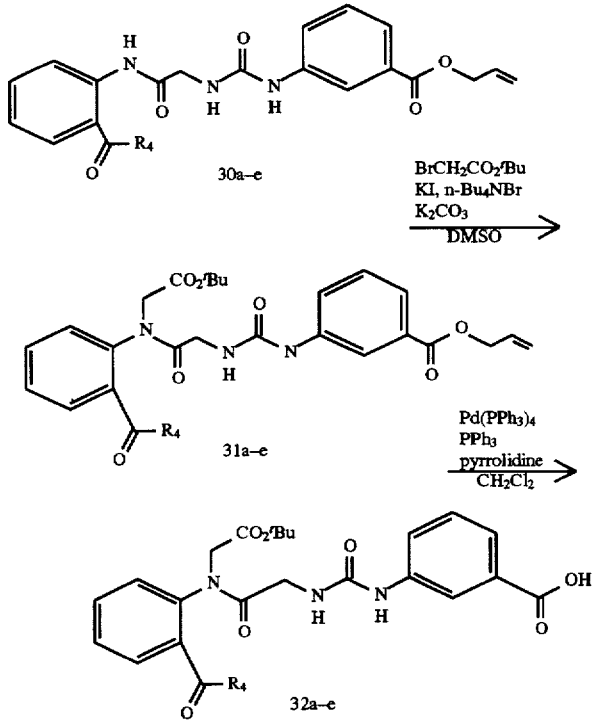

EXAMPLE 50
Allyl 3-(3-(tert-butoxycarbonylmethyl(2-(2-fluorobenzoyl)phenylcarbamoylmethyl)ureido) benzoate 31a According to the production process for the compound 24, the compound 30a (350 mg) is used as the starting material to synthesize the titled compound 31a (230 mg). Yield 65%.

NMR (CDCl$_3$) δ:1.38 (9H,s), 3.72 (1H,d,J=17.6 Hz), 3.85 (1H,dd,J=4.4 Hz, 17.4 Hz), 4.04 (1H,dd,J=5.2 Hz, 17.4 Hz), 4.65 (1H,d,J=17.6 Hz), 4.78 (2H,d,J=5.4 Hz), 5.20–5.46 (2H,m), 5.91–6.12 (2H,m), 7.05–8.02(13H,m).

EXAMPLE 51
Allyl 3-(3-(tert-butoxycarbonylmethyl(2-(4-trifluoromethylbenzoyl)phenylcarbamoylmethyl) ureido)benzoate 31b According to the production process for the compound 24, the compound 30b (300 mg) is used as the starting material to synthesize the titled compound 31b (238 mg). Yield 56%.

NMR (CDCl$_3$) δ:1.36 (9H,s), 3.75 (1H,d,J=17.2 Hz), 3.79 (1H,dd,J=4.8 Hz, 17.6 Hz), 4.00 (1H,dd,J=4.8 Hz, 17.6 Hz), 4.61 (1H,d,J=17.2 Hz), 4.78 (2H,d,J=5.4 Hz), 5.20–5.44 (2H,m), 5.90–6.12 (2H,m), 7.18–7.96(13H,m).

EXAMPLE 52
Allyl 3-(3-(tert-butoxycarbonylmethyl(2-(4-cyanobenzoyl)phenylcarbamoylmethyl)ureido) benzoate 31c According to the production process for the compound 24, the compound 30c (390 mg) is used as the starting material to synthesize the titled compound 31c (270 mg). Yield 53%.

NMR (CDCl$_3$) δ:1.36 (9H,s), 3.80 (1H,d,J=17.2Hz), 3.83 (1H,dd,J=4.8 Hz, 17.6 Hz), 3.96 (1H,dd,J=4.8 Hz, 17.6 Hz), 4.58 (1H,d,J=17.2 Hz),4.79 (2H,d,J=5.6 Hz), 5.21–5.44 (2H. m), 5.91–6.12 (2H,m), 7.17–7.94(13H,m).

EXAMPLE 53
Allyl 3-(3-(tert-butoxycarbonylmethyl(2-(adamantane-1-carbonyl)phenylcarbamoylmethyl) ureido)benzoate 31d According to the production process for the compound 24, the compound 30d (44 mg) is used as the starting material to synthesize the titled compound 31d (30 mg). Yield 56%.

NMR (CDCl$_3$) δ:1.41 (9H,s), 1.70 (6H,s), 1.92 (6H,s), 2.05 (3H,s),3.73 (1H,d,J=17.2 Hz), 3.93 (1H,dd,J=4.4 Hz, 17.5 Hz), 4.07 (1H,dd,J=4.8 Hz, 17.5 Hz), 4.63 (1H,d,J=17.2 Hz), 4.79 (2H,d,J=5.6 Hz),5.22–5.46 (2H,m), 5.91–6.13 (2H,m), 7.22–8.02 (9H,m).

EXAMPLE 54
Allyl 3-(3-(tert-butoxycarbonylmethyl(2-(1-oxo-2-propylpentyl)phenyl-carbamoylmethyl)ureido) benzoate 31 e According to the production process of the compound 24, the compound 30e (200 mg) is used as the starting material to synthesize the titled compound 31e (14 mg). Yield 6%.

NMR (CDCl$_3$) δ:0.89 (6H,t,J=7.0 Hz), 1.20–1.78 (8H,m), 1.41 (9H,s), 3.18–3.31 (1H,m), 3.51 (1H,d,J=17.2 Hz), 3.68 (1H,dd,J=4.6 Hz, 17.6 Hz), 3.95 (1H,dd,J=4.6 Hz, 17.6 Hz), 4.79 (1H,d,J=5.6 Hz), 4.83 (2H,d,J=17.2 Hz), 5.22–5.45 (2H,m), 5.91–6.13 (2H,m), 7.10–8.00 (9H,m).

EXAMPLE 55
3-(3-(tert-Butoxycarbonylmethyl(2-(2-fluorobenzoyl)phenylcarbamoylmethyl)ureido) benzoic acid 32a According to the same manner as that described in Example 21-(3), the compound 31a (60 mg) is used as the starting material to synthesize the titled compound 32a (40 mg). Yield 71%.

NMR (CDCl$_3$) δ:1.48 (9H,s), 3.70 (1H,d,J=17.0 Hz), 3.89 (1H,dd,J=3.2 Hz, 18.1 Hz), 4.05 (1H,dd,J=3.2 Hz, 18.1 Hz), 4.74 (1H,d,J=17.0 Hz),7.05–7.80 (13H,m), 8.20 (1H,s), 8.34–8.43 (1H,m).

EXAMPLE 56
3-(3-(tert-Butoxycarbonylmethyl(2-(4-trifluoromethylbenzoyl)phenylcarbamoylmethyl) ureido)benzoic acid 32b According to the same manner as that described in Example 21-(3), the compound 31b (130 mg) is used as the starting material to synthesize the titled compound 32b (24 mg). Yield 20%.

NMR (CDCl$_3$) δ:1.46 (9H,s), 3.73 (1H,d,J=17.2 Hz), 3.84 (1H,dd,J=3.8 Hz, 18.8 Hz), 3.94 (1H,dd,J=3.8 Hz, 18.8 Hz), 4.70 (1H,d,J=17.2 Hz), 7.17 (1H,brs), 7.29–7.98 (11H,m), 8.14 (1H,s), 8.28 (1H,d,J=7.6).

EXAMPLE 57

3-(3-(tert-Butoxycarbonylmethyl(2-(4-cyanobenzoyl)phenylcarbamoylmethyl)ureido) benzoic acid 32c According to the same manner as that described in Example 21-(3), the compound 31c (200 mg) is used as the starting material to synthesize the titled compound 32c (133 mg). Yield 71%.

NMR (CDCl$_3$) δ:1.47 (9H,s), 3.76 (1H,d,J=17.2 Hz), 3.83 (1H,dd,J=4.0 Hz, 17.6 Hz), 3.94 (1H,dd,J=4.0 Hz, 17.6Hz), 4.68 (1H,d,J=17.2Hz), 7.16 (1H,brs), 7.31–7.94 (m,11H), 8.15 (1H,s), 8.26–8.34 (1H,m).

EXAMPLE 58

3-(3-(tert-Butoxycarbonylmethyl(2-(adamantane-1-carbonyl)phenylcarbamoylmethyl)ureido)benzoic acid 32d According to the same manner as that described in Example 21-(3), the compound 31d (30 mg) is used as the starting material to synthesize the titled compound 32d (17 mg). Yield 61%.

NMR (CDCl$_3$) δ:1.49 (9H,s), 1.68 (6H,s), 1.90 (6H,s), 2.05 (3H,s), 3.73 (1H,d,J=17.2 Hz), 3.96 (1H,dd,J=3.6 Hz, 18.4 Hz), 4.10 (1H,dd,J=3.6 Hz, 18.4 Hz), 4.65 (1H,d,J=17.2 Hz), 7.19 (1H,brs), 7.30–7.78 (8H,m), 8.15 (1H,s), 8.34–8.41 (1H,m).

EXAMPLE 59

3-(3-(tert-Butoxycarbonylmethyl(2-(1-oxo-2-propylpentyl)phenylcarbamoylmethyl)ureido) benzoic acid 32e According to the same manner as that described in Example 21-(3), the compound 31e (14 mg) is used as the starting material to synthesize the titled compound 32e (7 mg). Yield 54%.

NMR (CDCl$_3$) δ:0.90 (6H,t,J=7.0 Hz), 1.18–1.76 (8H,m), 1.49 (9H,s), 3.18–3.34 (1H,m), 3.53 (1H,d,J=17.2 Hz), 3.73 (1H,dd,J=3.6 Hz, 18.2 Hz), 3.96 (1H,dd,J=4.6 Hz, 17.6 Hz), 4.85 (1H,d,J=17.2 Hz), 7.20–7.86(7H,m), 8.23 (1H,s), 8.57 (1H,d,J=7.8).

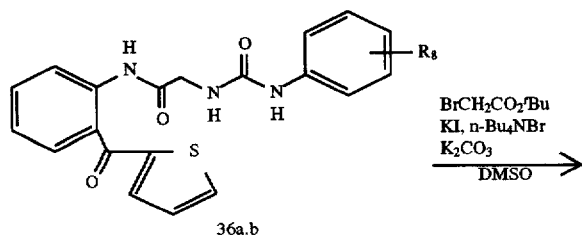

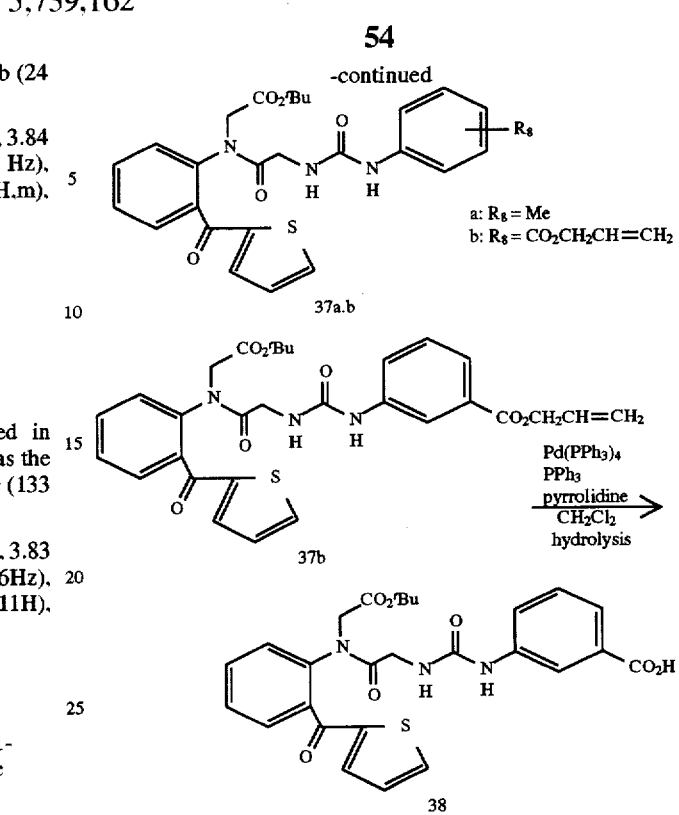

EXAMPLE 60 tert-Butyl((2-(thiophene-2-carbonyl)phenyl-(2-(3-m-tolylureido)acetyl)amino)acetate 37a According to the synthesis method for the compound 24, the compound 36a is used to synthesize the titled compound 37a. Mp. 116° C.

IR ν$_{max}$ (KBr):3347, 1745, 1645, 1614, 1563 cm$^{-1}$.

NMR (CDCl$_3$) δ:1.43 (9H,s), 2.31 (3H,s), 3.70 (1H,d,J=17.1 Hz), 4.74 (1H,d,J=17.1 Hz), 3.75 (1H,d,J=17.4 Hz), 4.00 (1H,d,J=17.4Hz), 5.80 (1H,brs), 6.67 (1H,m), 6.87 (1H,m), 7.01 (1H,m), 7.10–7.22 (3H,m), 7.50–7.70 (4H,m), 7.75–7.80 (2H,m).

Elemental Analysis (C$_{27}$H$_{29}$N$_3$O$_5$S) Calcd.: C, 63.89; H, 5.76; N, 8.28; S, 6.32 Found: C, 64.01; H, 5.88; N, 8.25; S, 6.51.

EXAMPLE 61

Allyl 3-(3-(tert-butoxycarbonylmethyl(2-(thiophene-2-carbonyl)phenyl-carbamoylmethyl)ureido) benzoate 37b According to the synthesis method of the compound 24, the compound 36b is used to synthesize the titled compound 37b. Mp. 142° C.

IR ν$_{max}$ (KBr):3343, 1742, 1722, 1645, 1595, 1561 cm$^{-1}$.

NMR (CDCl$_3$) δ:1.40 (9H,s), 3.69 (1H,d,J=17.5 Hz), 4.71 (1H,d,J=17.5 Hz), 3.78 (1H,d,J=17.5 Hz), 4.00 (1H,d,J=17.5 Hz), 4.80 (2H,dt,J=6.0 Hz, 0.8 Hz), 5.26 (1H,dd,J=9.0 Hz, 1.5 Hz), 5.39 (1H,dd,J=17.4 Hz,1.8 Hz), 5.80–6.08 (2H,m), 7.02 (1H,s), 7.15 (1H,m), 7.31 (1H,m), 7.50–7.70 (6H,m), 7.78 (2H,m), 7.93 (1H,m).

Elemental Analysis (C$_{30}$H$_{31}$N$_3$O$_7$S) Calcd.: C, 62.38; H, 5.41; N, 7.27; S, 5.55 Found: C, 62.19; H, 5.43; N, 7.26; S, 5.53.

EXAMPLE 62

3-(3-(tert-Butoxycarbonylmethyl(2-(thiophene-2-carbonyl)phenylcarbamoylmethyl)ureido)benzoic acid 38

According to the same manner as that described in Example 21-(3), the compound 37b is used as the starting material to synthesize the titled compound 38. Mp. 184°–186° C.

IR $v_{max}$ (KBr):3385, 1735, 1698, 1648, 1560 cm$^{-1}$.

NMR (DMSO-d$_6$) δ:1.38 (9H,s), 3.58 (1H,dd,J=16.8 Hz, 4.2 Hz), 3.78 (1H,dd,J=16.8Hz, 4.2 Hz), 3.72 (1H,d,J=17.2 Hz), 4.29 (1H,d,J=17.2 Hz), 6.37 (1H,t,J=4.4 Hz), 7.20–7.35 (2H,m), 7.40–7.80 (7H,m), 7.99 (1H,m), 8.18 (1H,dd,J=5.0 Hz, 1.2 Hz), 8.99 (1H,s).

Elemental Analysis (C$_{27}$H$_{27}$N$_3$O$_7$S.0.2H$_2$O) Calcd.: C, 59.92; H, 5.10; N, 7.76; S, 5.92 Found: C, 59.87; H, 5.17; N, 7.66; S, 5.87.

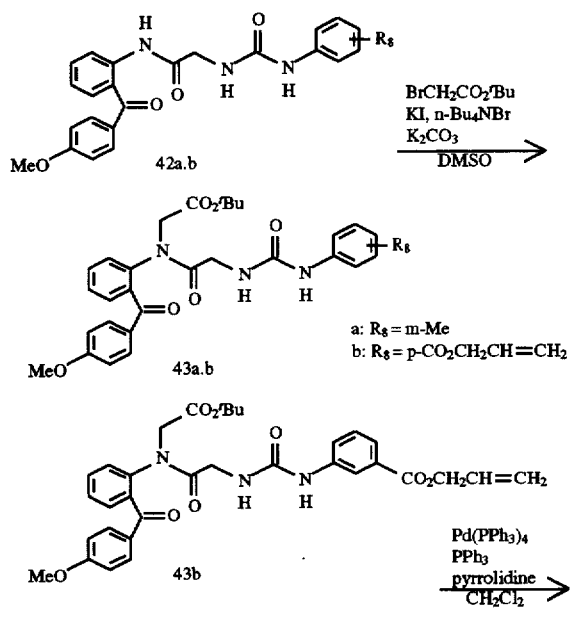

a: R$_8$ = m-Me
b: R$_8$ = p-CO$_2$CH$_2$CH=CH$_2$

EXAMPLE 63 tert-Butyl((2-(4-Methoxybenzoyl)phenyl)-(2-(3-m-tolylureido)acetyl)amino)acetate 43a According to the synthesis method of the compound 24, the compound 42a is used to synthesize the titled compound. Mp. 228°–230° C.

IR $v_{max}$ (KBr):3330, 1744, 1670, 1640, 1600 cm$^{-1}$.

NMR (DMSO-d$_6$) δ:1.36(9H,s), 2.22 (3H,s), 3.62 (1H, dd,J=18 Hz, 5.1 Hz), 3.68 (1H,d,J=16.8 Hz), 3.77 (1H,dd, J=18.0 Hz, 5.1 Hz), 3.83 (3H,s), 4.20 (1H,d,J=16.8Hz), 6.36 (1H,t,J=5.1 Hz), 6.70 (1H,d,J=7.5 Hz),7.05–7.18 (5H,m), 7.52–7.76 (5H,m), 8.79 (1H,s).

Elemental Analysis (C$_{30}$H$_{33}$N$_3$O$_6$) Calcd.: C, 67.78; H, 6.25; N, 7.90 Found: C, 67.75; H, 6.35; N, 7.98.

EXAMPLE 64

Allyl 3-(3-(tert-butoxycarbonylmethyl(2-(4-methoxybenzoyl)phenyl)carbamoylmethyl)ureido) benzoate 43b According to the synthesis method of the compound 24, the compound 42b is used to synthesize the titled compound. Mp. 190°–191° C.

IR $v_{max}$ (KBr): 1741, 1721, 1645, 1599, 1566 cm$^{-1}$.

NMR (DMSO-d$_6$) δ:1.38 (9H,s), 3.60–3.85 (3H,m), 3.84 (3H,s), 4.20 (1H,d,J=16.8 Hz), 4.79 (2H,d,J=5.4 Hz), 5.27 (1H,d,J=7.5 Hz), 5.39 (1H,d,J=17.1 Hz), 5.98–6.11 (1H,m), 6.38 (1H,t,J=4.5 Hz), 7.08 (2H,d,J=9.0 Hz), 7.37 (1H,t,J=8.0 Hz), 7.49–7.76 (8H,m), 8.10 (1H,s), 9.07(1H,s).

Elemental Analysis (C$_{33}$H$_{35}$N$_3$O$_8$) Calcd.: C, 65.88; H, 5.86; N, 6.98 Found: C, 65.70; H, 5.91; N, 6.97.

EXAMPLE 65

3-(3-(tert-Butoxycarbonylmethyl(2-(4-methoxybenzoyl)phenyl)carbamoylmethyl)ureido) benzoic acid 44

According to the same manner as that described in Example 21-(3), the compound 43b is used as the starting material to synthesize the titled compound 44. Mp. 198°–200° C.

IR $v_{max}$ (KBr): 1743, 1694, 1647, 1599, 1557 cm$^{-1}$.

NMR (CD$_3$OD) δ:1.43 (9H,s), 3.69 (1H,d,J=17.2 Hz), 3.79 (1H,d,J=17.4 Hz), 3.85 (3H,s), 3.94 (1H,d,J=17.2 Hz), 4.39 (1H,d,J=17.2 Hz), 7.02–7.05 (2H,m), 7.28–7.36 (1H, m), 7.49–7.83 (8H,m), 7.97–7.99 (1H,m).

Elemental Analysis (C$_{30}$H$_{31}$N$_3$O$_8$) Calcd.: C, 64.16; H, 5.56; N, 7.48 Found: C, 63.76; H, 5.63; N, 7.35.

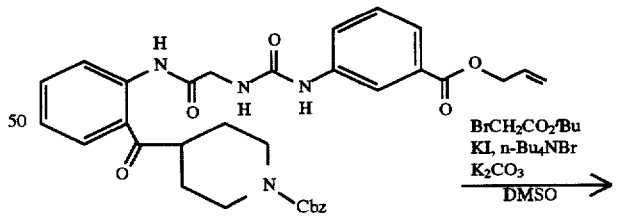

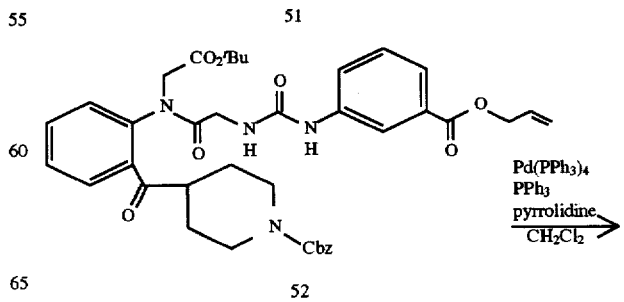

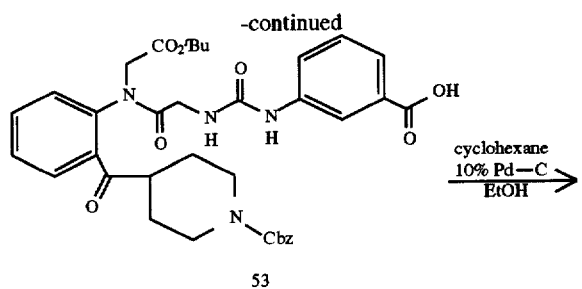

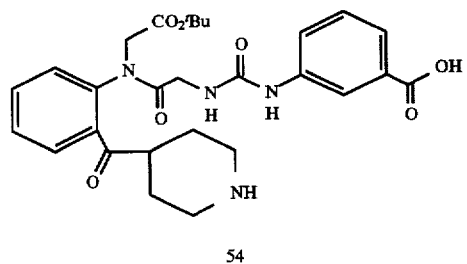

EXAMPLE 66

Allyl 3-(3-tert-butoxycarbonylmethyl(2-(N-(benzyloxycarbonyl)piperidine-4-carbonyl)phenylcarbamoylmethyl)ureido)benzoate 52

According to the synthesis method of the compound 24, allyl 3-(3-(2-(N-(benzyloxycarbonyl)piperidine-4-carbonyl)phenylcarbamoylmethyl)ureido)benzoate, the compound 51 (599 mg) is used as the starting material to synthesize the titled compound 52 (140 mg). Yield 20%.

NMR (CDCl$_3$) δ:1.47–1.74 (2H,m), 1.74–1.94 (2H,m), 1.39 (9H,s), 2.76–3.04 (2H,m), 3.17–3.37 (1H,m), 3.53 (1H,d,J=17.6 Hz), 3.62 (1H,dd,J=4.4 Hz,17.5 Hz), 3.88 (1H,dd,J=4.8 Hz,17.5 Hz), 4.05–4.33 (2H,m),4.74 (1H,d,J=17.6 Hz), 4.77 (2H,d,J=4.2 Hz), 5.12 (2H,s), 5.22–5.44 (2H,m), 5.90–6.17 (2H,m), 7.20–7.41 (7H,m), 7.47–7.76 (6H,m), 7.93(1H,s).

EXAMPLE 67

3-(3-(tert-Butoxycarbonylmethyl(2-(N-(benzyloxycarbonyl)piperidine-4-carbonyl)phenylcarbamoylmethyl)ureido)benzoic acid 53

According to the same manner as that described in Example 21-(3), allyl 3-(3-(tert-butoxycarbanylmethyl(2-N-(benzyloxycarbonyl)piperidine-4-carbonyl)phenylcarbamoylmethyl)ureido)benzoate, the compound 52 (130 mg) is used as the starting material to synthesize the titled compound 53 (96 mg). Yield 78%.

NMR (CDCl$_3$) δ:1.47 (9H,s), 1.51–1.95 (4H,m), 2.80–3.08 (2H,m), 3.20–3.44 (1H,m), 3.54 (1H,d,J=17.2 Hz), 3.69–3.98 (2H,m), 4.18–4.38 (2H,m), 4.79 (1H,d,J=17.2 Hz), 5.11 (2H,s), 7.16 (1H,brs), 7.40–7.87 (8H,m), 8.21–8.40 (2H,m).

EXAMPLE 68

3-(3-(tert-Butoxycarbonylmethyl(2-(piperidine-4-carbonyl)phenylcarbamoylmethyl)ureido)benzoic acid 54

To a solution of 3-(3-(tert-butoxycarbonylmethyl(2-(N-(benzyloxycarbonyl)piperidine-4-carbonyl)phenylcarbamoylmethyl)ureido)benzoic acid (compound 53) (19 mg, 1.49 μmol) in ethanol (1.0 ml) are added cyclohexene (144 μl) and 10% palladium-carbon (15 mg), and the mixture is refluxed with stirring for 30 minutes. The reaction solution is filtered and the filtrate is concentrated under reduced pressure to obtain the titled compound 54 (12 mg). Yield 79%.

NMR (CD$_3$OD) δ:1.44 (9H,s), 1.65–2.19 (4H,m), 3.17–3.91 (5H,m), 3.64 (1H,d,J=17.2 Hz), 3.68 (1H,d,J=17.2 Hz), 3.84 (1H,d,J=17.2 Hz), 4.65 (1H,d,J=17.2 Hz), 7.12–7.84 (7H,m), 8.17 (1H,m).

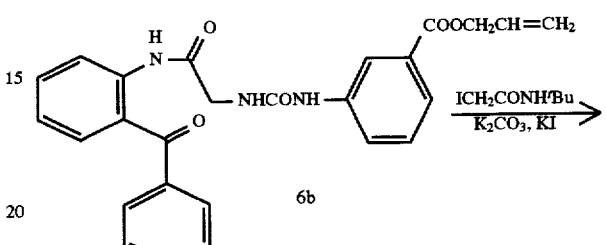

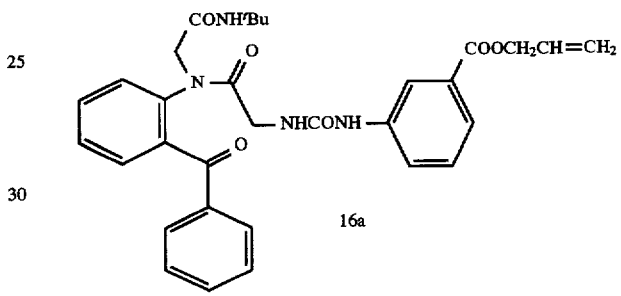

EXAMPLE 69

2-(N-(tert-Butylcarbamoylmethyl)-N'-(m-(aryloxycarbamoyl)phenyl)ureidomethylcarbonylamino)benzophenone 16a According to the same manner as that described in Example 14, the compound 6b is used as the starting substance to synthesize the titled compound. Powder.

IR ν$_{max}$ (KBr):3372, 3068, 2969, 2931, 1719, 1662 cm$^{-1}$.

NMR(CDCl$_3$) δ:1.20 (7H,s), 1.36 (2H,s), 3.76 (1H,d,J=15.6 Hz), 3.84(1H,dd,J=4.8 Hz, 17.4 Hz), 3.97 (1H,dd, 1H,J=4.8 Hz, 17.1 Hz), 4.32 (1H,d,J=15.6 Hz), 4.78 (1H, J=3.8 Hz), 7.42–7.80 (12H,m), 7.95 (1H,t,J=1.8 Hz).

Elemental Analysis (C$_{32}$H$_{34}$N$_4$O$_6$·0.2C$_6$H$_{14}$·0.1H$_2$O) Calcd.:C, 67.44; H, 6.31; N, 9.47 Found:C, 67.19; H, 6.55; N, 9.59.

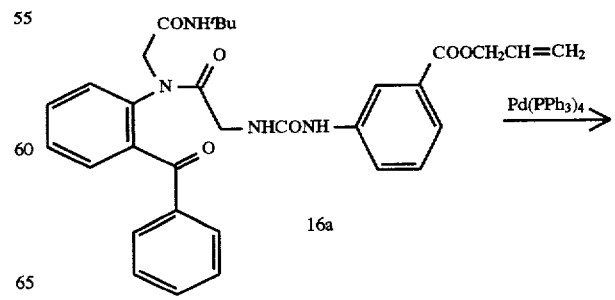

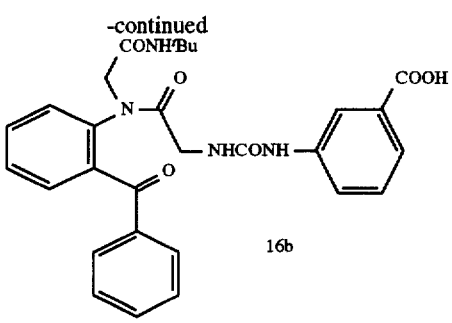

EXAMPLE 70

2-(N-(tert-Butylcarbamoylmethyl)-N'-(m-carboxyphenyl)ureidomethylcarbonylamino) benzophenone 16b According to the same manner as that described in Example 23, the compound 16a is used as the starting substance to synthesize the titled compound. Powder.

IR $\nu_{max}$ (KBr):3376,3067,2969,1661 cm$^{-1}$.

NMR(CDCl$_3$+CD$_3$OD):1.24 (9H,s), 3.76 (1H,d,J=15.6 Hz), 3.80 (1H,d,J=17.4 Hz), 3.99 (1H,d,J=17.4 Hz), 4.40 (1H,d,J=15.6 Hz), 7.30–7.89 (13H,m).

Elemental Analysis (C$_{29}$H$_{30}$N$_4$O$_6$·0.1C$_6$H$_{14}$·0.25C$_4$H$_{10}$·0.4H$_2$O) Calcd.:C, 65.06; H, 6.19; N, 9.92 Found:C, 64.92; H, 6.48; N, 10.22.

The gastrin-inhibitory pharmacological action of the compound (I) prepared in the Examples was examined by in-vitro and in-vivo tests.

Experiment 1 In Vivo Test

Evaluation of Inhibitory Effect on Gastric Acid Secretion by Child Method

Twenty four hour starved (ad libitum for water) male Sprague Daily rats (8-week-old) were anesthetized with urethane (1.5 g/kg S.C.) and kept breathing with esophagus cannulas. After laparotomy, esophagus cannulas were inserted orally up to proventriculus and ligated around gastric cardiac. Perfusion cannulas were inserted from duodenum into stomach and ligated around pylorus. Another cannulas were placed into duodenum and ligated for administration of drug. After sutra of abdomen, stomach was perfused via the esophagus cannulas with physiological saline (37° C.) while collecting perfusate for a 15 min interval. The perfusate was subjected to titration with 0.001N NaOH solution to determine the acidity. When the basal acid secretion became stable, pentagastrin (10 µl/kg/hr) was administered in a sustained manner via common carotid vein for about 90 min until the acid secretion reached approximately the highest level, when a test compound (0.5% M.C. suspension) was administered into duodenum through cannulas. The perfusate was collected for a 15 min interval to monitor the acid secretion for 90 min. The percent inhibition was calculated as follows:

Percent inhibition (%)=100×(A−B)/(C−B)

A: the minimum value of total acidity observed after the administration of a test compound;

B: the total acidity obtained immediately before the administration of pentagastrin; and C: the total acidity obtained immediately before the administration of a test compound.

Results are summarized in Table 1 below.

Experiment 2 In Vitro Test for Evaluation of Gastrin and/or CCK-B Antagonism

The pharmacological effect of compounds (I) prepared in Examples above were evaluated in vitro with respect to antagonistic activity against gastrin receptor, CCK-B receptor or CCK-A receptor, using fundic gland cells of guinea pig, crude membrane specimen from mouse cerebral cortex, or crude membrane specimen from mouse pancreas, respectively.

Animals used in test

Male Hartley guinea pig (450–600 g) or male ddY mouse (24–30 g) were used.

(1) Gastrin Receptor Antagonism

Preparation of gastric glands

Male Hadley guinea pigs (450–600 g) were killed by bleeding and stomach was extracted from each animal immediately, from which gastric glands were prepared.

Preparation of test compounds and procedures of displacing assay A 1M solution of a compound to be tested in DMSO is prepared and diluted with 50% DMSO to obtain a ten-fold dilution series.

The reaction is initiated by the addition of gastric glands to solutions of different concentration each containing $^{125}$I-labeled gastrin (final concentration, 0.2 nM). The mixture is incubated for 30 min at 25° C., centrifuged at 2000 rpm for 5 min and the supernatant is removed by aspiration. To the pellet is added ice-cooled incubation buffer and mixed gently, followed by an immediate centrifugation and removal of the supernatant by aspiration. The radioactivity is counted on gamma counter. The same procedure was repeated using 50% DMSO solution or human gastrin I (final concentration, 2 µM) instead of a solution of test compound so as to obtain the control value regarding total binding or the value regarding non-specific binding, respectively.

Calculation of IC$_{50}$

The IC$_{50}$ was determined by plotting the ratio (%) of specific binding of a test compound to that of control on semilogarithmic graph and obtaining the concentration corresponding to 50%, wherein:

specific binding of control=total binding (cpm)—non-specific binding (cpm); and specific binding of test compound=total binding (cpm)—non-specific binding (cpm).

(2) CCK-A Receptor Antagonism and CCK-B Receptor Antagonism Preparation of CCK receptor preparations Male ddY mice (24 to 30 g) were killed by decapitation and cerebral cortex (CCK-B) and pancreas (CCK-A) were extracted immediately. Each of cerebral cortex and pancreas was mixed with 50 mM Tris-HCl buffer (pH 7.4) and homogenized with a teflon-glass homogenizer and polytron homogenizer to obtain crude membrane specimens.

Preparation of test compounds and procedures of displacing assay

A 1M solution of a compound to be tested in DMSO is prepared and diluted with 50% DMSO to obtain a ten-fold dilution series.

The reaction is initiated by the addition of crude membrane specimen to solutions of different concentration each containing [$^3$H]CCk-8 (final concentration, 1 nM). The mixture is incubated for 90 min at 25° C., filtered through glass filter with aspiration and washed with a cooled 50 mM Tris buffer. After the addition of Aquazol-2 cocktail the radioactivity is counted. The same procedure was repeated using 50% DMSO solution or Ceruletide (final concentration, 1 µM) instead of a solution of test compound so as to obtain the control value regarding total binding or the value regarding non-specific binding, respectively.

Calculation of $IC_{50}$

The $IC_{50}$ was determined by plotting the ratio (%) of specific binding of a test compound to that of control on semilogarithmic graph and obtaining the concentration corresponding to 50%, wherein:

specific binding of control=total binding (cpm)—non-specific binding (cpm); and specific binding of test compound=total binding (cpm)—non-specific binding (cpm).

Results are shown in Table 1 below.

TABLE 1

| Compound No. | Receptor ($IC_{50}$, nM) | | | Inhibitory Effect on acid secretion in rat |
|---|---|---|---|---|
| | Gastrin | CCK-B | CCK-A | ED50, i.d. (mg/kg) |
| 8i | 2 | 3 | 1700 | |
| 8h | 4 | 64 | 5000 | 0.014 |
| 9l | 7 | 56 | 1350 | 0.04 |
| 8j | 3 | 8 | 2200 | |
| 9m | 2 | 11 | 1350 | |
| 7f | 1 | 8 | 1650 | |
| 7y | 42 | 190 | 1800 | |
| 7z | 6 | 66 | 1900 | |
| 8ha | 2 | 42 | 3400 | 0.003 |
| 8hb | 3 | 54 | 3400 | 0.007 |
| 15b | 5 | 6 | 1150 | 0.026 |
| 15d | 3 | 6 | 2000 | |
| 16a | 25 | 215 | 4400 | |
| 16b | 6.0 | 210 | >10000 | |
| YM-022 | 2 | 2 | 100 | 0.107 |

Experimental results shown above demonstrate that the compounds of the present invention have antagonistic effect against gastrin/CCK-B receptor.

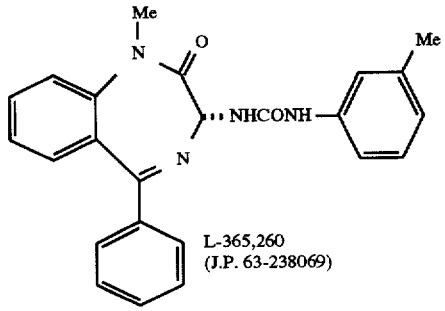

L-365,260
(J.P. 63-238069)

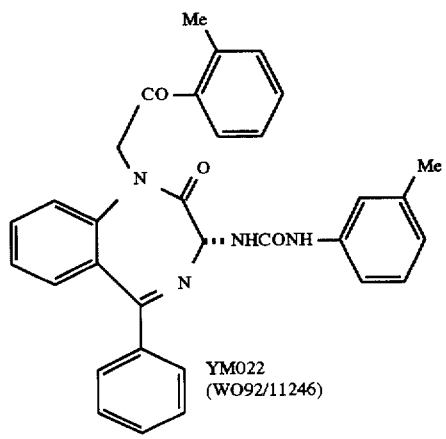

YM022
(WO92/11246)

The following Formulations illustrate the composition of the present invention.

Formulation 1

A hard gelatin capsule containing 50 mg of an active substance, which has the following composition, is prepared in a conventional manner.

| | |
|---|---|
| 2-(N-(tert-Butoxycarbonylmethyl)-N'-(m-(2-(triphenylmethyl)-tetrazol-5-yl)phenyl)ureidomethylcarbonylamino)-benzophenone 7f | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

Formulation 2

A hard gelatin capsule containing 50 mg of an active substance, which has the following composition, is prepared in a conventional manner.

| | |
|---|---|
| 2-[(tert-Butoxycarbonylmethyl)-[3-(m-(carboxyphenyl)-ureidomethylcarbonyl]]amino-benzophenone sodium salt 8ha | 50 mg |
| Cellulose | 18 mg |
| Lactose | 55 mg |
| Colloidal silica | 1 mg |
| Carboxymethylstarch sodium | 10 mg |
| Talc | 10 mg |
| Magnesium stearate | 1 mg |

Formulation 3

A tablet containing 50 mg of an active substance, which has the following composition, is prepared in a conventional manner.

| | |
|---|---|
| 2-[(tert-Butoxycarbonylmethyl)-[3-(m-(carboxyphenyl)ureido-methylcarbonyl]]amino-benzophenone 8h | 50 mg |
| Lactose | 104 mg |
| Cellulose | 40 mg |
| Polyvidone | 10 mg |
| Carboxymethylstarch sodium | 22 mg |
| Talc | 10 mg |
| Magnesium stearate | 2 mg |
| Colloidal silica | 2 mg |
| Mixture of hydroxycellulose,glycerol and titanium oxide (72:3.5:24.5) | Amount required to obtain a film-coated final tablet of 245 mg in weight. |

Formulation 4

A tablet containing 50 mg of an active substance, which has the following composition, is prepared in a conventional manner.

| | |
|---|---|
| 2-(N-(tert-Butoxycarbonyl-methyl)-N'-(m-bromophenyl)ureidomethylcarbonylamino)-benzophenone 7v | 50 mg |
| Lactose | 104 mg |
| Cellulose | 40 mg |
| Polyvidone | 10 mg |
| Carboxymethylstarch sodium | 22 mg |
| Talc | 10 mg |
| Magnesium stearate | 2 mg |
| Colloidal silica | 2 mg |

-continued

| | |
|---|---|
| Mixture of hydroxycellulose, glycero and titanium oxide (72:3.5:24.5) | Amount required to obtain a film-coated final tablet of 245 mg in weight. |

Formulation 5

A solution for injection containing 10 mg of an active substance, which has the following composition, is prepared.

| | |
|---|---|
| 2-(N-(tert-Butoxycarbonylmethyl)-N'-(m-(carboxymethyloxy)phenyl)ureido-methylcarbonylamino)benzophenone 8j | 10 mg |
| Benzoic acid | 80 mg |
| Benzyl alcohol | 0.06 cc |
| Sodium benzoate | 80 mg |
| Ethanol, 95% | 0.4 cc |
| Sodium hydroxide | 24 mg |
| Propylene glycol | 1.6 cc |
| Water | Adqeuate amount to make the total amount 4 cc. |

Formulation 6

A solution for injection containing 10 mg of an active substance, which has the following composition, is prepared.

| | |
|---|---|
| 2-(N-(tert-Butoxycarbonylmethyl)-N'-(p-tolyl)ureido-methylcarbonylamino)-benzophenone 7z | 10 mg |
| Benzoic acid | 10 mg |
| Benzyl alcohol | 0.06 cc |
| Sodium benzoate | 10 mg |
| Ethanol, 95% | 0.4 cc |
| Sodium hydroxide | 5 mg |
| Propylene glycol | 1.6 cc |

What is claimed is:

1. A compound of the formula (I):

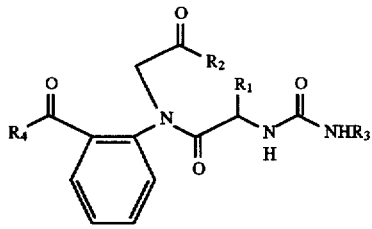

wherein $R_1$ is a hydrogen atom or lower alkyl; $R_2$ is a lower alkyl, alkylamino, lower cycloalkyl, phenyl optionally substituted with 1–3 substituents selected from amino, hydroxy, halogen, lower alkyl and halogenated lower alkyl at the ortho, meta and/or para position or heterocyclic group optionally substituted with 1–3 substituents selected from amino, hydroxy, halogen, lower alkyl, and halogenated lower alkyl; $R_3$ is a phenyl optionally substituted with 1–3 substituents selected from halogen, cyano, lower alkoxy, lower alkyl, halogenated lower alkyl, $—R_5—(CH_2)_n—R_6$ wherein $R_5$ is a bond, $—O—$, $—S—$ or $—S(O)—$, $R_6$ is an aromatic heterocyclic group or $—COOR_7$, wherein $R_7$ is hydrogen, lower alkyl, lower alkenyl, or aralkyl, n is an integer from 0 to 3, $NO_2$, OH, SMe, $CONH$, $OCF_3$, $CH_2CN$, $CH_2OH$, $CH_2OMe$, $CH_2NH_2$ at the ortho-, meta- and/or para- position; $R_4$ is a phenyl optionally substituted with 1–3 substituents selected from amino, hydroxy, halogen, lower alkyl, halogenated lower alkyl and lower alkoxy at the ortho, meta and/or para position, cycloalkyl which is optionally substituted with 1–3 substituents selected from amino, hydroxy, halogen, lower alkyl, halogenated lower alkyl and lower alkoxy alkyl which is optionally substituted with 1–3 substituents selected from amino, hydroxy, halogen, lower alkyl, halogenated lower alkyl and lower alkoxy, or heterocyclic group which is optionally substituted with 1–3 substituents selected from amino, hydroxy, halogen, lower alkyl, halogenated lower alkyl and lower alkoxy; or a pharmaceutically acceptable salt thereof.

2. The compound of claim 1, wherein $R_1$ is a hydrogen atom, $R_2$ is a lower alkoxy or lower alkylamino.

3. The compound of claim 1, wherein $R_4$ is an optionally substituted phenyl.

4. The compound of claim 3, wherein $R_1$ is a hydrogen atom, $R_2$ is $—O—^tBu$, $R_3$ is carboxyphenyl, and $R_4$ is phenyl.

5. A pharmaceutical composition comprising a compound of claim 1.

6. The compound of claim 2, wherein $R_4$ is an optionally substituted phenyl.

7. A pharmaceutical composition comprising a compound of claim 2.

8. A pharmaceutical composition comprising a compound of claim 3.

9. A pharmaceutical composition comprising a compound of claim 4.

10. The compound of claim 1, which is 2-((tert-butoxycarbonylmethyl)-(3-(m-(carboxyphenyl)ureidomethylcarbonyl))-aminobenzophenone.

11. A pharmaceutical composition comprising a compound of claim 10.

12. A method of providing an antagonistic function against a gastrin receptor and/or CCK-B receptor, comprising administering a therapeutically effective amount of the pharmaceutical composition according to claim 5 to a human or animal.

13. A method of treating or preventing an ulcer, comprising administering a therapeutically effective amount of the pharmaceutical composition according to claim 6 to a human or animal.

14. A method of enhancing or lengthening the analgesic effect induced by opoid-type drugs, comprising administering a therapeutically effective amount of the pharmaceutical composition according to claim 5 to a human or animal along with an opoid-type drug.

15. A method of enforcing or lengthening the analgesic effect induced by opoid-type drugs, comprising administering a therapeutically effective amount of the pharmaceutical composition according to claim 5 to a human or animal along with an opoid-type drug.

* * * * *

UNITED STATES PATENT AND TRADEMARK OFFICE
CERTIFICATE OF CORRECTION

PATENT NO. : 5,739,162
DATED : April 14, 1998
INVENTOR(S) : Sanji HAGISHITA et al.

It is certified that error appears in the above-identified patent and that said Letters Patent is hereby corrected as shown below:

Column 63, line 50, claim 1, please delete "alkyl" and insert --alkoxy--.

Signed and Sealed this

Nineteenth Day of January, 1999

Attest:

Attesting Officer

*Acting Commissioner of Patents and Trademarks*